United States Patent
Fearon

(10) Patent No.: US 7,625,872 B2
(45) Date of Patent: *Dec. 1, 2009

(54) BRANCHED IMMUNOMODULATORY COMPOUNDS AND METHODS OF USING THE SAME

(75) Inventor: Karen L. Fearon, Lafayette, CA (US)

(73) Assignee: Dynavax Technologies Corporation, Berkeley, CA (US)

(*) Notice: Subject to any disclaimer, the term of this patent is extended or adjusted under 35 U.S.C. 154(b) by 377 days.

This patent is subject to a terminal disclaimer.

(21) Appl. No.: 10/739,518

(22) Filed: Dec. 17, 2003

(65) Prior Publication Data

US 2004/0136948 A1    Jul. 15, 2004

Related U.S. Application Data

(60) Provisional application No. 60/436,406, filed on Dec. 23, 2002.

(51) Int. Cl.
*A01N 43/04*    (2006.01)
*C12Q 1/68*    (2006.01)
*C12N 15/63*    (2006.01)

(52) U.S. Cl. ............... 514/44; 514/45; 514/48; 514/49; 514/885; 424/1.11; 424/1.73; 424/1.77; 424/278.1; 424/280.1; 536/22.1; 536/23.1; 536/25.6

(58) Field of Classification Search ............... None
See application file for complete search history.

(56) References Cited

U.S. PATENT DOCUMENTS

| | | |
|---|---|---|
| 4,458,066 A | 7/1984 | Caruthers et al. |
| 4,849,513 A | 7/1989 | Smith et al. |
| 4,910,300 A | 3/1990 | Urdea et al. |
| 4,948,882 A | 8/1990 | Ruth |
| 5,015,733 A | 5/1991 | Smith et al. |
| 5,093,232 A | 3/1992 | Urdea et al. |
| 5,118,800 A | 6/1992 | Smith et al. |
| 5,118,802 A | 6/1992 | Smith et al. |
| 5,124,246 A | 6/1992 | Urdea et al. |
| 5,171,264 A | 12/1992 | Merrill et al. |
| 5,359,100 A | 10/1994 | Urdea et al. |
| 5,391,723 A | 2/1995 | Priest |
| 5,453,496 A | 9/1995 | Caruthers et al. |
| 5,460,831 A | 10/1995 | Kossovsky et al. |
| 5,484,596 A | 1/1996 | Hanna, Jr. et al. |
| 5,545,730 A | 8/1996 | Urdea et al. |
| 5,571,677 A | 11/1996 | Gryaznov |
| 5,578,717 A | 11/1996 | Urdea et al. |
| 5,580,731 A | 12/1996 | Chang et al. |
| 5,591,584 A | 1/1997 | Chang et al. |
| 5,594,117 A | 1/1997 | Urdea et al. |
| 5,594,118 A | 1/1997 | Urdea et al. |
| 5,597,909 A | 1/1997 | Urdea et al. |
| 5,614,622 A | 3/1997 | Iyer et al. |
| 5,681,940 A | 10/1997 | Wang et al. |
| 5,703,218 A | 12/1997 | Urdea et al. |
| 5,710,264 A | 1/1998 | Urdea et al. |
| 5,712,378 A | 1/1998 | Wang |
| 5,830,658 A | 11/1998 | Gryaznov |
| 5,849,481 A | 12/1998 | Urdea et al. |
| 5,886,165 A | 3/1999 | Kandimalla et al. |
| 6,077,668 A | 6/2000 | Kool |
| 6,117,657 A | 9/2000 | Usman et al. |
| 6,191,266 B1 | 2/2001 | Wang |
| 6,194,388 B1 | 2/2001 | Krieg et al. |
| 6,207,646 B1 | 3/2001 | Krieg et al. |
| 6,235,465 B1 | 5/2001 | Kolberg et al. |
| 2002/0028784 A1 | 3/2002 | Van Nest |
| 2003/0175731 A1 | 9/2003 | Fearon |

FOREIGN PATENT DOCUMENTS

| | | |
|---|---|---|
| EP | 0 313 219 | 4/1989 |
| IE | 81 267 B | 8/2000 |
| WO | WO 89/02439 | 3/1989 |
| WO | WO 89/03891 | 5/1989 |
| WO | WO 97/28259 | 8/1997 |
| WO | WO 98/16247 | 4/1998 |
| WO | WO 98/55495 | 12/1998 |
| WO | WO 99/11275 | 3/1999 |
| WO | WO 99/62923 | 12/1999 |
| WO | WO 00/61151 | 10/2000 |
| WO | WO 01/22972 | 4/2001 |
| WO | WO 01/35991 | 5/2001 |
| WO | WO 01/68077 | 9/2001 |
| WO | WO 01/68144 | 9/2001 |
| WO | WO-03/057822 A2 | 7/2003 |
| WO | WO-03/057822 A3 | 7/2003 |
| WO | WO-03/057822 C2 | 7/2003 |

OTHER PUBLICATIONS

Klinman et al (1999) Vaccine. 17: 19-25.*

(Continued)

*Primary Examiner*—Gary B. Nickol
*Assistant Examiner*—Michelle Horning
(74) *Attorney, Agent, or Firm*—Morrison & Foerster LLP

(57) ABSTRACT

The invention provides immunomodulatory compounds and methods for immunomodulation of cells and individuals using the immunomodulatory compounds.

2 Claims, 8 Drawing Sheets

OTHER PUBLICATIONS

Winfree et al (1998) Nature. 394:539-544.*
Shchepinov et al (1999) Nucleic Acids Research. 27(15): 3035-3041.*
Yu et al (2001) Bioorganic and Medicinal Chemistry. 9: 2803-2808.*
Liang et al (2000) Journal of Immunology. 165: 1438-1445.*
Yu et al (2002) J. Med. Chem. 45: 4540-4548.*
Yu et al (2002) Nucleic Acids Research 30(20): 4460-4469.*
Grotli et al (1997) Tetrahedron 53(33): 11317-11346.*
Sonehara et al (1996) J. of Interferon and Cytokine Research. 16: 799-803.*
Agrawal, Sudhir et al. (1986). "Efficient Methods for Attaching Non-Radioactive Labels to the 5' ends of Synthetic Oligodeoxyribonucleotides," *Nucleic Acids Res.* 14(15):6227-6245.
Ahmeida, E.T.S. Ben et al. (1993). "Immunopotentiation Local and Systemic Humoral Immune Responses by ISCOMs, Liposomes and FCA: Role In Protection Against Influenza A In Mice," *Vaccine* 11:1302-1309.
Altmann et al. (1995). "NMR Studies of DNA Duplexes Singly Cross-linked by Different Synthetic Linkers," *Nucleic Acids Research* 23:4827-4835.
Aramaki, Yukihito et al. (1995). "Interferon-? inductive Effect of Liposomes as an Immunoadjuvant," *Vaccine* 13:1809-1814.
Asanuma et al. (1995). "Cross-Protection Against Influenza Virus Infection in Mice Vaccinated by Combined Nasal-Subcutaneous Administration," *Vaccine* 13(1):3-5.
Atherton et al. (1981). "Synthesis of a 21-Residue Fragment of Human Proinsulin by the Polyamide Solid Phase Method," *Hoppe Seylers Z. Physiol. Chem.* 362:833-839.
Ballas, Zuhair et al. (1996). "Induction of NK activity in murine and human cells by CpG motifs in oligodeoxynulceotides and bacterial DNA," *J. Immunol.* 157:1840-1845.
Bartley et al. (1997). "Solution Conformation of an Intramolecular DNA Triplex Containing a Nonnucleotide Linker: Comparison with the DNA Duplex," *Biochemistry* 36:14502-14511.
Beaucage. (1993). "Oligodeoxyribonucleotide Synthesis" in Protocols for Oligonucleotides and Analogs, Synthesis and Properties (Agrawal, ed.) Humana Press, Totowa, NJ, pp. 33-61.
Benoit, Robert et al. (1987). "Peptides. Strategies for Antibody Production and Radioimmunoassays," in *Neuromethods*, Alan A. Boulton et al., eds., Humana Press, Clifton, NJ: pp. 43-72.
Bischoff, Rainer et al. (1987). "Introduction of 5'-Terminal Functional Groups into Synthetic Oligonucleotides for Selective Immobilization," *Analytical Biochemistry* 164:336-344.
Blanks et al. (1988). "An Oligodeoxynucleotide Affinity Column for the Isolation of Sequence Specific DNA Binding Proteins," *Nucleic Acids Res.* 16:10283-10299.
Bohle Barbara et al. (1999) "Oligodeoxynucleotides containing CpG Motifs Induce IL-12, IL-18 and IFN-y Production in Cells from Allergic Individuals and Inhibit IgE Synthesis in Vitro," *Eur. J. Immunol.* 29:2344-2353.
Boujrad et al. (1993) "Inhibition of Hormone-Stimulated Steroidogenesis in Cultured Leydig Tumor Cells by a Cholesterol-Linked Phosphorothioate Oligodeoxynucleotide Antisense to Diazepam-Binding Inhibitor," *Biochemistry* 90:5728-5731.
Bousquet et al. (1999). "Molecular Mechanisms of the Adsorption of a Model Protein (Human Serum Albumin) on Poly(Methylidene malonate 2.1.2) Nanoparticles," *Pharm. Res.* 16:141-147.
Braich et al. (1997). "Regiospecific Solid-Phase Synthesis of Branched Oligonucleotides. Effect of Vicinal 2',5'-(or 2',3'-) and 3',5'-Phosphodiester Linkages on the Formation of Hairpin DNA," *Bioconjugate Chem.* 8(3):370-377.
Braun et al. (1988). "Immunogenic Duplex Nucleic Acids are Nuclease Resistant," *J. Immunol.* 141(5):2084-2089.
Breiteneder et al. (1989). "The Gene Coding for the Major Birch Pollen Allergen Betvl, is highly homologous to a Pea Disease Resistance Response Gene," *EMBO J.* 8:1935-1938.
Chaturvedi et al. (1996). "Stabilization of Triple-Stranded Oligonucleotide Complexes: Use of Probes Containing Alternating Phosphodiester and Stereo-Uniform Cationic Phosphoramidate Linkages," *Nucleic Acids Res.* 24(12):2318-2323.

Chavany et al. (1992). "Polyalkylcyanoacrylate Nanoparticles as Polymeric Carriers for Antisense Oligonucleotides," *Pharm. Res.* 9:441-449.
Chavany et al. (1994). "Adsorption of Oligonucleotides onto Polyisohexylcyanoacrylate Nanoparticles Protects Them Against Nucleases and Increases Their Cellular Uptake," *Pharm. Res.* 11:1370-1378.
Chen et al. (1999). "Enhanced Protection Against a Lethal Influenza Virus Challenge by Immunization With Both Hemagglutinin- and Neuraminindase-expressing DNAs," Vaccine 17:653-659.
Cho, Hearn Jay et al. (2000). "Immunostimulatory DNA-Based Vaccines Induce Cytotoxic Lymphocyte Activity by a T-Helper Cell-Independent Mechanism," *Nature Biotechnol.* 18:509-514.
Chua et al. (1988). "Sequence Analysis of cDNA Coding For a Major House Dust Mite Allergen, Der p. 1," *J. Exp. Med.* 167:175-182.
Chua et al. (1990). "Expression of Dermatophagoides Pteronyssinus Allergen, Der p. II, in *Escherichia coli* and the Binding Studies with Human IgE," *Int. Arch. Allergy Appl. Immunol.* 91:124-129.
Cload et al. (1991). "Polyether Tethered Oligonucleotide Probes," *J. Am. Chem. Soc.* 113:6324-6326.
Connolly (1985). "Chemical Synthesis of Oligonucleotides Containing a Free Sulphydryl Group and Subsequent Attachmentof Thiol Specific Probes," *Nucleic Acids Res.* 13:4485-4502.
Connolly (1987). "The Synthesis of Oligonucleotides Containing a Primary Amino Group at the 5'-Terminus," *Nucleic Acids Res.* 15:3131-3139.
Cooke, Sara K. and Sampson, Hugh A. (1997). "Allergenic Properties of Ovomucoid in Man," *J. Immunol.* 159:2026-2032.
Corey et al. (1987). "Generation of a Hybrid Sequence-Specific Single-Stranded Deoxyribonuclease," *Science* 238:1401-1403.
Cowdery et al. (1996). "Bacterial DNA-Induced NK Cell IFN-? to Produce IFN-γ In Vivo and Increases the Toxicity of Lipopolysaccharides," *J. Immunol.* 156:4570-4575.
Czechtizky, W. et al. (2001). "Oligonucleotide Analogues with a Nucleobase-Including Backbone: 2-Deoxy-D-erythrose-Derived Phosphoramidites: Synthesis and Incorporation into 14-Mer DNA Strands," *Helv. Chim. Acta* 84:1000-1016.
Dagneaux et al. (1996). "Parallel and Antiparallel AA-T Intramolecular Triple Helices," *Nucleic Acids Research* 24:4506-4512.
Damha et al. (1988). "Synthesis and Spectroscopic Analysis of Branched RNA Fragments: Messenger RNA Splicing Intermediates," *J. Org. Chem* 53:3710-3722.
Damha et al. (1989). "Automated Solid-Phase Synthesis of Branched Oligonucleotides," *Tetrahedron Lett.* 30(46):6295-6298.
Damha et al. (1992). "Solid-Phase Synthesis of Branched Oligoribonucleotides Related to Messenger RNA Splicing Intermediates," *Nucleic Acids Res.* 20(24):6565-6573.
de Martino et al. (1999). "Low IgG3 and high IgG4 subclass levels in children with advanced human immunodeficiency virus-type 1 infection and elevated IgE levels," *Ann. Allergy Asthma Immunol.* 83:160-164.
Deshmukh et al. (2000). "Process Development for Purification of Therapeutic Antisense Oligonucleotides by Anion-Exchange Chromatography," *Organic Process Research & Development* 4(3):205-213.
Douglas et al. (1987). "Nanoparticles in Drug Delivery," *Crit. Rev. Ther. Drug. Carrier Syst.* 3:233-261.
Durand et al. (1990). "Circular Dichroism Studies of an Oligodeoxyribonucleotide Containing a Hairpin Loop Made of a Hexathylene Glycol Chain: Conformation and Stability," *Nucleic Acids Research* 18:6353-6359.
Elsayed et al. (1991). "The Structural Requiements of Epitopes With IgE Binding Capacity Demonstrated by Three Major Allergens From Fish, Egg and Tree Pollen," *Scand. J. Clin. Lab. Invest.* Suppl. 204:17-31.
Fensholdt et al. (1996). "Synthesis of Diastereomeric Mixtures of 5'-C-Hydroxymethylthmidine and Introduction of a Novel Class of C-Hydroxymethyl Functionalised Oligodeoxynucleotides," *Acta Chem Scand.* 50:1157-1163.
Fornadley. (1998). "Allergy Immunotherapy," *Otolaryngol. Clin. North Am.* 31:111-127.

Galland, A.V. et al. (1998). "Purification of a 41 kDa Cod-Allergenic Protein," *J. Chromatogr. B*. 706:63-71.

Gao et al. (1995). "Circularization of Oligonucleotides by Disulfide Bridge Formation," *Nucleic Acids Res*. 23(11):2025-2029.

Gennaro, Alfonso R., ed. (1990). *Remington's Pharmaceutical Sciences*, 18th Edition, Mack Publishing Company: pp. xv-xvi.

Geoghegan et al. (1992). "Site-Directed Conjugation of Nonpeptide Groups to Peptides and Proteins via Periodate Oxidation of a 2-Amino Alcohol. Application to Modification at N-Terminal Serine," *Bioconjug. Chem*. 3:138-146.

Gnanou et al. (1988). "Synthesis of Star-shaped Poly(ethylene oxide)," *Makromol. Chem*. 189:2885-2892.

Godard, Gérard et al. (1995). "Antisense Effects of Cholesterol-Oligodeoxynucleotide Conjugates Associated with Poly(Alkylcyanoacrylate) Nanoparticles," *Eur. J. Biochem*. 232:404-410.

Govorkova, E.A. and Smirnov, Yu. A. (1997). "Cross-Protection of Mice Immunized with Different Influenza A (H2) Strains and Challenged with Viruses of the Same HA Subtype," *Acta Virol*. 41:251-257.

Grabarek, Zenon and Gergely, John (1990). "Zero-Length Crosslinking Procedure with the Use of Active Esters," *Anal. Biochem*. 185:131-135.

Granoff et al. (1993). "Effect of Immunity to the Carrier Protein on Antibody Responses to Haemophilus Influenzae Type b Conjugate Vaccines," *Vaccine* 11:Suppl.1 :46-51.

Hagiwara, Akeo and Takahashi, Toshio et al. (1987). "A New Drug-Delivery-System of Anticancer Agents: Activated Carbon Particles Adsorbing Anticancer Agents," *In Vivo* 1:241-252.

Hames, B.D. and Higgins, S.J., eds. (1987). *Transcription and Translation A Practical Approach*, IRL Press: pp. vii-xiv (Table of Contents).

Haralambidis et al. (1990a). "The Synthesis of Polyamide—Oligonucleotide Conjugate Molecules," *Nucleic Acids Res*. 18:493-499.

Haralambidis et al. (1990b). "The Preparation of Polyamide-Oligonucleotide Probes Containing Multiple Non-radioactive Labels," *Nucleic Acids Res*. 18:501-505.

Hendry et al. (1994). "Using Linkers to Investigate the Spatial Separation of the Conserved Nucleotides $A_9$ and $G_{12}$ in the Hammerhead Ribozyme," *Biochemica et Biophysica Acta* 1219:405-412.

Horn et al. (1989). "Forks and Combs and DNA: the Synthesis of Branched Oligodeoxyribonucleotides," *Nucleic Acids Res*. 17(17):6959-6967.

Horn, T. et al. (1997). "An Improved Divergent Synthesis of Comb-type Branched Oligodeoxyribonucleotides (bDNA) Containing Multiple Secondary Sequences," *Nucleic Acids Res*. 25(23):4835-4841.

Horn, T. et al. (1997). "Chemical Synthesis and Characterization of Branched Oligodeoxyribonucleotides (bDNA) for Use as Signal Amplifiers in Nucleic Acid Quantification Assays," *Nucleic Acids Res*. 25(23):4842-4849.

Hudson, H.E. et al. (1993). "The Synthesis of Branched Nucleic Acids Has Been Extended to the Synthesis of Nucleic Acid Dendrimers," *J. Am. Chem. Soc*. 115:2119-2124.

Iyer et al. (1990). "The Automated Synthesis of Sulfur-Containing Oligodeoxyribonucleotides Using 3H-1,2-Benzodithiol-3-one 1,1-Dioxide as a Sulfur-Transfer Reagent," *J. Org. Chem*. 55(15):4693-4699.

Jager et al. (1988). "Oligonucleotide N-Alkylphosphoramidates: Synthesis and Binding to Polynucleotides," *Biochem*. 27:7237-7246.

Jaschke et al. (1993). "Automated Incorporation of Polyethylene Glycol into Synthetic Oligonucleotides," *Tetrahedron Lett*. 34(2):301-304.

Jørgensen, P.N. et al. (1995). "Incorporation of 3'-C-(Hydroxymethyl)thymidine into Novel Oligodeoxynucleotide Analogues," *Tetrahedron* 51(7):2155-2164.

Jørgensen, P.N. et al. (1994). "Synthesis of 3'-C-(Hydroxymethyl)thymidine: Introduction of a Novel Class of Deoxynucleosides and Oligodexoynucleotides," *J. Am Chem. Soc*. 116:2231-2232.

Kandimalla et al. (2001). "Effect of Chemical Modifications of Cytosine and Guanine in a CpG-Motif of Oligonucleotides: Structure-Immunostimulatory Activity Relationships," *Bioorg. Med. Chem*. 9:807-813.

Kessler, Christoph (1992). "Nonradioactive Labeling Methods for Nucleic Acids," Chapter 2 in *Nonisotopic DNA Probe Techniques*, Larry J. Kricka, ed., Academic Press, Inc.: pp. 29-92.

Kierzek, R. et al. (1986). "Chemical Synthesis of Branched RNA," *Nucleic Acids Res*. 14(12):4751-4764.

Kikuta et al. (1990) "Cross-protection against influenza B type virus infection by intranasal inoculation of the HA vaccines combined with cholera toxin B subunit," *Vaccine* 8:595-599.

Kingetsu, I. et al. (2000). "Common Antigenicity Between Japanese Cedar (*Cryptomeria japonica*) Pollen and Japanese Cypress (*Chamaecyparis obtusa*) Pollen, I. H-2 Complex Affects Cross Responsiveness to Cry j 1 and Cha o 1 at the T- and B-cell level in Mice," *Immunol*. 99:625-629.

Klinman et al. (1997). "Contribution of CpG Motifs to the Immunogenicity of DNA Vaccines," *J. Immunol*. 158:3635-3639.

Kodihalli et al. (1997). "Cross-Protection Among Lethal H5N2 Influenza Viruses Induced by DNA Vaccine to the Hemagglutinin," *J. Virol*. 71:3391-3396.

Kremsky et al. (1987). "Immobilization of DNA via Oligonucleotides Containing an Aldehyde or Carboxylic Acid Group at the 5' Terminus," *Nucleic Acids Res*. 15:2891-2909.

Krieg et al. (1995). "CpG Motifs in Bacterial DNA Trigger Direct B-Cell Activation," *Nature* 374:546-549.

Kullman, Willi. *Enzymatic Peptide Synthesis*, CRC Press, Inc. Boca Raton, FL: (Table of Contents), Published May 1987.

Lambert et al. (1998). "Effect of Polyisobutylcyanoacrylate nanoparticles and Lipofectin® Loaded with Oligonucleotides on Cell Viability and a PKC Alpha Neosynthesis in HepG2 Cells," *Biochimie* 80:969-976.

Lasic, D.D. (1993). *Liposomes: From Physics to Applications*, Elsevier, Amsterdam: pp. xi-xviii (Table of Contents).

Latimer et al. (1995). "Specificity of Monoclonal Antibodies Produced Against Phosphorothioate and Ribo Modified DNAs," *Mol. Immunol*. 32(14/15):1057-1064.

Lea et al. (1996). "Cloning and Sequencing of cDNA's Encoding the Human Sperm Protein Sp17," *Biochem. Biophys. Acta* 1307:263-266.

Lipford et al. (1997a). "CpG-Containing Synthetic Oligonucleotides Promote B and Cytotoxic T Cell Responses to Protein Antigen: A New Class of Vaccine Adjuvants," *Eur. J. Immunol*. 27:2340-2344.

Lyttle et al. (2002). "New Reagents and Methods for the Synthesis of Internal and 3'-Labeled DNA," *Bioconjugate Chem*. 13:1146-1154.

Ma et al. (1993). "Design and Synthesis of RNA Miniduplexes via a Synthetic Linker Approach. 2. Generation of Covalently Closed, Double-Stranded Cyclic HIV-1 TAR RNA Analogs with High Tat-Binding Affinity," *Nucleic Acids Research* 21(11):2585-2589.

Ma et al. (1993). "Design and Synthesis of RNA Miniduplexes via a Synthetic Linker Approach," *Biochemistry* 32(7):1751-1758.

Matteucci. (1997). "Oligonucleotide Analogs: an Overview" in *Oligonucleotides as Therapeutic Agents*, (D.J. Chadwick and G. Cardew, ed.) John Wiley and Sons, New York, NY, pp. 5-18.

Mbawuike et al. (1994). "Influenza A Subtype Cross-Protection After Immunization of Outbred Mice with a Purified Chimeric NS1/HA2 Influenza Virus Protein," *Vaccine* 12:1340-1348.

McCurdy et al. (1991). "Deoxyoligonucleotides with Inverted Polarity: Synthesis and Use in Triple-Helix Formation," *Nucleosides & Nucleotides* 10(1-3):287-290.

Medical Economics Company, Inc. (1998). *Physicians' Desk Reference*. 52nd edition, Medical Economics Company: Montvale, NJ. 2 pages. (Table of Contents).

Miller et al. (1971). "Syntheses and Properties of Adenine and Thymine Nucleoside Alkyl Phosphotriesters, the Neutral Analogs of Dinucleoside Monophosphates," *JACS* 93(24):6657-6665.

Mishell; Barbara B. and Shiigi, Stanley M., eds. *Selected Methods in Cellular Immunology*, W.H. Freeman & Co., San Francisco: pp. vii-xiv (Table of Contents), Published, Mar. 1980.

Mitragotri et al. (1995). "Ultrasound-Mediated Transdermal Protein Delivery," *Science* 269:850-853.

Nelson et al. (1989) "Bifunctional Oligonucleotide Probes Synthesized Using a Novel CPG Support are able to Detect Single Base Pair Mutations," *Nucleic Acids Research* 17:7187-7195.

Nelson et al. (1996). "Incorporation of a Non-Nucleotide Bridge into Hairpin Oligonucleotides Capable of High-Affinity Binding to the Rev Protein of HIV-1," *Biochemistry* 35:5339-5944.

Nelson et al. (1997). "N3'->P5' Oligodeoxyribonucleotide Phosphoramidates: A New Method of Synthesis Based on a Phosphoramidite Amine-Exchange Reaction," *JOC* 62(21):7278-7287.

O'Shannessy et al. (1985). "Specific Conjugation Reactions of the Oligosaccharide Moieties of Immunoglobulins," *J. Applied Biochem.* 7:347-355.

Ono et al. (1991). "DNA Triplex Formation of Oligonucleotide Analogues Consisting of Linker Groups and Octamer Segments That Have Opposite Sugar-Phosphate Backbone Polarities," *Biochemistry* 30(41):9914-9921.

Pastorello, Elide A. et al. (1998). "Sensitization to the Major Allergen of Brazil Nut is Correlated with the Clinical Expression of Allergy," *J. Allergy Clin. Immunol.* 102(6):1021-1027.

Pertmer et al. (1996). "Influenza Virus Nucleoprotein-Specific Immunoglobulin G Subclass and Cytokine Responses Elicited by DNA Vaccination are Dependent on the Route of Vector DNA Delivery," *J. Virol.* 70:6119-6125.

Peyrottes et al. (1996). "Oligodeoxynucleoside Phosphoramidates (P-NH$_2$): Synthesis and Thermal Stability of Duplexes with DNA and RNA Targets," *Nucleic Acids Res.* 24(10):1841-1848.

Pfundheller et al. (2000). "Oligonucleotides Containing Novel 4'-C- or 3'-C- (Aminoalkyl)-Branched Thymidines," *Helvetica Chimica Acta* 83:128-151.

Pichyangkul et al. (2001) *J. Imm. Methods* 247:83-94.

Pisetsky (1996a). "The Immunologic Properties of DNA," *J. Immunol.* 156:421-423.

Polushin, N.N. (1999). "Synthesis of Highly Functionalized Oligonucleotides Using Novel Modifying and Branching Phosphoramidite Units," *Collection Symposium Series* 2:145-150.

Rafnar et al. (1991). "Cloning of Amb a I (Antigen E), the Major Allergen Family of Short Ragweed Pollen," *J. Biol. Chem.* 266:1229-1236.

Raz et al. (1994). "Intradermal gene immunization: The possible role of DNA uptake in the induction of cellular immunity to viruses," *Proc. Natl. Acad. Sci. USA* 91:9519-9523.

Reese, Gerald et al. (1997). "Characterization of Recombinant Shrimp Allergen Pen a 1 (Tropomyosin)," *Int. Arch. Allergy Immunol.* 113:240-242.

Rein et al. (1993). "New Developments in Synthesis of Star Polymers with Poly(ethylene oxide) Arms," *Acta Polymer* 44:225-229.

Reynolds et al. (1996). "Antisense Oligonucleotides Containing an Internal, Non-nucleotide-based Linker Promote Site-Specific Cleavage of RNA," *Nucleic Acids Research* 24(4):760-765.

Richardson et al. (1991). "Tethered Oligonucleotide Probes. A Strategy for the Recognition of Structured RNA," *J. Am. Chem. Soc.* 113:5109-5111.

Rogers et al. (1993). "Recombinant Fel d I: Expression, Purification, IgE Binding and Reaction with Cat-Allergic Human T Cells," *Mol. Immunol.* 30:559-568.

Roget et al. (1989). "Synthesis and Use of Labelled Nucleoside Phosphoramidite Building Blocks Bearing a Reporter Group: Biotinyl, Dinitrophenyl, Pyrenyl and Dansyl," *Nucleic Acids Res.* 17:7643-7651.

Romagnani. (2000). "T-Cell Subsets (Th1 versus Th2)," *Ann. Allergy Asthma Immunol.* 85:9-18.

Roman et al., (1997)."Immunostimulatory DNA sequences function as T helper-1-promoting adjuvants" *Nature Medicine* 3:849-854.

Salunkhe et al. (1992). "Control of Folding and Binding of Oligonucleotides by Use of a Nonnucleotide Linker," *J. Am. Chem. Soc.*114(23):8768-8777.

Sato et al., "Immunostimulatory DNA sequences necessary for effective intradermal gene immunization," (1996) *Science* 273:352-354.

Scherle and Gerhard (1986). "Differential Ability of B Cells Specific for External vs. Internal Influenza Virus Proteins to Respond to Help from Influenza Virus-Specific T-cell clones in vivo," *J. Exp. Med.* 164:1114-1128.

Scherle and Gerhard (1988). "Functional Analysis of Influenza-Specific Helper T Cell Clones In Vivo," *Proc. Natl. Acad. Sci. USA* 85:4446-4450.

Schroeder et al. (1998). "Efficacy of Oral Dalargin-loaded Nanoparticle Delivery Across the Blood-Brain Barrier," *Peptides* 19:777-780.

Schultz et al. (1996). "Oligo-2'-fluoro-2'-deoxynucleotide N3'→P5' Phosphoramidates: Synthesis and Properties," *Nucleic Acids Res.* 24(15):2966-2973.

Sélo, I. et al. (1999). "Allergy to Bovine β-Lactoglobulin: Specificity of Human IgE to Tryptic Peptides," *Clin. Exp. Allergy* 29:1055-1063.

Shchepinov, M.S. (1999). "Oligonucleotide Dendrimers: Stable Nano-Structures," *Nucleic Acids Res.* 27(15):3035-41.

Shchepinov, M.S. (2002). "Oligonucleotide Dendrimers: From Poly-Labelled DNA Probes to Stable Nano-Structures," *Glen Research Glen Report* located at <http://www.glenresearch.com/glenreports/GR12-11.html> visited on Dec. 4, 2002. (8 pages).

Shimada et al. (1986). "In Vivo Augmentation of Natural Killer Cell Activity with a Deoxyribonucleic Acid Fraction of BCG," *Jpn. J. Cancer Res.* 77:808-816.

Sinah, Nanda D. and Striepeke, Steve (1991). "Oligonucleotides with Reporter Groups Attached to the 5'-Terminus," Chapter 8 in *Oligonucleotide Analogues: A Practical Approach*, F. Eckstein, ed., IRL Press: pp. 185-210.

Sowka, Slawomir et al. (1998). "cDNA Cloning of the 43-kDa Latex Allergen Hev b 7 with Sequence Similarity to Patatins and its Expression in the Yeast *Pichia pastoris*," *Eur. J Biochem.* 255:213-219.

Sproat, B.S. et al. (1994). "Novel Solid-phase Synthesis of Branched Oligoribonucleotides, including a Substrate for the RNA Debranching Enzyme," *J. Chem. Soc. Perkin Trans. 1.* 4:419-431.

Stanley, J.S. et al. (1996). "Peanut Hypersensitivity: IgE Binding Characteristics of a Recombinant Ara h 1 Protein," *Adv. Exp. Med. Biol.* 409:213-216.

Staros et al., (1986) "Enhancement by N-Hydroxysulfosucciniminde of Water-Soluble Carbodiimide-Mediated Coupling Reactions," *Analytical Biochemistry* 156, pp. 220-222.

Stirchak et al. (1989). "Uncharged Steroregular Nucleic Acid Analogs: 2. Morpholino Nucleoside Oligomers with Carbamate Internucleoside Linkages," *Nucleic Acids Res.* 17(15):6129-6141.

Takahashi et al. (1990). "Induction of CD8+ cytotoxic T Cells by Immunization with Purified HIV-1 Envelope Protein in ISCOMs," *Nature* 344:873-875.

Tamborini, Elena et al. (1997). Biochemical and Immunological Characterization of Recombinant Allergen Lol p 1, *Eur. J. Biochem.* 249:886-894.

Tamura et al. (1992). "Superior Cross-Protective Effect of Nasal Vaccination to Subcutaneous Inoculation with Influenza Hemagglutinin Vaccine," *Eur. J. Immunol.* 22:477-481.

Tamura et al. (1994). "Formulation of Inactivated Influenza Vaccines for Providing Effective Cross-Protection by Intranasal Vaccination in Mice," *Vaccine* 12:310-316.

Tang et al. (2000). "Large-Scale Synthesis of Oligonucleotide Phosphorothioates Using 2-Amino-1,2,4-Dithiazole-5-Thione as an Efficient Sulfur-Transfer Reagent," *Org. Process Res. Dev.* 4(3):194-198.

Teuber, Suzanne S. et al. (1998). "Cloning and Sequencing of a Gene Encoding a 2S Albumin Seed Storage Protein Precursor from English Walnut (*Juglans regia*), a Major Food Allergen," *J. Allergy Clin. Immun.* 101:807-814.

Kendrew, J. (ed). (1994). *The Encyclopedia of Molecular Biology*, Table of Contents, Blackwell Science, pp. vi-viii.

Thrane, H. et al. (1995). "Novel Linear and Branched Oligodeoxynucleotide Analogues Containing 4'-C-(Hydroxymethyl)thymidine," *Tetrahedron* 51(37):10389-10402.

Tung et al. (1991). "Preparation of Oligonucleotide-Peptide Conjugates," *Bioconjug. Chem.* 2:464-465.

Van Do, T. et al. (1999). "Expression and Analysis of Recombinant Salmon Parvalbumin, the Major Allergen in Atlantic Salmon (*Salmo salar*)," *Scand. J. Immunol.* 50:619-625.

Verthelyi, Daniela et al. (2001). "Human Peripheral Blood Cells Differentially Recognize and Respond to Two Distinct CpG Motifs," *J. Immunol.* 166(4):2372-2377.

Von Büren, M. et al. (1995). "Branched Oligodeoxynucleotides: Automated Synthesis and Tripe Helical Hybridization Studies," *Tetrahedron* 51(31):8491-8506.

Wang et al. (1994). "Circular RNA Oligonucleotides. Synthesis, Nucleic Acid Binding Properties, and a Comparison with Circular DNAs," *Nucleic Acids Res.* 22(12):2326-2333.

Warner et al. (1984). "Construction and Evaluation of an Instrument for the Automated Synthesis of Oligodeoxyribonucleotides," *DNA* 3(5):401-411.

Watwe et al. (1995). "Manufacture of Liposomes: A Review," *Curr. Sci.* 68:715-724.

Widhe et al., (1998). "IgG Subclasses in Lyme Borreliosis: A Study of Specific IgG Subclass Distribution in a Interferon-y-Predominated Disease," *Scand. J. Immunol* 47: 575-581.

Wyrzykiewica et al. (1994). "Efficiency of Sulfurization in the Synthesis of Oligodeoxyribonucleotide Phosphorothioates Utilizing Various Sulfurizing Reagents," *Bioorg. & Med. Chem. Lett.* 4(12):1519-1522.

Yamamoto, Saburo et al. (1992). "Unique Palindromic Sequences in Synthetic Oligonucleotides are Required to Induce IFN [correction of INF] and Augment IFN-Mediated [correction of INF] Natural Killer Activity," *J. Immunol.* 148(12):4072-4076.

Yanagawa et al. (1988). "Analysis of Superhelical Structures of Nucleic Acid-Lipid Conjugates by Image Processing," *Nucleic Acids Symp. Ser.* 19:189-192.

Zon. (1993) "Oligonucleoside Phosphorothioates" in *Protocols for Oligonucleotides and Analogs, Synthesis and Properties* (Agrawal, ed.) Humana Press, pp. 165-190.

Zuckermann et al. (1987). "Efficient Methods for Attachment of Thiol Specific Probes to the 3'-Ends of Synthetic Oligodeoxyribonucleotides," *Nucleic Acids Res.* 15:5305-5321.

Chedid, L. et al. (Dec. 1979). "Enhancement of Certain Biological Activities of Muramyl Dipeptide Derivatives after Conjugation to a Multi-poly(DL-alanine)—poly(L-ly sine) Carrier," *Proceedings of the National Academy of Sciences of the United States of America* 76(12):6557-6561.

Supplementary European Search Report mailed on May 16, 2008, for European Patent Application No. 03811673.7, flied on Dec. 17, 2003, four pages.

* cited by examiner

1A

1B

1C

1D

1E

After annealing in the presence of salt

SEQUENCE LISTING

```
<160> NUMBER OF SEQ ID NOS: 148

<210> SEQ ID NO 1
<211> LENGTH: 18
<212> TYPE: DNA
<213> ORGANISM: Artificial Sequence
<220> FEATURE:
<223> OTHER INFORMATION: Synthetic Construct

<400> SEQUENCE: 1
ttggccaagc ttggccaa                                                       18

<210> SEQ ID NO 2
<211> LENGTH: 12
<212> TYPE: DNA
<213> ORGANISM: Artificial Sequence
<220> FEATURE:
<223> OTHER INFORMATION: Synthetic Construct

<400> SEQUENCE: 2
ctgaacgttc ag                                                             12

<210> SEQ ID NO 3
<211> LENGTH: 22
<212> TYPE: DNA
<213> ORGANISM: Artificial Sequence
<220> FEATURE:
<223> OTHER INFORMATION: Synthetic Construct

<400> SEQUENCE: 3
tgactgtgaa ccttagagat ga                                                  22
```

<210> SEQ ID NO 4
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = T, G, C or B (B is 5-bromocytosine)
<220> FEATURE:
<221> NAME/KEY: misc_feature
<222> LOCATION: 4
<223> OTHER INFORMATION: n = T, A, or C

<400> SEQUENCE: 4 ndancgktcg                                                          10

<210> SEQ ID NO 5
<211> LENGTH: 10
<212> TYPE: DNA
<213> ORGANISM: Artificial Sequence
<220> FEATURE:
<223> OTHER INFORMATION: Synthetic Construct

<400> SEQUENCE: 5
tgaacgttcg                                                          10

<210> SEQ ID NO 6
<211> LENGTH: 10
<212> TYPE: DNA
<213> ORGANISM: Artificial Sequence
<220> FEATURE:
<223> OTHER INFORMATION: Synthetic Construct

<400> SEQUENCE: 6
ggaacgttcg                                                          10

<210> SEQ ID NO 7
<211> LENGTH: 10
<212> TYPE: DNA
<213> ORGANISM: Artificial Sequence
<220> FEATURE:
<223> OTHER INFORMATION: Synthetic Construct

<400> SEQUENCE: 7
tgaacgutcg                                                          10

<210> SEQ ID NO 8
<211> LENGTH: 10
<212> TYPE: DNA
<213> ORGANISM: Artificial Sequence
<220> FEATURE:
<223> OTHER INFORMATION: Synthetic Construct

<400> SEQUENCE: 8
tgaccgttcg                                                          10

<210> SEQ ID NO 9
<211> LENGTH: 10
<212> TYPE: DNA
<213> ORGANISM: Artificial Sequence
<220> FEATURE:
<223> OTHER INFORMATION: Synthetic Construct

<400> SEQUENCE: 9

```
tgatcggtcg                                                              10

<210> SEQ ID NO 10
<211> LENGTH: 10
<212> TYPE: DNA
<213> ORGANISM: Artificial Sequence
<220> FEATURE:
<223> OTHER INFORMATION: Synthetic Construct

<400> SEQUENCE: 10
tgatcgttcg                                                              10

<210> SEQ ID NO 11
<211> LENGTH: 10
<212> TYPE: DNA
<213> ORGANISM: Artificial Sequence
<220> FEATURE:
<223> OTHER INFORMATION: Synthetic Construct

<400> SEQUENCE: 11
tgaacggtcg                                                              10

<210> SEQ ID NO 12
<211> LENGTH: 10
<212> TYPE: DNA
<213> ORGANISM: Artificial Sequence
<220> FEATURE:
<223> OTHER INFORMATION: Synthetic Construct

<400> SEQUENCE: 12
gtaacgttcg                                                              10

<210> SEQ ID NO 13
<211> LENGTH: 10
<212> TYPE: DNA
<213> ORGANISM: Artificial Sequence
<220> FEATURE:
<223> OTHER INFORMATION: Synthetic Construct

<400> SEQUENCE: 13
gtatcggtcg                                                              10

<210> SEQ ID NO 14
<211> LENGTH: 10
<212> TYPE: DNA
<213> ORGANISM: Artificial Sequence
<220> FEATURE:
<223> OTHER INFORMATION: Synthetic Construct

<400> SEQUENCE: 14
gtaccgttcg                                                              10

<210> SEQ ID NO 15
<211> LENGTH: 10
<212> TYPE: DNA
<213> ORGANISM: Artificial Sequence
<220> FEATURE:
<223> OTHER INFORMATION: Synthetic Construct

<400> SEQUENCE: 15
gaaccgttcg                                                              10

<210> SEQ ID NO 16
<211> LENGTH: 10
<212> TYPE: DNA
<213> ORGANISM: Artificial Sequence
```

```
<220> FEATURE:
<223> OTHER INFORMATION: Synthetic Construct

<400> SEQUENCE: 16 bgaccgttcg                                                                          10

<210> SEQ ID NO 17
<211> LENGTH: 10
<212> TYPE: DNA
<213> ORGANISM: Artificial Sequence
<220> FEATURE:
<223> OTHER INFORMATION: Synthetic Construct

<400> SEQUENCE: 17
cgaacgttcg                                                                          10

<210> SEQ ID NO 18
<211> LENGTH: 10
<212> TYPE: DNA
<213> ORGANISM: Artificial Sequence
<220> FEATURE:
<223> OTHER INFORMATION: Synthetic Construct

<400> SEQUENCE: 18
cgaccgttcg                                                                          10

<210> SEQ ID NO 19
<211> LENGTH: 10
<212> TYPE: DNA
<213> ORGANISM: Artificial Sequence
<220> FEATURE:
<223> OTHER INFORMATION: Synthetic Construct

<400> SEQUENCE: 19 bgaacgttcg                                                                          10

<210> SEQ ID NO 20
<211> LENGTH: 10
<212> TYPE: DNA
<213> ORGANISM: Artificial Sequence
<220> FEATURE:
<223> OTHER INFORMATION: Synthetic Construct

<400> SEQUENCE: 20
ttaacgutcg                                                                          10

<210> SEQ ID NO 21
<211> LENGTH: 10
<212> TYPE: DNA
<213> ORGANISM: Artificial Sequence
<220> FEATURE:
<223> OTHER INFORMATION: Synthetic Construct

<400> SEQUENCE: 21
tuaacgutcg                                                                          10

<210> SEQ ID NO 22
<211> LENGTH: 10
<212> TYPE: DNA
<213> ORGANISM: Artificial Sequence
<220> FEATURE:
<223> OTHER INFORMATION: Synthetic Construct

<400> SEQUENCE: 22
ttaacgttcg                                                                          10
```

<210> SEQ ID NO 23
<211> LENGTH: 24
<212> TYPE: DNA
<213> ORGANISM: Artificial Sequence
<220> FEATURE:
<223> OTHER INFORMATION: Synthetic Construct

<400> SEQUENCE: 23
tcgtcgaacg ttcgttaacg ttcg                                          24

<210> SEQ ID NO 24
<211> LENGTH: 22
<212> TYPE: DNA
<213> ORGANISM: Artificial Sequence
<220> FEATURE:
<223> OTHER INFORMATION: Synthetic Construct

<400> SEQUENCE: 24
tgactgtgaa cgutcgagat ga                                            22

<210> SEQ ID NO 25
<211> LENGTH: 24
<212> TYPE: DNA
<213> ORGANISM: Artificial Sequence
<220> FEATURE:
<223> OTHER INFORMATION: Synthetic Construct

<400> SEQUENCE: 25
tcgtcgaucg utcgttaacg utcg                                          24

<210> SEQ ID NO 26
<211> LENGTH: 24
<212> TYPE: DNA
<213> ORGANISM: Artificial Sequence
<220> FEATURE:
<223> OTHER INFORMATION: Synthetic Construct

<400> SEQUENCE: 26
tcgtcgaucg ttcgtuaacg utcg                                          24

<210> SEQ ID NO 27
<211> LENGTH: 24
<212> TYPE: DNA
<213> ORGANISM: Artificial Sequence
<220> FEATURE:
<223> OTHER INFORMATION: Synthetic Construct

<400> SEQUENCE: 27
tcgtcguacg utcgttaacg utcg                                          24

<210> SEQ ID NO 28
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 8
<223> OTHER INFORMATION: n = 2-amino-adenine

<400> SEQUENCE: 28
tcgtcganac gutcgttaac gutcg                                         25

<210> SEQ ID NO 29
<211> LENGTH: 24

```
<212> TYPE: DNA
<213> ORGANISM: Artificial Sequence
<220> FEATURE:
<223> OTHER INFORMATION: Synthetic Construct

<400> SEQUENCE: 29
tgatcgaacg ttcgttaacg ttcg                                           24

<210> SEQ ID NO 30
<211> LENGTH: 22
<212> TYPE: DNA
<213> ORGANISM: Artificial Sequence
<220> FEATURE:
<223> OTHER INFORMATION: Synthetic Construct

<400> SEQUENCE: 30
tgactgtgaa cgutcggtat ga                                             22

<210> SEQ ID NO 31
<211> LENGTH: 22
<212> TYPE: DNA
<213> ORGANISM: Artificial Sequence
<220> FEATURE:
<223> OTHER INFORMATION: Synthetic Construct

<400> SEQUENCE: 31
tgactgtgac cgttcggtat ga                                             22

<210> SEQ ID NO 32
<211> LENGTH: 22
<212> TYPE: DNA
<213> ORGANISM: Artificial Sequence
<220> FEATURE:
<223> OTHER INFORMATION: Synthetic Construct

<400> SEQUENCE: 32
tgactgtgat cggtcggtat ga                                             22

<210> SEQ ID NO 33
<211> LENGTH: 16
<212> TYPE: DNA
<213> ORGANISM: Artificial Sequence
<220> FEATURE:
<223> OTHER INFORMATION: Synthetic Construct

<400> SEQUENCE: 33
tcgtcgaacg ttcgtt                                                    16

<210> SEQ ID NO 34
<211> LENGTH: 22
<212> TYPE: DNA
<213> ORGANISM: Artificial Sequence
<220> FEATURE:
<223> OTHER INFORMATION: Synthetic Construct

<400> SEQUENCE: 34
tcgtcgtgaa cgttcgagat ga                                             22

<210> SEQ ID NO 35
<211> LENGTH: 22
<212> TYPE: DNA
<213> ORGANISM: Artificial Sequence
<220> FEATURE:
<223> OTHER INFORMATION: Synthetic Construct

<400> SEQUENCE: 35
```

```
tcgtcggtat cggtcggtat ga                                              22
```

<210> SEQ ID NO 36
<211> LENGTH: 18
<212> TYPE: DNA
<213> ORGANISM: Artificial Sequence
<220> FEATURE:
<223> OTHER INFORMATION: Synthetic Construct

<400> SEQUENCE: 36

```
cttcgaacgt tcgagatg                                                   18
```

<210> SEQ ID NO 37
<211> LENGTH: 18
<212> TYPE: DNA
<213> ORGANISM: Artificial Sequence
<220> FEATURE:
<223> OTHER INFORMATION: Synthetic Construct

<400> SEQUENCE: 37

```
ctgtgatcgt tcgagatg                                                   18
```

<210> SEQ ID NO 38
<211> LENGTH: 22
<212> TYPE: DNA
<213> ORGANISM: Artificial Sequence
<220> FEATURE:
<223> OTHER INFORMATION: Synthetic Construct

<400> SEQUENCE: 38

```
tgactgtgaa cggtcggtat ga                                              22
```

<210> SEQ ID NO 39
<211> LENGTH: 22
<212> TYPE: DNA
<213> ORGANISM: Artificial Sequence
<220> FEATURE:
<223> OTHER INFORMATION: Synthetic Construct

<400> SEQUENCE: 39

```
tcgtcggtac cgttcggtat ga                                              22
```

<210> SEQ ID NO 40
<211> LENGTH: 22
<212> TYPE: DNA
<213> ORGANISM: Artificial Sequence
<220> FEATURE:
<223> OTHER INFORMATION: Synthetic Construct

<400> SEQUENCE: 40

```
tcgtcggaac cgttcggaat ga                                              22
```

<210> SEQ ID NO 41
<211> LENGTH: 19
<212> TYPE: DNA
<213> ORGANISM: Artificial Sequence
<220> FEATURE:
<223> OTHER INFORMATION: Synthetic Construct

<400> SEQUENCE: 41

```
tcgtcgaacg ttcgagatg                                                  19
```

<210> SEQ ID NO 42
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 42
tcgtcgtaac gttcgagatg                                              20

<210> SEQ ID NO 43
<211> LENGTH: 22
<212> TYPE: DNA
<213> ORGANISM: Artificial Sequence
<220> FEATURE:
<223> OTHER INFORMATION: Synthetic Construct

<400> SEQUENCE: 43
tgactgtgac cgttcggaat ga                                           22

<210> SEQ ID NO 44
<211> LENGTH: 22
<212> TYPE: DNA
<213> ORGANISM: Artificial Sequence
<220> FEATURE:
<223> OTHER INFORMATION: Synthetic Construct

<400> SEQUENCE: 44
tcgtcgaacg ttcgaacgtt cg                                           22

<210> SEQ ID NO 45
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5
<223> OTHER INFORMATION: b is 5-bromocytosine

<400> SEQUENCE: 45
tbgtbgaacg ttcgagatg                                               19

<210> SEQ ID NO 46
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 46
tcgtbgaacg ttcgagatg                                               19

<210> SEQ ID NO 47
<211> LENGTH: 20
<212> TYPE: DNA
<213> ORGANISM: Artificial Sequence
<220> FEATURE:
<223> OTHER INFORMATION: Synthetic Construct

<400> SEQUENCE: 47
tcgtcgaccg ttcggaatga                                              20

<210> SEQ ID NO 48
<211> LENGTH: 20
<212> TYPE: DNA
```

<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5
<223> OTHER INFORMATION: b is 5-bromocytosine

<400> SEQUENCE: 48
tbgtbgaccg ttcggaatga                                           20

<210> SEQ ID NO 49
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 49
tcgtbgaccg ttcggaatga                                           20

<210> SEQ ID NO 50
<211> LENGTH: 22
<212> TYPE: DNA
<213> ORGANISM: Artificial Sequence
<220> FEATURE:
<223> OTHER INFORMATION: Synthetic Construct

<400> SEQUENCE: 50
ttcgaacgtt cgttaacgtt cg                                        22

<210> SEQ ID NO 51
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4
<223> OTHER INFORMATION: b is 5-bromocytosine

<400> SEQUENCE: 51
cttbgaacgt tcgagatg                                             18

<210> SEQ ID NO 52
<211> LENGTH: 22
<212> TYPE: DNA
<213> ORGANISM: Artificial Sequence
<220> FEATURE:
<223> OTHER INFORMATION: Synthetic Construct

<400> SEQUENCE: 52
tgatcgtcga acgttcgaga tg                                        22

<210> SEQ ID NO 53
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = T, G, C or B

```
<220> FEATURE:
<221> NAME/KEY: misc_feature
<222> LOCATION: 4
<223> OTHER INFORMATION: n = T, A, or C
<220> FEATURE:
<221> NAME/KEY: misc_feature
<222> LOCATION: 5
<223> OTHER INFORMATION: b is 5-bromocytosine

<400> SEQUENCE: 53 ndanbgktcg                                                                    10

<210> SEQ ID NO 54
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 54 tgaabgttcg                                                                    10

<210> SEQ ID NO 55
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 55 tgaabgutcg                                                                    10

<210> SEQ ID NO 56
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 56 tgacbgttcg                                                                    10

<210> SEQ ID NO 57
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 57 tgatbggtcg                                                                    10

<210> SEQ ID NO 58
```

```
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 58 gtatbggtcg                                                            10

<210> SEQ ID NO 59
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 59 gtacbgttcg                                                            10

<210> SEQ ID NO 60
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 60 gaacbgttcg                                                            10

<210> SEQ ID NO 61
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 61 gaaabgutcg                                                            10

<210> SEQ ID NO 62
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 5
<223> OTHER INFORMATION: b is 5-bromocytosine

<400> SEQUENCE: 62 bgacbgttcg                                                            10
```

```
<210> SEQ ID NO 63
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 63 cgaabgttcg                                                              10

<210> SEQ ID NO 64
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 5
<223> OTHER INFORMATION: b is 5-bromocytosine

<400> SEQUENCE: 64 bgaabgttcg                                                              10

<210> SEQ ID NO 65
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 5
<223> OTHER INFORMATION: b is 5-bromocytosine

<400> SEQUENCE: 65 bgaabgutcg                                                              10

<210> SEQ ID NO 66
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 66 ttaabgutcg                                                              10

<210> SEQ ID NO 67
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 67 tuaabgutcg                                                              10
```

```
<210> SEQ ID NO 68
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 68 ttaabgttcg                                                                  10

<210> SEQ ID NO 69
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11
<223> OTHER INFORMATION: b is 5-bromocytosine

<400> SEQUENCE: 69
tgactgtgaa bgutcgagat ga                                                    22

<210> SEQ ID NO 70
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 9, 19
<223> OTHER INFORMATION: b is 5-bromocytosine

<400> SEQUENCE: 70
tcgtcgaabg ttcgttaabg ttcg                                                  24

<210> SEQ ID NO 71
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11
<223> OTHER INFORMATION: b is 5-bromocytosine

<400> SEQUENCE: 71
tgactgtgaa bgutcggtat ga                                                    22

<210> SEQ ID NO 72
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11
<223> OTHER INFORMATION: b is 5-bromocytosine

<400> SEQUENCE: 72
tgactgtgaa bgutcggaat ga                                                    22
```

<210> SEQ ID NO 73
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11
<223> OTHER INFORMATION: b is 5-bromocytosine

<400> SEQUENCE: 73
tcgtcggaaa bgutcggaat ga                                       22

<210> SEQ ID NO 74
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5, 9
<223> OTHER INFORMATION: b is 5-bromocytosine

<400> SEQUENCE: 74
tcgtbgaabg utcggaatga                                          20

<210> SEQ ID NO 75
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: n = T, C, or B
<220> FEATURE:
<221> NAME/KEY: misc_feature
<222> LOCATION: 4
<223> OTHER INFORMATION: n = T, A, or C

<400> SEQUENCE: 75 ndancgktcg                                                     10

<210> SEQ ID NO 76
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11
<223> OTHER INFORMATION: b is 5-bromocytosine

<400> SEQUENCE: 76
tgactgtgaa bgttcgagat ga                                       22

<210> SEQ ID NO 77
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11, 15

<223> OTHER INFORMATION: b is 5-bromocytosine

<400> SEQUENCE: 77
tgactgtgaa bgttbgagat ga                                            22

<210> SEQ ID NO 78
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11
<223> OTHER INFORMATION: b is 5-bromocytosine

<400> SEQUENCE: 78
tgactgtgaa bgttccagat ga                                            22

<210> SEQ ID NO 79
<211> LENGTH: 22
<212> TYPE: DNA
<213> ORGANISM: Artificial Sequence
<220> FEATURE:
<223> OTHER INFORMATION: Synthetic Construct

<400> SEQUENCE: 79
tgactgtgaa cgtucgagat ga                                            22

<210> SEQ ID NO 80
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 13
<223> OTHER INFORMATION: b is 5-bromocytosine

<400> SEQUENCE: 80
tgactgtgaa cgbutcgaga tga                                           23

<210> SEQ ID NO 81
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11
<223> OTHER INFORMATION: b is 5-bromocytosine

<400> SEQUENCE: 81
tgactgtgaa bgttcgtuat ga                                            22

<210> SEQ ID NO 82
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11
<223> OTHER INFORMATION: b is 5-bromocytosine

<400> SEQUENCE: 82
tgactgtgaa bgttcggtat ga                                          22

<210> SEQ ID NO 83
<211> LENGTH: 18
<212> TYPE: DNA
<213> ORGANISM: Artificial Sequence
<220> FEATURE:
<223> OTHER INFORMATION: Synthetic Construct

<400> SEQUENCE: 83
ctgtgaacgt tcgagatg                                               18

<210> SEQ ID NO 84
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5
<223> OTHER INFORMATION: b is 5-bromocytosine

<400> SEQUENCE: 84
tbgtbgtgaa cgttcgagat ga                                          22

<210> SEQ ID NO 85
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 85
tcgtbgtgaa cgttcgagat ga                                          22

<210> SEQ ID NO 86
<211> LENGTH: 22
<212> TYPE: DNA
<213> ORGANISM: Artificial Sequence
<220> FEATURE:
<223> OTHER INFORMATION: Synthetic Construct

<400> SEQUENCE: 86
tgactgtgaa cgttcgagat ga                                          22

<210> SEQ ID NO 87
<211> LENGTH: 22
<212> TYPE: DNA
<213> ORGANISM: Artificial Sequence
<220> FEATURE:
<223> OTHER INFORMATION: Synthetic Construct

<400> SEQUENCE: 87
tgactgtgaa cgttcgagat ga                                          22

<210> SEQ ID NO 88
<211> LENGTH: 22
<212> TYPE: DNA
<213> ORGANISM: Artificial Sequence
<220> FEATURE:
<223> OTHER INFORMATION: Synthetic Construct

```
<400> SEQUENCE: 88
tgactgtgaa cgttcgtuat ga                                        22

<210> SEQ ID NO 89
<211> LENGTH: 22
<212> TYPE: DNA
<213> ORGANISM: Artificial Sequence
<220> FEATURE:
<223> OTHER INFORMATION: Synthetic Construct

<400> SEQUENCE: 89
tgactgtgaa cgttcgttat ga                                        22

<210> SEQ ID NO 90
<211> LENGTH: 24
<212> TYPE: DNA
<213> ORGANISM: Artificial Sequence
<220> FEATURE:
<223> OTHER INFORMATION: Synthetic Construct

<400> SEQUENCE: 90
tcgttcaacg ttcgttaacg ttcg                                      24

<210> SEQ ID NO 91
<211> LENGTH: 24
<212> TYPE: DNA
<213> ORGANISM: Artificial Sequence
<220> FEATURE:
<223> OTHER INFORMATION: Synthetic Construct

<400> SEQUENCE: 91
tgattcaacg ttcgttaacg ttcg                                      24

<210> SEQ ID NO 92
<211> LENGTH: 18
<212> TYPE: DNA
<213> ORGANISM: Artificial Sequence
<220> FEATURE:
<223> OTHER INFORMATION: Synthetic Construct

<400> SEQUENCE: 92
ctgtcaacgt tcgagatg                                             18

<210> SEQ ID NO 93
<211> LENGTH: 20
<212> TYPE: DNA
<213> ORGANISM: Artificial Sequence
<220> FEATURE:
<223> OTHER INFORMATION: Synthetic Construct

<400> SEQUENCE: 93
tcgtcggaac gttcgagatg                                           20

<210> SEQ ID NO 94
<211> LENGTH: 19
<212> TYPE: DNA
<213> ORGANISM: Artificial Sequence
<220> FEATURE:
<223> OTHER INFORMATION: Synthetic Construct

<400> SEQUENCE: 94
tcgtcggacg ttcgagatg                                            19

<210> SEQ ID NO 95
<211> LENGTH: 19
```

```
<212> TYPE: DNA
<213> ORGANISM: Artificial Sequence
<220> FEATURE:
<223> OTHER INFORMATION: Synthetic Construct

<400> SEQUENCE: 95
tcgtcgtacg ttcgagatg                                                19

<210> SEQ ID NO 96
<211> LENGTH: 19
<212> TYPE: DNA
<213> ORGANISM: Artificial Sequence
<220> FEATURE:
<223> OTHER INFORMATION: Synthetic Construct

<400> SEQUENCE: 96
tcgtcgttcg ttcgagatg                                                19

<210> SEQ ID NO 97
<211> LENGTH: 13
<212> TYPE: DNA
<213> ORGANISM: Artificial Sequence
<220> FEATURE:
<223> OTHER INFORMATION: Synthetic Construct

<400> SEQUENCE: 97
tcgtgaacgt tcg                                                      13

<210> SEQ ID NO 98
<211> LENGTH: 14
<212> TYPE: DNA
<213> ORGANISM: Artificial Sequence
<220> FEATURE:
<223> OTHER INFORMATION: Synthetic Construct

<400> SEQUENCE: 98
tcgtcgaacg ttcg                                                     14

<210> SEQ ID NO 99
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2
<223> OTHER INFORMATION: b is 5-bromocytosine

<400> SEQUENCE: 99
tbgtgaacgt tcg                                                      13

<210> SEQ ID NO 100
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5
<223> OTHER INFORMATION: b is 5-bromocytosine

<400> SEQUENCE: 100
tbgtbgaacg ttcg                                                     14

<210> SEQ ID NO 101
```

```
<211> LENGTH: 13
<212> TYPE: DNA
<213> ORGANISM: Artificial Sequence
<220> FEATURE:
<223> OTHER INFORMATION: Synthetic Construct

<400> SEQUENCE: 101
tcgttaacgt tcg                                                          13

<210> SEQ ID NO 102
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4
<223> OTHER INFORMATION: n = A, C, G or T
<220> FEATURE:
<221> NAME/KEY: misc_feature
<222> LOCATION: 4
<223> OTHER INFORMATION: n = n, nn, or absent
<220> FEATURE:
<221> NAME/KEY: misc_feature
<222> LOCATION: 6
<223> OTHER INFORMATION: n = T, A, or C

<400> SEQUENCE: 102
tcgnancgkt cg                                                           12

<210> SEQ ID NO 103
<211> LENGTH: 11
<212> TYPE: DNA
<213> ORGANISM: Artificial Sequence
<220> FEATURE:
<223> OTHER INFORMATION: Synthetic Construct

<400> SEQUENCE: 103
tcgaacgttc g                                                            11

<210> SEQ ID NO 104
<211> LENGTH: 14
<212> TYPE: DNA
<213> ORGANISM: Artificial Sequence
<220> FEATURE:
<223> OTHER INFORMATION: Synthetic Construct

<400> SEQUENCE: 104
tcgtcgaacg ttcg                                                         14

<210> SEQ ID NO 105
<211> LENGTH: 13
<212> TYPE: DNA
<213> ORGANISM: Artificial Sequence
<220> FEATURE:
<223> OTHER INFORMATION: Synthetic Construct

<400> SEQUENCE: 105
tcgtgaacgt tcg                                                          13

<210> SEQ ID NO 106
<211> LENGTH: 13
<212> TYPE: DNA
<213> ORGANISM: Artificial Sequence
<220> FEATURE:
<223> OTHER INFORMATION: Synthetic Construct

<400> SEQUENCE: 106
```

-continued

```
tcggtatcgg tcg                                              13

<210> SEQ ID NO 107
<211> LENGTH: 13
<212> TYPE: DNA
<213> ORGANISM: Artificial Sequence
<220> FEATURE:
<223> OTHER INFORMATION: Synthetic Construct

<400> SEQUENCE: 107
tcggtaccgt tcg                                              13

<210> SEQ ID NO 108
<211> LENGTH: 13
<212> TYPE: DNA
<213> ORGANISM: Artificial Sequence
<220> FEATURE:
<223> OTHER INFORMATION: Synthetic Construct

<400> SEQUENCE: 108
tcggaaccgt tcg                                              13

<210> SEQ ID NO 109
<211> LENGTH: 12
<212> TYPE: DNA
<213> ORGANISM: Artificial Sequence
<220> FEATURE:
<223> OTHER INFORMATION: Synthetic Construct

<400> SEQUENCE: 109
tcggaacgtt cg                                               12

<210> SEQ ID NO 110
<211> LENGTH: 15
<212> TYPE: DNA
<213> ORGANISM: Artificial Sequence
<220> FEATURE:
<223> OTHER INFORMATION: Synthetic Construct

<400> SEQUENCE: 110
tcgtcggaac gttcg                                            15

<210> SEQ ID NO 111
<211> LENGTH: 12
<212> TYPE: DNA
<213> ORGANISM: Artificial Sequence
<220> FEATURE:
<223> OTHER INFORMATION: Synthetic Construct

<400> SEQUENCE: 111
tcgtaacgtt cg                                               12

<210> SEQ ID NO 112
<211> LENGTH: 11
<212> TYPE: DNA
<213> ORGANISM: Artificial Sequence
<220> FEATURE:
<223> OTHER INFORMATION: Synthetic Construct

<400> SEQUENCE: 112
tcgaccgttc g                                                11

<210> SEQ ID NO 113
<211> LENGTH: 14
<212> TYPE: DNA
```

```
<213> ORGANISM: Artificial Sequence
<220> FEATURE:
<223> OTHER INFORMATION: Synthetic Construct

<400> SEQUENCE: 113
tcgtcgaccg ttcg                                                    14

<210> SEQ ID NO 114
<211> LENGTH: 13
<212> TYPE: DNA
<213> ORGANISM: Artificial Sequence
<220> FEATURE:
<223> OTHER INFORMATION: Synthetic Construct

<400> SEQUENCE: 114
tcgttaacgt tcg                                                     13

<210> SEQ ID NO 115
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2
<223> OTHER INFORMATION: B is 5-bromocytosine
<220> FEATURE:
<221> NAME/KEY: misc_feature
<222> LOCATION: 4
<223> OTHER INFORMATION: n = A, C, G, or T
<220> FEATURE:
<221> NAME/KEY: misc_feature
<222> LOCATION: 4
<223> OTHER INFORMATION: n = n, nn or absent
<220> FEATURE:
<221> NAME/KEY: misc_feature
<222> LOCATION: 6
<223> OTHER INFORMATION: T, A, or C

<400> SEQUENCE: 115
tbgnancgkt cg                                                      12

<210> SEQ ID NO 116
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2
<223> OTHER INFORMATION: b is 5-bromocytosine

<400> SEQUENCE: 116
tbgtgaacgt tcg                                                     13

<210> SEQ ID NO 117
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5
<223> OTHER INFORMATION: b is 5-bromocytosine

<400> SEQUENCE: 117
tbgtbgtgaa cgttcg                                                  16
```

```
<210> SEQ ID NO 118
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2
<223> OTHER INFORMATION: b is 5-bromocytosine

<400> SEQUENCE: 118
tbgaacgttc g                                                             11

<210> SEQ ID NO 119
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2
<223> OTHER INFORMATION: b is 5-bromocytosine

<400> SEQUENCE: 119
tbgaccgttc g                                                             11

<210> SEQ ID NO 120
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5
<223> OTHER INFORMATION: b is 5-bromocytosine

<400> SEQUENCE: 120
tbgtbgaccg ttcg                                                          14

<210> SEQ ID NO 121
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine
<220> FEATURE:
<221> NAME/KEY: misc_feature
<222> LOCATION: 7
<223> OTHER INFORMATION: n = A, C, G, or T
<220> FEATURE:
<221> NAME/KEY: misc_feature
<222> LOCATION: 7
<223> OTHER INFORMATION: n = n, nn or absent
<220> FEATURE:
<221> NAME/KEY: misc_feature
<222> LOCATION: 9
<223> OTHER INFORMATION: n = T, A, or C

<400> SEQUENCE: 121
tcgtbgnanc gktcg                                                         15

<210> SEQ ID NO 122
```

```
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 122
tcgtbgtgaa cgttcg                                                       16

<210> SEQ ID NO 123
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 123
tcgtbgaacg ttcg                                                         14

<210> SEQ ID NO 124
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5
<223> OTHER INFORMATION: b is 5-bromocytosine

<400> SEQUENCE: 124
tcgtbgaccg ttcg                                                         14

<210> SEQ ID NO 125
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4
<223> OTHER INFORMATION: n = A, C, G, or T
<220> FEATURE:
<221> NAME/KEY: misc_feature
<222> LOCATION: 4
<223> OTHER INFORMATION: n = n, nn or absent
<220> FEATURE:
<221> NAME/KEY: misc_feature
<222> LOCATION: 6
<223> OTHER INFORMATION: n = T, A, or C
<220> FEATURE:
<221> NAME/KEY: misc_feature
<222> LOCATION: 7
<223> OTHER INFORMATION: b is 5-bromocytosine

<400> SEQUENCE: 125
tcgnanbgkt cg                                                           12

<210> SEQ ID NO 126
<211> LENGTH: 13
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: 8
<223> OTHER INFORMATION: b is 5-bromocytosine

<400> SEQUENCE: 126
tcggaaabgt tcg                                                          13

<210> SEQ ID NO 127
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 6
<223> OTHER INFORMATION: b is 5-bromocytosine

<400> SEQUENCE: 127
tcgaabgttc g                                                            11

<210> SEQ ID NO 128
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 7
<223> OTHER INFORMATION: B is 5-bromocytosine
<220> FEATURE:
<221> NAME/KEY: misc_feature
<222> LOCATION: 4
<223> OTHER INFORMATION: n = A,T,C or G
<220> FEATURE:
<221> NAME/KEY: misc_feature
<222> LOCATION: 4
<223> OTHER INFORMATION: n = n, nn, or absent
<220> FEATURE:
<221> NAME/KEY: misc_feature
<222> LOCATION: 6
<223> OTHER INFORMATION: n = T, A, or C

<400> SEQUENCE: 128
tbgnanbgkt cg                                                           12

<210> SEQ ID NO 129
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 6
<223> OTHER INFORMATION: b is 5-bromocytosine

<400> SEQUENCE: 129
tbgaabgutc g                                                            11

<210> SEQ ID NO 130
<211> LENGTH: 11
<212> TYPE: DNA
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: 2, 6
<223> OTHER INFORMATION: b is 5-bromocytosine

<400> SEQUENCE: 130
tbgaabgttc g                                                              11

<210> SEQ ID NO 131
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5, 10
<223> OTHER INFORMATION: B is 5-bromocytosine
<220> FEATURE:
<221> NAME/KEY: misc_feature
<222> LOCATION: 7
<223> OTHER INFORMATION: n = A, T, C, or G
<220> FEATURE:
<221> NAME/KEY: misc_feature
<222> LOCATION: 7
<223> OTHER INFORMATION: n = n, nn or absent
<220> FEATURE:
<221> NAME/KEY: misc_feature
<222> LOCATION: 9
<223> OTHER INFORMATION: n = T, A, or C

<400> SEQUENCE: 131
tcgtbgnanb gktcg                                                          15

<210> SEQ ID NO 132
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5, 9
<223> OTHER INFORMATION: b is 5-bromocytosine

<400> SEQUENCE: 132
tcgtbgaabg utcg                                                           14

<210> SEQ ID NO 133
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 5, 9
<223> OTHER INFORMATION: b is 5-bromocytosine

<400> SEQUENCE: 133
tcgtbgaabg ttcg                                                           14

<210> SEQ ID NO 134
<211> LENGTH: 22
<212> TYPE: DNA
<213> ORGANISM: Artificial Sequence
<220> FEATURE:
<223> OTHER INFORMATION: Synthetic Construct

<400> SEQUENCE: 134
tgactgtgaa cgttcgagat ga                                                  22
```

<210> SEQ ID NO 135
<211> LENGTH: 12
<212> TYPE: DNA
<213> ORGANISM: Artificial Sequence
<220> FEATURE:
<223> OTHER INFORMATION: Synthetic Construct

<400> SEQUENCE: 135
tcgaacgttc ga                                                          12

<210> SEQ ID NO 136
<211> LENGTH: 14
<212> TYPE: DNA
<213> ORGANISM: Artificial Sequence
<220> FEATURE:
<223> OTHER INFORMATION: Synthetic Construct

<400> SEQUENCE: 136
tttcgaacgt tcga                                                        14

<210> SEQ ID NO 137
<211> LENGTH: 14
<212> TYPE: DNA
<213> ORGANISM: Artificial Sequence
<220> FEATURE:
<223> OTHER INFORMATION: Synthetic Construct

<400> SEQUENCE: 137
taagcttgca agct                                                        14

<210> SEQ ID NO 138
<211> LENGTH: 26
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 13
<223> OTHER INFORMATION: n = rA

<400> SEQUENCE: 138
tcgaacgttc gantttcgaa cgttcg                                           26

<210> SEQ ID NO 139
<211> LENGTH: 13
<212> TYPE: DNA
<213> ORGANISM: Artificial Sequence
<220> FEATURE:
<223> OTHER INFORMATION: Synthetic Construct

<400> SEQUENCE: 139
tcgaacgttc gaa                                                         13

<210> SEQ ID NO 140
<211> LENGTH: 18
<212> TYPE: DNA
<213> ORGANISM: Artificial Sequence
<220> FEATURE:
<223> OTHER INFORMATION: Synthetic Construct

<400> SEQUENCE: 140
ttggccaagc ttggccaa                                                    18

<210> SEQ ID NO 141

```
<211> LENGTH: 22
<212> TYPE: DNA
<213> ORGANISM: Artificial Sequence
<220> FEATURE:
<223> OTHER INFORMATION: Synthetic Construct

<400> SEQUENCE: 141
tgactgtgaa cgttcgagat ga                                              22

<210> SEQ ID NO 142
<211> LENGTH: 22
<212> TYPE: DNA
<213> ORGANISM: Artificial Sequence
<220> FEATURE:
<223> OTHER INFORMATION: Synthetic Construct

<400> SEQUENCE: 142
tgactgtgaa ccttagagat ga                                              22

<210> SEQ ID NO 143
<211> LENGTH: 22
<212> TYPE: DNA
<213> ORGANISM: Artificial Sequence
<220> FEATURE:
<223> OTHER INFORMATION: Synthetic Construct

<400> SEQUENCE: 143
tgactgtgaa cgttcgagat ga                                              22

<210> SEQ ID NO 144
<211> LENGTH: 22
<212> TYPE: DNA
<213> ORGANISM: Artificial Sequence
<220> FEATURE:
<223> OTHER INFORMATION: Synthetic Construct

<400> SEQUENCE: 144
tgactgtgaa ccttagagat ga                                              22

<210> SEQ ID NO 145
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7
<223> OTHER INFORMATION: n = A,T,C or G
<220> FEATURE:
<221> NAME/KEY: misc_feature
<222> LOCATION: 7
<223> OTHER INFORMATION: n = n, nn or absent
<220> FEATURE:
<221> NAME/KEY: misc_feature
<222> LOCATION: 9
<223> OTHER INFORMATION: n = T, A, or C

<400> SEQUENCE: 145
tcgtcgnanc gktcg                                                      15

<210> SEQ ID NO 146
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

```
<222> LOCATION: 2, 5
<223> OTHER INFORMATION: B is 5-bromocytosine
<220> FEATURE:
<221> NAME/KEY: misc_feature
<222> LOCATION: 7
<223> OTHER INFORMATION: n = A, T, C, or G
<220> FEATURE:
<221> NAME/KEY: misc_feature
<222> LOCATION: 7
<223> OTHER INFORMATION: n = n, nn, or absent
<220> FEATURE:
<221> NAME/KEY: misc_feature
<222> LOCATION: 9
<223> OTHER INFORMATION: n = T, A, or C

<400> SEQUENCE: 146
tbgtbgnanc gktcg                                                       15

<210> SEQ ID NO 147
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 7
<223> OTHER INFORMATION: n = A,T,C or G
<220> FEATURE:
<221> NAME/KEY: misc_feature
<222> LOCATION: 7
<223> OTHER INFORMATION: n = n, nn or absent
<220> FEATURE:
<221> NAME/KEY: misc_feature
<222> LOCATION: 9
<223> OTHER INFORMATION: n = A, T, or C
<220> FEATURE:
<221> NAME/KEY: misc_feature
<222> LOCATION: 10
<223> OTHER INFORMATION: b is 5-bromocytosine

<400> SEQUENCE: 147
tcgtcgnanb gktcg                                                       15

<210> SEQ ID NO 148
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5, 10
<223> OTHER INFORMATION: b is 5-bromocytosine
<220> FEATURE:
<221> NAME/KEY: misc_feature
<222> LOCATION: 7
<223> OTHER INFORMATION: n = A, C, G, or T
<220> FEATURE:
<221> NAME/KEY: misc_feature
<222> LOCATION: 7
<223> OTHER INFORMATION: n = n, nn, or absent
<220> FEATURE:
<221> NAME/KEY: misc_feature
<222> LOCATION: 9
<223> OTHER INFORMATION: n = T, A, or C

<400> SEQUENCE: 148
tbgtbgnanb gktcg                                                       15
```

US 7,625,872 B2

BRANCHED IMMUNOMODULATORY COMPOUNDS AND METHODS OF USING THE SAME

CROSS-REFERENCE TO RELATED PATENT APPLICATIONS

This application claims benefit of U.S. provisional patent application No. 60/436,406 filed Dec. 23, 2002, the entire disclosure of which is incorporated by reference.

TECHNICAL FIELD

The present invention relates to compounds and methods for modulation of an immune response by cells and in individuals. The invention finds use in the fields of biomedicine and immunology.

BACKGROUND

Reference to a publication in this section should not be construed as an indication that the publication is prior art to the present invention.

The type of immune response generated by infection or other antigenic challenge can generally be distinguished by the subset of T helper (Th) cells involved in the response. The Th1 subset is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets. See, for example, Romagnani (2000) *Ann. Allergy Asthma Immunol.* 85:9-18.

The Th1 subset may be particularly suited to respond to viral infections, intracellular pathogens, and tumor cells because it secretes IL-2 and IFN-γ, which activate CTLs. The Th2 subset may be more suited to respond to free-living bacteria and helminthic parasites and may mediate allergic reactions, since IL-4 and IL-5 are known to induce IgE production and eosinophil activation, respectively. In general, Th1 and Th2 cells secrete distinct patterns of cytokines and so one type of response can moderate the activity of the other type of response. A shift in the Th1/Th2 balance can result in an allergic response, for example, or, alternatively, in an increased CTL response.

It has been recognized for some time that a Th1-type immune response can be induced in mammals by administration of certain immunomodulatory polynucleotides. The immunomodulatory polynucleotides include sequences referred to as immunostimulatory sequences ("ISS"), often including a CG dinucleotide. See, e.g., PCT Publications WO 98/55495, WO 97/28259, U.S. Pat. Nos. 6,194,388 and 6,207, 646; and Krieg et al. (1995) *Nature* 374:546-49. For many infectious diseases, such as tuberculosis and malaria, Th2-type responses are of little protective value against infection. Protein-based vaccines typically induce Th2-type immune responses, characterized by high titers of neutralizing antibodies but without significant cell-mediated immunity. Moreover, some types of antibody responses are inappropriate in certain indications, most notably in allergy where an IgE antibody response can result in anaphylactic shock.

In view of the need for improved methods of immunotherapy, a need exists for identification of compounds for modulation of an immune response.

BRIEF SUMMARY OF THE INVENTION

In one aspect, the invention provides a branched immunomodulatory compound (BIC) comprising a branch-point nucleoside to which three core nucleic acid moieties are covalently coupled, where each of the three core nucleic acid moieties is linked to a different position of the branch-point nucleoside; the BIC optionally comprises one or more additional nucleic acid moieties; and at least one nucleic acid moiety of the BIC comprises the sequence 5'-CG-3'. In an embodiment, the BIC comprises a spacer moiety. In an embodiment, one or more of the core nucleic acid moieties in the BIC is covalently coupled to the branch-point nucleoside by a linkage that is phosphodiester, phosphotriester, phosphorothioate ester, phosphorodithioate ester, phosphoramidite or alkylphosphonate. In an embodiment, one or more of the three core nucleic acid moieties in the BIC is covalently coupled to the branch-point nucleoside through a spacer moiety.

In one aspect, the invention provides a BIC comprising two branch-point nucleosides covalently coupled to each other by a spacer moiety, wherein the linkage between said two branch-point nucleosides does not comprise a nucleic acid moiety, where each of said branch point nucleosides is covalently coupled to at least two other moieties, wherein each moiety is independently selected from the group consisting of branch-point nucleosides and nucleic acid moieties; the BIC comprises at least four nucleic acid moieties; and at least one nucleic acid moiety of the BIC comprises the sequence 5'-CG-3'.

In an embodiment, at least one, at least two, at least three, or at least four nucleic acid moieties of the BIC are covalently coupled to a branch-point nucleoside through a spacer moiety. In some embodiments, the spacer moiety comprises a component selected from the group consisting of HEG, TEG, or C2-C10 alkyl, and/or phophodiester- or phosphorothioate-linked oligoethylene glycol moieties.

A nucleic acid moiety may be linked to at least one spacer moiety by a phosphodiester linkage, a phosphothioate ester linkage, or a phosphorodithioate ester linkage. A branch-point nucleoside may be linked to at least one spacer moiety by a phosphodiester linkage, a phosphothioate ester linkage, or a phosphorodithioate ester linkage.

The BIC of the invention may comprise one or more nucleic acid moieties (e.g., core nucleic acid moieties [NAMs], prime NAMs, and/or peripheral NAMs) that comprises the sequence 5'-CG-3', alternatively the sequence 5'-TCG-3', alternatively the sequence 5'-TCG(A/T)-3', alternatively sequence 5'-TCG(A/T)CG-3', alternatively the sequence 5'-TCG(A/T)CG(A/T)-3', alternatively the sequence 5'-TCGACGT-3' or 5'-TCGTCGA-3'.

The BIC of the invention may comprise one or more nucleic acid moieties (e.g., core nucleic acid moieties [NAMs], prime NAMs, and/or peripheral NAMs) less than 12 nucleotides in length or less than 15 nucleotides in length. In an embodiment, each of the NAMs in a BIC that comprises the sequence 5'-CG-3' is less than 8 nucleotides in length.

In an aspect, the BIC comprises a branch-point nucleoside (bN) that is a ribonucleoside. In an embodiment, the BIC comprises one nucleic acid moiety linked to the base of the branch-point nucleoside, one nucleic acid moiety linked to the 5'-position of the branch-point nucleoside, and one nucleic acid moiety linked to either the 3'-or 2'-position of the branch-point nucleoside.

In an aspect, the BIC may the branch point nucleoside is a 2'-deoxyribonucleoside. In an embodiment, one nucleic acid moiety is linked to the base of the branch-point nucleoside, one nucleic acid moiety is linked to the 5'-position of the branch-point nucleoside, and one nucleic acid moiety is linked to the 3'-position of the branch-point nucleoside.

In an embodiment, the BIC comprises a pyrimidine base.

In an embodiment, the branch point nucleoside is a 2'-deoxyribonucleoside comprising a pyrimidine base, one nucleic acid moiety linked to the 5'-position of the branch-point nucleoside, one nucleic acid moiety linked to the 3'-position of the branch-point nucleoside, and one nucleic acid moiety linked to the 5'-C, 4'-C, or 3'-C position on the sugar of the branch-point nucleoside.

In an embodiment, the branch point nucleoside is a ribonucleoside comprising a pyrimidine base, one nucleic acid moiety linked to the 5'-position of the branch-point nucleoside, one nucleic acid moiety linked to either the 2'- or 3'-position of the branch-point nucleoside, and one nucleic acid moieties linked to the 5'-C, 4'-C, or 3'-C position on the sugar of the branch-point nucleoside.

In various embodiments, a BIC described herein has one or more of the following characteristics: (vii) the BIC includes at least one nucleic acid moiety of the BIC that does not have "isolated immunomodulatory activity," (viii) the BIC does not include any nucleic acid moiety with "isolated immunomodulatory activity," (ix) the BIC includes at least one nucleic acid moiety of the BIC that has "inferior isolated immunological activity." BICs can have self-complementary nucleic acid moieties such that duplexes can be formed.

The BIC may have at least one immunomodulatory activity such as (a) the ability to stimulate IFN-γ production by human peripheral blood mononuclear cells; (b) the ability to stimulate IFN-α production by human peripheral blood mononuclear cells; and/or (c) the ability to stimulate proliferation of human B cells.

The invention also provides compositions comprising a BIC along with a pharmaceutically acceptable excipient and/or an antigen and/or a cationic microcarrier (such as a polymer of lactic acid and glycolic acid). The composition can be essentially endotoxin-free.

In an aspect, the invention provides a composition containing a BIC described herein and a pharmaceutically acceptable excipient, an antigen (e.g., an antigen to which an immune response is desired), or both. In an embodiment, the composition is formulated under GMP standards. In an embodiment, the composition is prepared by a process that includes assaying the composition for the presence of endotoxin. In an embodiment, the composition is essentially endotoxin-free. In an embodiment, the composition does not contain liposomes.

In an aspect, the invention provides the use of a BIC as described herein for the manufacture of a medicament.

In an aspect, the invention provides a method of modulating an immune response of a cell by contacting the cell with a BIC-containing composition. In an embodiment, the BIC-containing composition comprises a multimeric BIC.

In an aspect, the invention provides a method of modulating an immune response in an individual by administering a branched immunomodulatory compound or BIC-containing composition as described herein, in an amount sufficient to modulate an immune response in the individual. In one embodiment, the individual suffers from a disorder associated with a Th2-type immune response, for example, an allergy or allergy-induced asthma. In one embodiment, the individual has an infectious disease.

In an aspect, the invention provides a method of increasing interferon-gamma (IFN-γ) in an individual by administering a BIC or composition as described herein, in an amount sufficient to increase IFN-γ in the individual. In an embodiment, the individual has an inflammatory disorder. In an embodiment, the individual has idiopathic pulmonary fibrosis.

In an aspect, the invention provides a method of increasing interferon-alpha (IFN-α) in an individual, by administering a BIC or composition as described herein, in an amount sufficient to increase IFN-α in the individual. In an embodiment, the individual has a viral infection.

In an aspect, the invention provides a method of ameliorating a symptom of an infectious disease in an individual, by administering an effective amount of a BIC or composition, as described herein, to the individual, where the effective amount is an amount sufficient to ameliorate a symptom of the infectious disease.

In an aspect, the invention provides a method of ameliorating an IgE-related disorder in an individual, by administering an effective amount of a BIC or composition described herein to an individual having an IgE-related disorder, where an effective amount is an amount sufficient to ameliorate a symptom of the IgE-related disorder. In an embodiment, the IgE-related disorder is allergy or an allergy-related disorder.

The invention further provides a method of modulating an immune response in an individual by administering to an individual a BIC in an amount sufficient to modulate an immune response in said individual. In embodiments, the individual has cancer and/or suffers from a disorder associated with a Th2-type immune response (e.g., an allergy or allergy-induced asthma) and/or has an infectious disease.

BRIEF DESCRIPTION OF THE FIGURES

FIGS. 1A-1D show branch-point nucleosides derived from 2'-deoxyuridine and FIGS. 1E-1F show a branched-point derived from 2'-deoxycytidine.

DETAILED DESCRIPTION OF THE INVENTION

I. General Methods

Figure 1:
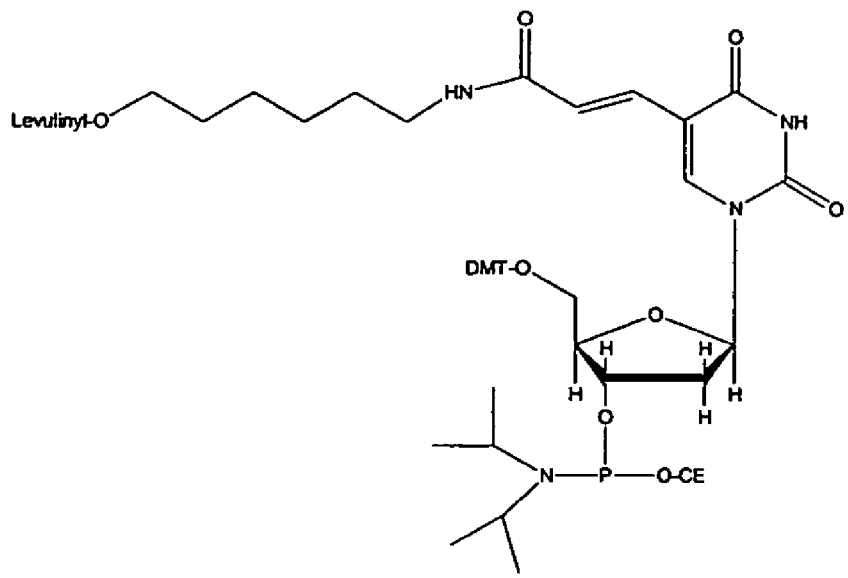
FIG. 1 shows examples of commercially available branch-point nucleosides containing a protected spacer moiety and a reactive group (FIGS. 1A, 1C, and 1E) and portions of BICs incorporating these compounds (FIGS. 1B, 1D, and 1F).
Figure 1:
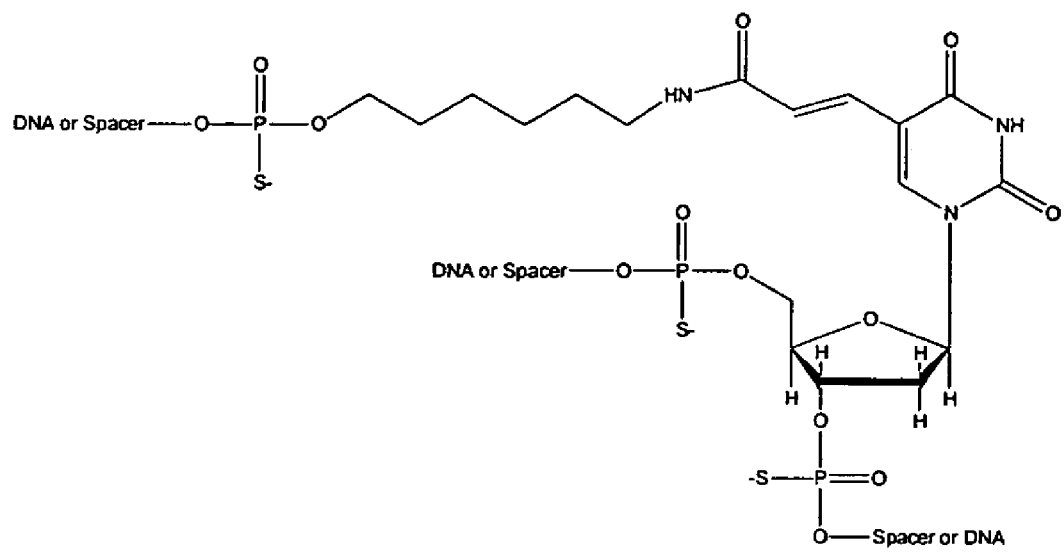
Figure 1:
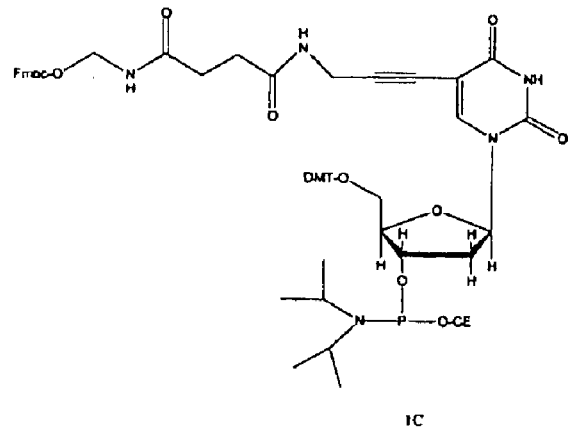
Figure 1:
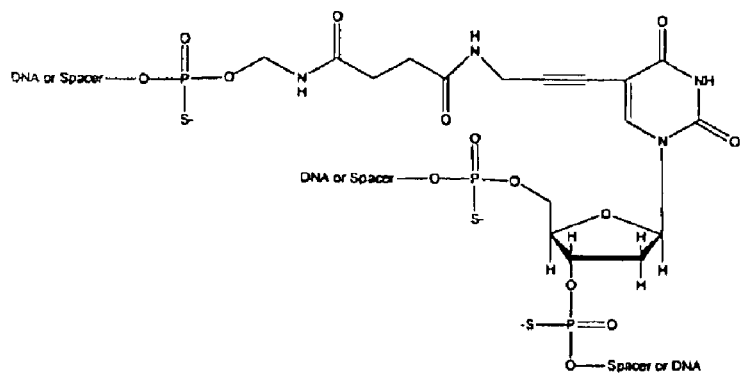
Figure 1:
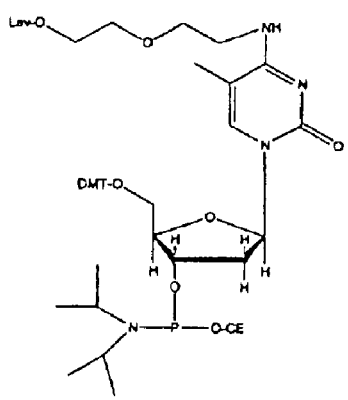
Figure 1:
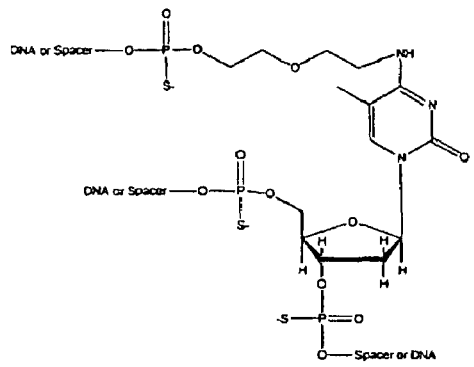

The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly and individually referred to herein as "Sambrook"). *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987, including supplements through 2001); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press NY, 1994); *Bioconjugate Techniques* (Greg T. Hermanson, ed., Academic Press, 1996); *Methods of Immunological Analysis* (R. Masseyeff, W. H. Albert, and N. A. Staines, eds., Weinheim: VCH Verlags gesellschaft mbH, 1993), Harlow and Lane (1988) *Antibodies, A Laboratory Manual*, Cold Spring Harbor Publications, New York, and Harlow and Lane (1999) *Using Antibodies: A Laboratory Manual* Cold Spring Harbor Laboratory Press, Cold Spring Harbor, N.Y. (jointly and individually referred to herein as "Harlow and Lane"), Beaucage et al. eds., *Current Protocols in Nucleic Acid Chemistry* John Wiley & Sons, Inc., New York, 2000); and Agrawal, ed., *Protocols for Oligonucleotides and Analogs, Synthesis and Properties* Humana Press Inc., New Jersey, 1993).

II. Definitions

As used herein, the singular form "a", "an", and "the" includes plural references unless otherwise indicated or clear from context.

As used interchangeably herein, the terms "polynucleotide," "oligonucleotide" and "nucleic acid" include single-stranded DNA (ssDNA), double-stranded DNA (dsDNA), single-stranded RNA (ssRNA) and double-stranded RNA (dsRNA), modified oligonucleotides and oligonucleosides, or combinations thereof. The nucleic acid can be linearly or circularly configured, or the oligonucleotide can contain both linear and circular segments. Nucleic acids are polymers of nucleosides joined, e.g., through phosphodiester linkages or alternate linkages, such as phosphorothioate esters. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

An element, e.g., region, portion, non-nucleic acid spacer moiety, nucleic acid moiety, or sequence is "adjacent" to another element, e.g., region, portion, non-nucleic acid spacer moiety, nucleic acid moiety, or sequence, when it directly abuts that region, portion, spacer or sequence.

The term "BIC-antigen conjugate" refers to a complex in which a BIC and an antigen are linked. Such conjugate linkages include covalent and/or non-covalent linkages.

The term "antigen" means a substance that is recognized and bound specifically by an antibody or by a T cell antigen receptor. Antigens can include peptides, proteins, glycoproteins, polysaccharides, complex carbohydrates, sugars, gangliosides, lipids and phospholipids; portions thereof and combinations thereof. The antigens can be those found in nature or can be synthetic. Antigens suitable for administration with a BIC includes any molecule capable of eliciting a B cell or T cell antigen-specific response. Preferably, antigens elicit an antibody response specific for the antigen. Preferably, antigens of the present invention include peptides, lipids (e.g. sterols, fatty acids, and phospholipids), polysaccharides such as those used in Hemophilus influenza vaccines, gangliosides and glycoproteins.

"Adjuvant" refers to a substance which, when added to an immunogenic agent such as antigen, nonspecifically enhances or potentiates an immune response to the agent in the recipient host upon exposure to the mixture.

The term "peptide" are polypeptides that are of sufficient length and composition to effect a biological response, e.g., antibody production or cytokine activity whether or not the peptide is a hapten. Typically, the peptides are at least six amino acid residues in length. The term "peptide" further includes modified amino acids (whether or not naturally or non-naturally occurring), such modifications including, but not limited to, phosphorylation, glycosylation, pegylation, lipidization and methylation.

"Antigenic peptides" can include purified native peptides, synthetic peptides, recombinant peptides, crude peptide extracts, or peptides in a partially purified or unpurified active state (such as peptides that are part of attenuated or inactivated viruses, cells, micro-organisms), or fragments of such peptides. An "antigenic peptide" or "antigen polypeptide" accordingly means all or a portion of a polypeptide which exhibits one or more antigenic properties. Thus, for example, an "Amb a 1 antigenic polypeptide" or "Amb a 1 polypeptide antigen" is an amino acid sequence from Amb a 1, whether the entire sequence, a portion of the sequence, and/or a modification of the sequence, which exhibits an antigenic property (i.e., binds specifically to an antibody or a T cell receptor).

A "delivery molecule" or "delivery vehicle" is a chemical moiety which facilitates, permits, and/or enhances delivery of a BIC, BIC-antigen mixture, or BIC-antigen conjugate to a particular site and/or with respect to particular timing. A delivery vehicle may or may not additionally stimulate an immune response.

An "allergic response to antigen" means an immune response generally characterized by the generation of eosinophils (usually in the lung) and/or antigen-specific IgE and their resultant effects. As is well-known in the art, IgE binds to IgE receptors on mast cells and basophils. Upon later exposure to the antigen recognized by the IgE, the antigen cross-links the IgE on the mast cells and basophils causing degranulation of these cells, including, but not limited, to histamine release. It is understood and intended that the terms "allergic response to antigen", "allergy", and "allergic condition" are equally appropriate for application of some of the methods of the invention. Further, it is understood and intended that the methods of the invention include those that are equally appropriate for prevention of an allergic response as well as treating a pre-existing allergic condition.

As used herein, the term "allergen" means an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule. A number of isolated allergens are known in the art. These include, but are not limited to, those provided in Table 1 herein.

The term "desensitization" refers to the process of the administration of increasing doses of an allergen to which the subject has demonstrated sensitivity. Examples of allergen doses used for desensitization are known in the art, see, for example, Fornadley (1998) Otolaryngol. Clin. North Am. 31:111-127.

"Antigen-specific immunotherapy" refers to any form of immunotherapy which involves antigen and generates an antigen-specific modulation of the immune response. In the allergy context, antigen-specific immunotherapy includes, but is not limited to, desensitization therapy.

The term "microcarrier" refers to a particulate composition which is insoluble in water and which has a size of less than about 150, 120 or 100 µm, more commonly less than about 50-60 µm, and may be less than about 10 µm or even less than about 5 µm. Microcarriers include "nanocarriers", which are microcarriers have a size of less than about 1 µm, preferably less than about 500 nm. Microcarriers include solid phase particles such a particles formed from biocompatible naturally occurring polymers, synthetic polymers or synthetic copolymers, although microcarriers formed from agarose or cross-linked agarose may be included or excluded from the definition of microcarriers herein as well as other biodegradable materials known in the art. Solid phase microcarriers are formed from polymers or other materials which are non-erodible and/or non-degradable under mammalian physiological conditions, such as polystyrene, polypropylene, silica, ceramic, polyacrylamide, gold, latex, hydroxyapatite, and ferromagnetic and paramagnetic materials. Biodegradable solid phase microcarriers may be formed from polymers which are degradable (e.g., poly(lactic acid), poly(glycolic acid) and copolymers thereof, such as poly(D, L-lactide-co-glycolide) or erodible (e.g., poly(ortho esters such as 3,9-diethylidene-2,4,8,10-tetraoxaspiro[5.5] undecane (DETOSU) or poly(anhydrides), such as poly(anhydrides) of sebacic acid) under mammalian physiological conditions. Microcarriers may also be liquid phase (e.g., oil or lipid based), such as liposomes, iscoms (immune-stimulating complexes, which are stable complexes of cholesterol, phospholipid and adjuvant-active saponin) without antigen, or droplets or micelles found in oil-in-water or water-in-oil emulsions. Biodegradable liquid phase microcarriers typically incorporate a biodegradable oil, a number of which are known in the art, including squalene and vegetable oils. Microcarriers are typically spherical in shape, but microcarriers which deviate from spherical shape are also acceptable (e.g., ellipsoidal, rod-shaped, etc.). Due to their insoluble nature, solid phase microcarriers are filterable from water and water-based (aqueous) solutions (e.g., using a 0.2 micron filter).

The term "nonbiodegradable", as used herein, refers to a microcarrier which is not degraded or eroded under normal mammalian physiological conditions. Generally, a microcarrier is considered nonbiodegradable if it not degraded (i.e., loses less than 5% of its mass or average polymer length) after a 72 hour incubation at 37° C. in normal human serum.

A microcarrier is considered "biodegradable" if it is degradable or erodable under normal mammalian physiological conditions. Generally, a microcarrier is considered biodegradable if it is degraded (i.e., loses at least 5% of its mass or average polymer length) after a 72 hour incubation at 37° C. in normal human serum.

The term "BIC/microcarrier complex" or "BIC/MC complex" refers to a complex of a BIC and a microcarrier. The components of the complex may be covalently or non-covalently linked. Non-covalent linkages may be mediated by any non-covalent bonding force, including by hydrophobic interaction, ionic (electrostatic) bonding, hydrogen bonds and/or van der Waals attractions. In the case of hydrophobic linkages, the linkage is generally via a hydrophobic moiety (e.g., cholesterol) covalently linked to the BIC.

An "individual" or "subject" is a vertebrate, such as avian, preferably a mammal, such as a human. Mammals include, but are not limited to, humans, non-human primates, farm animals, sport animals, experimental animals, rodents (e.g., mice and rats) and pets.

An "effective amount" or a "sufficient amount" of a substance is that amount sufficient to effect a desired biological effect, such as beneficial results, including clinical results, and, as such, an "effective amount" depends upon the context in which it is being applied. In the context of administering a composition that modulates an immune response to a co-administered antigen, an effective amount of a BIC and antigen is an amount sufficient to achieve such a modulation as compared to the immune response obtained when the antigen is administered alone. An effective amount can be administered in one or more administrations.

The term "co-administration" as used herein refers to the administration of at least two different substances sufficiently close in time to modulate an immune response. Preferably, co-administration refers to simultaneous administration of at least two different substances.

"Stimulation" of an immune response, such as Th1 response, means an increase in the response, which can arise from eliciting and/or enhancement of a response. Similarly, "stimulation" of a cytokine or cell type (such as CTLs) means an increase in the amount or level of cytokine or cell type.

An "IgE associated disorder" is a physiological condition which is characterized, in part, by elevated IgE levels, which may or may not be persistent. IgE associated disorders include, but are not limited to, allergy and allergic reactions, allergy-related disorders (described below), asthma, rhinitis, atopic dermatitis, conjunctivitis, urticaria, shock, Hymenoptera sting allergies, food allergies, and drug allergies, and parasite infections. The term also includes related manifestations of these disorders. Generally, IgE in such disorders is antigen-specific.

An "allergy-related disorder" means a disorder resulting from the effects of an antigen-specific IgE immune response. Such effects can include, but are not limited to, hypotension and shock. Anaphylaxis is an example of an allergy-related disorder during which histamine released into the circulation causes vasodilation as well as increased permeability of the capillaries with resultant marked loss of plasma from the circulation. Anaphylaxis can occur systemically, with the associated effects experienced over the entire body, and it can occur locally, with the reaction limited to a specific target tissue or organ.

The term "viral disease", as used herein, refers to a disease which has a virus as its etiologic agent. Examples of viral diseases include hepatitis B, hepatitis C, influenza, acquired immunodeficiency syndrome (AIDS), and herpes zoster.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder. Especially in the allergy context, as is well understood by those skilled in the art, palliation may occur upon modulation of the immune response against an allergen(s). Further, palliation does not necessarily occur by administration of one dose, but often occurs upon administration of a series of doses. Thus, an amount sufficient to palliate a response or disorder may be administered in one or more administrations.

An "antibody titer", or "amount of antibody", which is "elicited" by a BIC and antigen refers to the amount of a given antibody measured at a time point after administration of the BIC and antigen.

A "Th1-associated antibody" is an antibody whose production and/or increase is associated with a Th1 immune response. For example, IgG2a is a Th1-associated antibody in mouse. For purposes of this invention, measurement of a Th1-associated antibody can be measurement of one or more such antibodies. For example, in humans, measurement of a Th1-associated antibody could entail measurement of IgG1 and/or IgG3.

A "Th2-associated antibody" is an antibody whose production and/or increase is associated with a Th2 immune response. For example, IgGI is a Th2-associated antibody in mouse. For purposes of this invention, measurement of a Th2-associated antibody can be measurement of one or more such antibodies. For example, in human, measurement of a Th2-associated antibody could entail measurement of IgG2 and/or IgG4.

To "suppress" or "inhibit" a function or activity, such as cytokine production, antibody production, or histamine release, is to reduce the function or activity when compared to otherwise same conditions except for a condition or parameter of interest, or alternatively, as compared to another condition. For example, a composition comprising a BIC and antigen which suppresses histamine release reduces histamine release as compared to, for example, histamine release induced by antigen alone. As another example, a composition comprising a BIC and antigen which suppresses antibody production reduces extent and/or levels of antibody as compared to, for example, extent and/or levels of antibody produced by antigen alone.

As used herein manufactured or formulated "under GMP standards," when referring to a pharmaceutical composition means the composition is formulated as sterile, substantially isotonic and in full compliance with all Good Manufacturing Practice (GMP) regulations of the U.S. Food and Drug Administration.

As used herein, the term "immunogenic" has the normal meaning in the art and refers to an agent (e.g., polypeptide) that elicits an adaptive immune response upon injection into a person or animal. The immune response may be B cell (humoral) and/or T cell (cellular).

As used herein, the phrase "position" in the context of covalent linkages to a molecule (e.g., a branch-point nucleoside) has its usual meaning in the chemical arts. Position refers to attachment points for substituents, e.g., where substituents replace a hydrogen atom in the unmodified molecule. For example, because the branch-point nucleosides are chiral, each hydrogen atom in the unmodified branch-point nucleoside represents a different position of the branch-point nucleoside for potential attachment of substituents (e.g., NAMs, SMs, etc.). Thus, a NAM attached to the 3'-hydroxy site and a NAM attached to a 3'-C-(hydroxymethyl) site of the same branch-point nucleoside are attached to different positions of the branch-point nucleoside.

All ranges are intended to be inclusive of the terminal values. Thus, a polymer of "from 2 to 7 nucleotides" or "between 2 and 7 nucleotides" includes polymers of 2 nucleotides and polymers of 7 nucleotides. Where a lower limit and an independently selected upper limit are described, it is understood that the upper limit is higher than the lower limit.

III. Branched Immunomodulatory Compounds (BICs)

The invention provides branched nucleoside immunomodulatory compounds ("BICs") that may be used, inter alia, for modulating an immune response. Thus, the invention provides new reagents and methods for modulating an immune response, including treatment and prophylaxis of disease in humans and other animals. The following sections describe the structure and properties of BICs.

1. Structure of BICs: Introduction

Branched immunomodulatory compounds ("BICs") of the present invention contain one or more branch-point nucleosides ("bNs") and one or more nucleic acid moieties ("NAMs"). The structure and properties of branch-point nucleosides are described in detail in Section III.3, infra, and elsewhere herein. Briefly, however, a branch-point nucleoside is a nucleoside that is covalently coupled to at least three other moieties ("M"), where each moiety is either (1) a second branch-point nucleside or (2) a nucleic acid moiety. The structure and properties of NAMs are described in detail in Section III.2, infra, and elsewhere herein. However, for purposes of this introduction, and not for limitation, NAMs can be considered to be nucleotide monomers (1 nucleotide) or polymers (2-100 nucleotides). The meaning of the term "covalently coupled" is also discussed infra. In brief, "covalently coupled" refers to two moieties (e.g., two bNs or a bN and a NAM) that are joined through a series of covalent chemical bonds with the proviso that no intervening NAM or bN lies between the two covalently coupled moieties. As will be apparent to the reader, in certain common embodiments, the linkage between the two moieties includes a non-nucleic acid "spacer moiety (SM)." The structure and properties of spacer moieties are described in detail in Section III.4, infra, and elsewhere herein.

From the forgoing description it will be apparent that BICs of the invention comprise the structure:

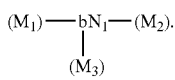

Structure I where $M_1$, $M_2$ and $M_3$ are moieties each independently selected from the group consisting of NAMs and bNs, and "-" indicates that the moieties are covalently coupled to the branch-point nucleoside, $bN_1$. According to the invention, each of $M_1$, $M_2$, and $M_3$ is linked to a different position of the branch-point nucleoside. Various specific embodiments of the BIC of the invention can be described with reference to Structure I. For example, in one embodiment, $M_1$, $M_2$ and $M_3$ are all nucleic acid moieties and the BIC comprises the structure:

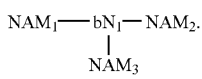

Structure II where $NAM_1$, $NAM_2$, and $NAM_3$, are independently selected nucleic acid moieties.

In another embodiment, at least one moiety of a BIC comprising Structure I is another branch-point nucleoside, and the BIC has the structure:

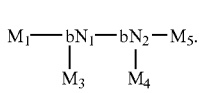

Structure III where $bN_2$ is the second branch point nucleoside (which may be the same or different from the first) and $M_4$ and $M_5$ are moieties independently selected from the group consisting of NAMs and bNs. It will be recognized that if either $M_4$ or $M_5$ was absent, the structure designated "$bN_2$" would not be a branch-point nucleoside.

It will be appreciated by the reader that Structures I, II, and III, are "core" structures. The BICs of the invention, so long as they comprise one or more of the structures shown, may, and often do, include additional covalently coupled NAMs and bNs, as well as other covalently bound groups and atoms. For example, structures A and B, below, each describe a BIC comprising the core structure of structure II.

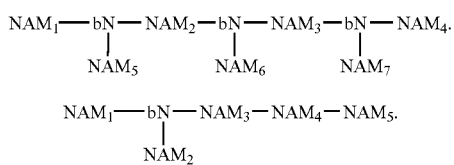

As is noted above, a branch-point nucleoside of a BIC is covalently coupled to at least three other moieties, of which one or more can be a NAM. As is also noted above, a first moiety (e.g., bN) is "covalently coupled" to a second moiety (e.g., M) when (1) the two moieties are connected to each other by a series of covalent bonds (as distinguished from, for example, moieties that are physically associated via ligand-anti-ligand interactions, base-pairing, "hydrophobic interactions," and the like) and (2) no nucleic acid moiety or branch point nucleoside is present between the two moieties (i.e., there are no intervening NAMs or bNs between the covalently coupled moieties).

According to the invention, two moieties may be covalently coupled in a variety of ways. For example (and not for limitation), the two moieties may be coupled by an ester linkage (e.g., a phosphodiester linkage between a hydroxyl group of a bN and a terminal phosphate group of a NAM), a phosphoramidite linkage (e.g., between an amino group of a bN and a terminal phosphate group of a NAM), an alkylphosphonate linkage (e.g., between a hydroxyl group of a bN and a terminal phosphonate group of a NAM). In addition, a NAM may be covalently coupled to the base or sugar of a bN, through a "spacer moiety (SM)" (see, e.g., Section III.4, infra).

For ease of description, NAMs in a BIC that are covalently coupled to a bN are sometimes referred to as "core nucleic acid moieties (core NAMs)" and NAMs in a BIC that are not covalently coupled to a bN are sometimes referred to as "peripheral nucleic acid moieties (peripheral NAMs)." In Structure B, supra, $NAM_1$, $NAM_2$, $_{and}NAM_3$ are core NAMs, and $NAM_4$ and $NAM_5$ are peripheral NAMs.

Exemplary BIC structures are described in Examples 1-8, infra.

2. Nucleic Acid Moieties

The BICs of the invention comprise three or more nucleic acid moieties. The term "nucleic acid moiety," as used herein, refers to a nucleotide polymer (i.e., comprising at least 2 contiguous nucleotides)[ii] or monomer (i.e., a mononucleotide), with the proviso that a bN cannot be a NAM. As used herein, a nucleotide is (1) a purine or pyrimidine base linked to a sugar that is in an ester linkage to a phosphate group, or (2) an analog in which the base and/or sugar and/or phosphate ester are replaced by analogs, e.g., as described infra.

As noted, a BIC comprises at least three NAMs, and can comprise a significantly larger number (e.g., 3 to 30, sometimes 3 to 15, sometimes 3 to 7). In a particular BIC, all of the NAMs may have the same position in the BIC, sequence, length, polarity relative to a bN (e.g., all covalently coupled to a bN in a 5'→3' orientation), internucleotide linkage (e.g., all phosphorothioate), etc. Alternatively, some of the NAMs in a single BIC may differ from others in the same BIC. The following sections, III.2.A-F, describe certain structural and biological properties one or more NAMs in a BIC may have. Additional description is found elsewhere herein.

A. Position of a NAM in a BIC

A NAM can be described in terms of its position in a BIC. For example, a NAM having a free end (free terminal nucleotide) is sometimes referred to as a "prime NAM." A NAM with a free 5'-terminus can be referred to as "5-prime NAM" and a NAM with a free 3'-terminus can be referred to as "3-prime NAM." A NAM with no free end is sometimes referred to as an "internal NAM." It will be appreciated that a single BIC may have 0, 1 or multiple 5-prime NAMs, 0, 1 or multiple 3-prime NAMs, and 0, 1 or multiple internal NAMs.

As noted (and as discussed hereinbelow), the position of a NAM in a BIC, particularly the position of NAMs comprising certain sequence motifs, can influence immunomodulatory activity. In view of this, and to avoid redundancy, each attribute described hereinbelow related to a NAM should be understood to apply not only to NAMs generally, but also independently to each catagory of NAM described herein, just as if each catagory had been individually indicated. For example, the teaching that, in one aspect, a BIC of the invention may comprise at least one NAM with the sequence 5'-TCGACGT-3' should be understood to teach that the following embodiments are contemplated:

A BIC comprising one or more NAMs with the sequence 5'-TCGACGT-3';
A BIC comprising one or more prime NAMs with the sequence 5'-TCGACGT-3';
A BIC comprising one or more 5'-prime NAMs with the sequence 5'-TCGACGT-3';
A BIC comprising one or more 3-prime NAMs with the sequence 5'-TCGACGT-3';
A BIC comprising one or more core NAMs with the sequence 5'-TCGACGT-3';
A BIC comprising one or more peripheral NAMs with the sequence 5'-TCGACGT-3'; and
A BIC comprising one or more internal NAMs with the sequence 5'-TCGACGT-3'; just as if each subgenus had been explicitly recited.

As a second example, the teaching that, in one aspect, a BIC of the invention may contain no NAM longer than 7 nucleotides that comprises the sequence 5'-CG-3' should be understood to teach that the following embodiments are contemplated:

A BIC in which no NAM longer than 7 nucleotides comprises the sequence 5'-CG-3';
A BIC in which no prime NAM longer than 7 nucleotides comprises the sequence 5'-CG-3';
A BIC in which no 5-prime NAM longer than 7 nucleotides comprises the sequence 5'-CG-3';
A BIC in which no 3-prime NAM longer than 7 nucleotides comprises the sequence 5'-CG-3';
A BIC in which no core NAM longer than 7 nucleotides comprises the sequence 5'-TCGACGT-3';
A BIC in which no peripheral NAM longer than 7 nucleotides comprises the sequence 5'-TCGACGT-3'; and
A BIC in which no internal NAM longer than 7 nucleotides comprises the sequence 5'-CG-3'; just as if each subgenus had been explicitly recited.[1]

B. Length of Nucleic Acid Moieties

NAMs are usually from 1 to 100 nucleotides in length, although NAMs>100 nucleotides are not excluded. In various embodiments, a nucleic acid moiety is not more than 50, not more than 30, not more than 15, not more than 10, or not more than 7 nucleotides in length. In various embodiments, a NAM is at least 2 nucleotides in length, often at least 3, at least 4, at least 5, at least 6, at least 7, at least 8, at least 10, at least 20, or at least 30 nucleotides in length. In various embodiments, a NAM has a length in the range, 1 to 20 nucleotides, 2 to 20 nucleotides, 3 to 20 nucleotides, 4 to 20 nucleotides, 5 to 20 nucleotides, 6 to 20 nucleotides, 2 to 7 nucleotides, 3 to 7 nucleotides, 4 to 7 nucleotides, 5 to 7 nucleotides, or 6 to 7 nucleotides.

It is contemplated that, in some embodiments, a BIC will comprise at least one NAM shorter than 8 nucleotides in length (for example, 6 or 7 nucleotides in length). In some embodiments, all of the NAMs in a BIC will be shorter than 8 nucleotides (e.g., having a length in a range defined by a lower limit of 2, 3, 4, 5, of 6 and an independently selected upper limit of 5, 6, or 7 nucleotides, where the upper limit is higher than the lower limit).

C. Sequences and Sequence Motifs

At least one NAM of a BIC comprises at least one 5'-cytosine, guanine-3' (5'-CG-3') sequence, in which the cytosine is not methylated at the C-S position and, preferably is not methylated at any position (hereinafter "CG"[2]). A number of other sequences are provided in this section and, for convenience, any one, or the entire set, of CG-containing sequences and motifs listed in this section can be referred to as a "modulatory sequence(s)."[34]

Often, more than one NAM in a BIC comprises a modulatory sequence, e.g, CG. Sometimes all of the NAMs comprise a modulatory sequence. More often, one or more of the following subsets of NAMs comprise a modulatory sequence: all of the prime NAMs, all of the 5-prime NAMs, all of the 3-prime NAMs, all of the core NAMs, all of the internal NAMs, and all of the peripheral NAMs. Alternatively, at least half (50%) or at least three-quarters (75%) of the NAMs (or, alternatively, an aforementioned subset of NAMs) in a BIC comprise a modulatory sequence. In an embodiment, all, at least half, or at least three-quarters of the NAMs that comprise a modulatory sequence comprise the same sequence.

In one embodiment, at least one nucleic acid moiety in a BIC comprises a modulatory sequence, e.g, CG, and is less than 8 nucleotides in length. In a related embodiment, the BIC contains no NAM that is both longer than 8 nucleotides in length and comprises the sequence "CG," or, alternatively, comprises the sequence "TCG" or "ACG." In an embodiment, at least one nucleic acid moiety in the BIC does not comprise a CG sequence.

In the formulae below, all sequences are in the 5'→3' direction and the following abbreviations are used: B=5-bromocytosine; bU=5-bromouracil; a-A=2-amino-adenine; g=6-thioguanine; t=4-thio-thymine; H=a modified cytosine comprising an electron-withdrawing group, such as halogen in the 5 position; unless indicated otherwise, X=any base. Unless otherwise indicated, in NAM motifs showing multiple X nucleotides, each X is independently selected. In some embodiments, a cytosine (C) in a sequence referred to infra is replaced with N4-ethylcytosine or N4-methylcytosine or 5-hydroxycytosine. In various embodiments, a guanosine (G) in the formula is replaced with 7-deazaguanosine.

In one embodiment, a NAMs is 3 to 7 nucleotides in length. In an embodiment, the nucleic acid moiety comprises the sequence 5'-thymidine, cytosine, guanine-3' (5'-TCG-3'). Examples include, without limitation, the 3-mer TCG, the 4-mer TCGX (e.g., TCGA), the 5-mers TCGXX (e.g., TCGTC and TCGAT), the 6-mers TCGXXX, XTCGXX and TCGTCG, and the 7-mers TCGXXXX, XTCGXXX, XXTCGXX and TCGTCGX.

In one embodiment, the nucleic acid moiety is not more than 7 bases in length and has the sequence 5'-[(X)$_{0-2}$]TCG[(X)$_{2-4}$]-3', or 5'-TCG[(X)$_{2-4}$]-3', or 5'-TCG(A/T)[(X)$_{1-3}$]-3', or 5'-TCG(A/T)CG(A/T)-3', or 5'-TCGACGT-3' or 5'-TCGTCGA-3'. Often, at least one nucleic acid moiety comprises the sequence 5'-TCGA-3' or 5'-TCGACGT-3'.

In some embodiments, a nucleic acid moiety comprises the sequence

5'-ACGTTCG-3';

5'-TCGTCG-3';

5'-AACGTTC-3';

5'-AACGTT-3';

5'-TCGTT-3';

5'-CGTTCG-3';

5'-TCGTCGA-3';

5'-TCGXXX-3';

```
-continued
5'-XTCGXX-3';

5'-XXTCGX-3';

5'-TCGAGA-3';

5'-TCGTTT-3';

5'-TTCGAG-3';

5'-TTCGT-3';

5'-TTCGC-3';

5'-GTCGT-3';

5'-ATCGT-3';

5'-ATCGAT-3';

5'-GTCGTT-3';

5'-GTCGAC-3';

5'-ACCGGT-3';

5'-AABGTT-3';

5'-AABGUT-3';
and

5'-TCGTBG-3'.
```

In some embodiments, a nucleic acid moiety comprises a sequence that is 5'-purine, purine, C, G, pyrimidine, pyrimidine-3'; 5'-purine, purine, C, G, pyrimidine, pyrimidine, C, G-3'; or 5'-purine, purine, C, G, pyrimidine, pyrimidine, C,C-3'; for example,

```
GACGCT;
GACGTC;
GACGTT;
GACGCC;
GACGCU;
GACGUC;
GACGUU;
GACGUT;
GACGTU;
AGCGTT;
AGCGCT;
AGCGTC;
AGCGCC;
AGCGUU;
AGCGCU;
AGCGUC;
AGCGUT;
AGCGTU;
AACGTC;
```

```
-continued
AACGCC;
AACGTT;
AACGCT;
AACGUC;
AACGUU;
AACGCU;
AACGUT;
AACGTU;
GGCGTT;
GGCGCT;
GGCGTC;
GGCGCC;
GGCGUU;
GGCGCU;
GGCGUC;
GGCGUT;
GGCGTU,
AACGTT,
AGCGTC,
GACGTT,
GGCGTT,
AACGTC,
GACGTC,
GGCGTC,
AACGCC,
AGCGCC,
GACGCC,
GGCGCC,
AGCGCT,
GACGCT,
GGCGCT,
GGCGTT,
and
AACGCC.
```

In some embodiments, a nucleic acid moiety comprises the sequence:

```
TCGTCGA;
TCGTCG;
TCGTTT;
TTCGTT;
```

-continued

TTTTCG;

ATCGAT;

GTCGAC;

GTCGTT;

TCGCGA;

TCGTTTT;

TCGTC;

TCGTT;

TCGT;

TCG;

ACGTTT;

CCGTTT;

GCGTTT;

AACGTT;

TCGAAAA;

TCGCCCC;

TCGGGGG;

AACGTTCG;

AACGTTCC;

AACGUTCG;

AABGTTCG;

AABGUTCG
and/or

AABGTTBG.

In some embodiments, a nucleic acid moiety comprises the sequence:

AACGTTCC,

AACGTTCG,

GACGTTCC,
and/or

GACGTTCG.

In some embodiments, a nucleic acid moiety comprises the sequence:

GGCGTTCG;

GGCGCTCG;

GGCGTCCG;

GGCGCCCG;

GACGTTCC;

GACGCTCC;

GACGTCCC;

-continued

GACGCCCC;

AGCGTTCC;

AGCGCTCC;

AGCGTCCC;

AGCGCCCC;

AACGTTCC;

AACGCTCC;

AACGTCCC;

AACGCCCC;

GGCGTTCC;

GGCGCTCC;

GGCGTCCC;

GGCGCCCC;

GACGTTCG;

GACGCTCG;

GACGTCCG;

GACGCCCG;

AGCGTTCG;

AGCGCTCG;

AGCGTCCG;

AGCGCCCG;

AACGTTCG;

AACGCTCG;

AACGTCCG;

AACGCCCG;

GACGCTCC;

GACGCCC;

AGCGTTCC;

AGCGCTCC;

AGCGTCCC;

AGCGCCCC;

AACGTCCC;

AACGCCCC;

GGCGTTCC;

GGCGCTCC;

GGCGTCCC;

GGCGCCCC;

GACGCTCG;

GACGTCCG;

GACGCCCG;

-continued
```
AGCGTTCG;

AGCGTCCG;

AGCGCCCG;

AACGTCCG;

AACGCCCG.
```

In various embodiments, a nucleic acid moiety comprises the motif 5'-$X_1X_2AX_3CGX_4TCG$-3' (SEQ ID NO:4) wherein $X_1$ is T, G, C or B, wherein $X_2$ is T, G, A or U, wherein $X_3$ is T, A or C, wherein $X_4$ is T, G or U and wherein the sequence is not 5'-TGAACGTTCG-3' (SEQ ID NO:5) or 5'-GGAACGTTCG-3' (SEQ ID NO:6). Examples include:

```
TGAACGUTCG;            (SEQ ID NO:7)

TGACCGTTCG;            (SEQ ID NO:8)

TGATCGGTCG;            (SEQ ID NO:9)

TGATCGTTCG;            (SEQ ID NO:10)

TGAACGGTCG;            (SEQ ID NO:11)

GTAACGTTCG;            (SEQ ID NO:12)

GTATCGGTCG;            (SEQ ID NO:13)

GTACCGTTCG;            (SEQ ID NO:14)

GAACCGTTCG;            (SEQ ID NO:15)

BGACCGTTCG             (SEQ ID NO:16)

CGAACGTTCG;            (SEQ ID NO:17)

CGACCGTTCG             (SEQ ID NO:18)

BGAACGTTCG;            (SEQ ID NO:19)

TTAACGUTCG;            (SEQ ID NO:20)

TUAACGUTCG             (SEQ ID NO:21)
and

TTAACGTTCG.            (SEQ ID NO:22)
```

In various embodiments, a nucleic acid moiety comprises a sequence:

```
5'-TCGTCGAACGTTCGTTAACGTTCG-3';       (SEQ ID NO:23)

5'-TGACTGTGAACGUTCGAGATGA-3';         (SEQ ID NO:24)

5'-TCGTCGAUCGUTCGTTAACGUTCG-3';       (SEQ ID NO:25)

5'-TCGTCGAUCGTTCGTUAACGUTCG-3';       (SEQ ID NO:26)

5'-TCGTCGUACGUTCGTTAACGUTCG-3';       (SEQ ID NO:27)

5'-TCGTCGAa-ACGUTCGTTAACGUTCG-3'⁵;    (SEQ ID NO:28)

5'-TGATCGAACGTTCGTTAACGTTCG-3;        (SEQ ID NO:29)

5'-TGACTGTGAACGUTCGGTATGA-3';         (SEQ ID NO:30)

5'-TGACTGTGACCGTTCGGTATGA-3';         (SEQ ID NO:31)

5'-TGACTGTGATCGGTCGGTATGA-3';         (SEQ ID NO:32)

5'-TCGTCGAACGTTCGTT-3';               (SEQ ID NO:33)

5'-TCGTCGTGAACGTTCGAGATGA-3';         (SEQ ID NO:34)

5'-TCGTCGGTATCGGTCGGTATGA-3';         (SEQ ID NO:35)

5'-CTTCGAACGTTCGAGATG-3';             (SEQ ID NO:36)

5'-CTGTGATCGTTCGAGATG-3';             (SEQ ID NO:37)

5'-TGACTGTGAACGGTCGGTATGA-3';         (SEQ ID NO:38)

5'-TCGTCGGTACCGTTCGGTATGA-3';         (SEQ ID NO:39)

5'-TCGTCGGAACCGTTCGGAATGA-3';         (SEQ ID NO:40)

5'-TCGTCGAACGTTCGAGATG-3';            (SEQ ID NO:41)

5'-TCGTCGTAACGTTCGAGATG-3';           (SEQ ID NO:42)

5'-TGACTGTGACCGTTCGGAATGA-3';         (SEQ ID NO:43)

5'-TCGTCGAACGTTCGAACGTTCG-3';         (SEQ ID NO:44)

5'-TBGTBGAACGTTCGAGATG-3';            (SEQ ID NO:45)

5'-TCGTBGAACGTTCGAGATG-3';            (SEQ ID NO:46)

5'-TCGTCGACCGTTCGGAATGA-3';           (SEQ ID NO:47)

5'-TBGTBGACCGTTCGGAATGA-3';           (SEQ ID NO:48)

5'-TCGTBGACCGTTCGGAATGA-3';           (SEQ ID NO:49)

5'-TTCGAACGTTCGTTAACGTTCG-3';         (SEQ ID NO:50)

5'-CTTBGAACGTTCGAGATG-3';             (SEQ ID NO:51)

5'-TGATCGTCGAACGTTCGAGATG-3'.         (SEQ ID NO:52)
```

In some embodiments, a nucleic acid moiety comprises the sequence: 5'-$X_1X_2AX_3BGX_4TCG$-3' (SEQ ID NO:53), wherein $X_1$ is T, G, C or B, wherein $X_2$ is T, G, A or U, wherein $X_3$ is T, A or C, wherein $X_4$ is T, G or U. In some embodiments, the nucleic acid moiety is not 5'-TGAABGTTCG-3' (SEQ ID NO:54). Examples include:

```
TGAABGUTCG;            (SEQ ID NO:55)

TGACBGTTCG;            (SEQ ID NO:56)

TGATBGGTCG;            (SEQ ID NO:57)

GTATBGGTCG;            (SEQ ID NO:58)

GTACBGTTCG;            (SEQ ID NO:59)

GAACBGTTCG;            (SEQ ID NO:60)

GAAABGUTCG;            (SEQ ID NO:61)

BGACBGTTCG;            (SEQ ID NO:62)

CGAABGTTCG;            (SEQ ID NO:63)

BGAABGTTCG;            (SEQ ID NO:64)

BGAABGUTCG;            (SEQ ID NO:65)

TTAABGUTCG;            (SEQ ID NO:66)

TUAABGUTCG;            (SEQ ID NO:67)
and

TTAABGTTCG.            (SEQ ID NO:68)
```

In some embodiments, a nucleic acid moiety comprises the sequence:

```
5'-TGACTGTGAABGUTCGAGATGA-3';          (SEQ ID NO:69)

5'-TCGTCGAABGTTCGTTAABGTTCG-3';        (SEQ ID NO:70)

5'-TGACTGTGAABGUTCGGTATGA-3';          (SEQ ID NO:71)

5'-TGACTGTGAABGUTCGGAATGA-3';          (SEQ ID NO:72)

5'-TCGTCGGAAABGUTCGGAATGA-3';          (SEQ ID NO:73)
and/or

5'-TCGTBGAABGUTCGGAATGA-3'.            (SEQ ID NO:74)
```

In some embodiments, a nucleic acid moiety comprises the sequence: 5'-$X_1X_2AX_3CGX_4$TCG-3' (SEQ ID NO:75) wherein $X_1$ is T, C or B, wherein $X_2$ is T, G, A or U, wherein $X_3$ is T, A or C, wherein $X_4$ is T, G or U. In some embodiments, the formula is not 5'-TGAACGTTCG-3' (SEQ ID NO:5)

In other embodiments, the nucleic acid moiety comprises the sequence:

```
5'-TGACTGTGAABGTTCGAGATGA-3';          (SEQ ID NO:76)
5'-TGACTGTGAABGTTBGAGATGA-3';          (SEQ ID NO:77)
5'-TGACTGTGAABGTTCCAGATGA-3';          (SEQ ID NO:78)
5'-TGACTGTGAACGTUCGAGATGA-3';          (SEQ ID NO:79)
5'-TGACTGTGAACGbUTCGAGATGA-3';         (SEQ ID NO:80)
5'-TGACTGTGAABGTTCGTUATGA-3';          (SEQ ID NO:81)
5'-TGACTGTGAABGTTCGGTATGA-3';          (SEQ ID NO:82)
5'-CTGTGAACGTTCGAGATG-3';              (SEQ ID NO:83)
5'-TBGTBGTGAACGTTCGAGATGA-3';          (SEQ ID NO:84)
5'-TCGTBGTGAACGTTCGAGATGA-3';          (SEQ ID NO:85)
5'-TGACTGTGAACGtTCGAGATGA-3';          (SEQ ID NO:86)
5'-TGACTGTGAACgTTCgAGATGA-3';          (SEQ ID NO:87)
5'-TGACTGTGAACGTTCGTUATGA-3';          (SEQ ID NO:88)
5'-TGACTGTGAACGTTCGTTATGA-3';          (SEQ ID NO:89)
5'-TCGTTCAACGTTCGTTAACGTTCG-3';        (SEQ ID NO:90)
5'-TGATTCAACGTTCGTTAACGTTCG-3';        (SEQ ID NO:91)
5'-CTGTCAACGTTCGAGATG-3';              (SEQ ID NO:92)
5'-TCGTCGGAACGTTCGAGATG-3';            (SEQ ID NO:93)
5'-TCGTCGGACGTTCGAGATG-3';             (SEQ ID NO:94)
5'-TCGTCGTACGTTCGAGATG-3';             (SEQ ID NO:95)
5'-TCGTCGTTCGTTCGAGATG-3'.             (SEQ ID NO:96)
```

In some embodiments, with respect to any of the sequences disclosed supra, the nucleic acid moiety further comprises one, two, three or more TCG and/or TBG and/or THG, sequences, preferably 5' to the sequence provided supra. The TCG(s) and/or TBG(s) may or may not be directly adjacent to the sequence shown. For example, in some embodiments, a nucleic acid moiety includes any of the following:

```
5'-TCGTGAACGTTCG-3';                   (SEQ ID NO:97)
5'-TCGTCGAACGTTCG-3';                  (SEQ ID NO:98)
5'-TBGTGAACGTTCG-3';                   (SEQ ID NO:99)
5'-TBGTBGAACGTTCG-3';                  (SEQ ID NO:100)
5'-TCGTTAACGTTCG-3'.                   (SEQ ID NO:101)
```

In some embodiments, the additional TCG and/or TBG sequence(s) lie immediately 5' and adjacent to the reference sequence. In other embodiments, there is a one or two base separation.

In some embodiments, a NAM has the sequence: 5'-$(TCG)_w N_y AX_3 CGX_4 TCG$-3' (SEQ ID NOS: 102 and 145) wherein w is 1-2, wherein y is 0-2, wherein N is any base, wherein $X_3$ is T, A or C, wherein $X_4$ is T, G or U.

In some embodiments, the NAM comprises any of the following sequences:

```
TCGAACGTTCG;                           (SEQ ID NO:103)
TCGTCGAACGTTCG;                        (SEQ ID NO:104)
TCGTGAACGTTCG;                         (SEQ ID NO:105)
TCGGTATCGGTCG;                         (SEQ ID NO:106)
TCGGTACCGTTCG;                         (SEQ ID NO:107)
TCGGAACCGTTCG;                         (SEQ ID NO:108)
TCGGAACGTTCG;                          (SEQ ID NO:109)
TCGTCGGAACGTTCG;                       (SEQ ID NO:110)
TCGTAACGTTCG;                          (SEQ ID NO:111)
TCGACCGTTCG;                           (SEQ ID NO:112)
TCGTCGACCGTTCG;                        (SEQ ID NO:113)
TCGTTAACGTTCG.                         (SEQ ID NO:114)
```

In some embodiments, a nucleic acid moiety comprises any of the following sequences: 5'-$(TBG)_z N_y AX_3 CGX_4 TCG$-3' (SEQ ID NOS: 115 and 146) wherein z is 1-2, wherein y is 0-2, wherein B is 5-bromocytosine, wherein N is any base, wherein $X_3$ is T, A or C, wherein $X_4$ is T, G or U.

In some embodiments, a nucleic acid moiety comprises:

```
TBGTGAACGTTCG;                         (SEQ ID NO:116)
TBGTBGTGAACGTTCG;                      (SEQ ID NO:117)
TBGAACGTTCG;                           (SEQ ID NO:118)
TBGTBGAACGTTCG;                        (SEQ ID NO:100)
TBGACCGTTCG;                           (SEQ ID NO:119)
TBGTBGACCGTTCG.                        (SEQ ID NO:120)
```

In some embodiments, a nucleic acid moiety comprises any of the following sequences: 5'-$TCGTBGN_y AX_3 CGX_4 TCG$-3' (SEQ ID NO:121) wherein y is 0-2, wherein B is 5-bromocytosine, wherein N is any base, wherein $X_3$ is T, A or C, wherein $X_4$ is T, G or U. In some embodiments, the nucleic acid moiety comprises any of the following sequences:

```
TCGTBGTGAACGTTCG;      (SEQ ID NO:122)
TCGTBGAACGTTCG;        (SEQ ID NO:123)
TCGTBGACCGTTCG.        (SEQ ID NO:124)
```

In some embodiments, a nucleic acid moiety comprises any of the following sequences: 5'-(TCG)$_w$-N$_y$AX$_3$BGX$_4$TCG-3' (SEQ ID NOS: 125 and 147) wherein w is 1-2, wherein y is 0-2, wherein N is any base, wherein $X_3$ is T, A or C, wherein $X_4$ is T, G or U. In some embodiments, the nucleic acid moiety comprises any of the following sequences: TCGGAAABGTTCG (SEQ ID NO:126) or TCGAABGTTCG (SEQ ID NO:127).

In some embodiments, a nucleic acid moiety comprises any of the following sequences: 5'-(TBG)$_z$-N$_y$AX$_3$BGX$_4$TCG-3' (SEQ ID NOS: 128 and 148) wherein z is 1-2, wherein y is 0-2, wherein B is 5-bromocytosine, wherein N is any base, wherein $X_3$ is T, A or C, wherein $X_4$ is T, G or U. In some embodiments, the nucleic acid moiety comprises any of the following sequences: TBGAABGUTCG (SEQ ID NO:129) or TBGAABGTTCG (SEQ ID NO:130).

In some embodiments, a nucleic acid moiety comprises any of the following sequences: 5'-TCGTBGN$_y$AX$_3$BGX$_4$TCG-3' (SEQ ID NO:131) wherein y is 0-2, wherein B is 5-bromocytosine, wherein N is any base, wherein $X_3$ is T, A or C, wherein $X_4$ is T, G or U. In some embodiments, the nucleic acid moiety comprises any of the following sequences: TCGTBGAABGUTCG (SEQ ID NO:132) or TCGTBGAABGTTCG (SEQ ID NO:133).

In some embodiments, a nucleic acid moiety comprises an RNA of the sequence AACGUUCC, AACGUUCG, GACGUUCC, and GACGUUCG.

In an embodiment, the nucleic acid moiety has the formula 5'-TCG[(X)$_{2-4}$]-3' or 5'-TCG(A/T)[(X)$_{1-3}$] or 5'-TCG(A/T)CG(A/T)-3' or 5'-TCGACGT-3' (where each X is an independently selected nucleotide).

In one embodiment, a nucleic acid moiety comprises a sequence 5'-TCGTCGA-3'. In one embodiment, a nucleic acid moiety comprises a sequence selected from:

```
TCGXXXX,
TCGAXXX,
XTCGXXX,
XTCGAXX,
TCGACGT,
TCGAACG,
TCGAGAT,
TCGACTC,
TCGAGCG,
TCGATTT,
TCGCTTT,
TCGGTTT,
TCGTTTT,
TCGTCGT,
ATCGATT,
TTCGTTT,
TTCGATT,
ACGTTCG,
AACGTTC,
TGACGTT,
TGTCGTT,
TCGXXX,
TCGAXX,
GTCGTT,
GACGTT,
ATCGAT,
TCGTCG;
TCGTTT;
TCGAGA;
TTCGAG;
TTCGTT;
AACGTT;
AACGTTCG;
AACGUTCG,
ABGUTCG,
TCGXX,
TCGAX,
TCGAT,
TCGTT,
TCGTC;
TCGA,
TCGT, and
```

TCGX (where X is A, T, G or C; U is 2'-deoxyuridine and B is 5-bromo-2'-deoxycytidine).

In one embodiment, the nucleic acid moiety is a 7-mer having the sequence

```
TCGXXXX,
TCGAXXX,
XTCGXXX,
XTCGAXX,
TCGTCGA,
TCGACGT,
```

-continued

TCGAACG,

TCGAGAT,

TCGACTC,

TCGAGCG,

TCGATTT,

TCGCTTT,

TCGGTTT,

TCGTTTT,

TCGTCGT,

ATCGATT,

TTCGTTT,

TTCGATT,

ACGTTCG,

AACGTTC,

TGACGTT, or

TGTCGTT;

or is a 6-mer having the sequence

TCGXXX,

TCGAXX,

TCGTCG,

AACGTT,

ATCGAT,

GTCGTT, or

GACGTT;

or is a 5-mer having the sequence

TCGXX,

TCGAX,

TCGAT,

TCGTT, or

TCGTC;

or is a 4-mer having the sequence

TCGA,

TCGT, or

TCGX, where X is A, T, G or C,
or is a 3-mer having the sequence TCG.

In some embodiments, a nucleic acid moiety has a sequence comprising a sequence or sequence motif described in copending coassigned U.S. patent application Ser. No. 09/802,685iii (published as U.S. application Publication No. 20020028784A1 on Mar. 7, 2002 and as WO 01/68077 on Sep. 20, 2001); Ser. No. 09/802,359 (published as WO 01/68144 on Sep. 20, 2001), and copending U.S. application Ser. No. 10/033,243, or in PCT publications WO 97/28259, WO 98/16247; WO 98/55495; WO 99/11275; WO 99/62923; and WO 01/35991.[iv, v] In one embodiment, at least one nucleic acid moiety of a BIC comprises a TG sequence or a pyrimidine-rich (e.g., T-rich or C-rich) sequence, as described in PCT publication WO 01/22972.

It will be appreciated that a single NAM may comprise more than one iteration of a modulatory sequence and/or may comprise two or more different modulatory sequences. The modulatory sequences within a single NAM can be adjacent, overlapping, or separated by additional nucleotide bases within the NAM.

In an embodiment, a NAM includes one or more palindromic regions. In the context of single-stranded sequences, the term "palindromic" refers to a sequence that would be palindromic if it was double stranded (i.e., complexed with a complementary sequence to form a double-stranded molecule). In one embodiment, one NAM has a sequence that is palindromic or partially palindromic in relation to a second NAM in the BIC. In an embodiment of the invention, the sequence of one or more of the nucleic acid moieties of a BIC is not palindromic. In an embodiment of the invention, the sequence of one or more NAMs (e.g., all, or all of a NAM subgroup) of a BIC does not include a palindromic sequence greater than four bases, optionally greater than 6 bases.

D. Position of Modulatory Sequences

In referring to the position of a sequence motif in a NAM of a BIC, the following terminology can be used: Within a NAM, a sequence or motif is in "the 5-prime position" of the NAM when there are no nucleotides in the NAM that are 5' to the specified sequence. Thus, in a NAM with the sequence 5'-TC-GACGT-3', the sequences T, TC, TCG and TCGA, are in "the 5-prime position," while the sequence "GAC" is not.[vi] A NAM with a free 5' end (i.e., a 5-prime NAM; see § III(2)(A), supra) can be designated using the symbol "$5'^F$" to the left of the formula for the base sequence of the NAM. As used herein, the term "free 5' end" in the context of a nucleic acid moiety has its usual meaning and means that the 5' terminus of the nucleic acid moiety is not conjugated to an other nucleotide, spacer moiety, or other blocking group or functional group. The free 5'-nucleoside contains an unmodified 5'-hydroxy group or a 5'-phosphate, 5'-diphosphate, or 5'-triphosphate group, or other common modified phosphate groups (such as thiophosphate, dithiophosphate, and the like) that is not further linked to a blocking or functional group.

In one embodiment, a BIC of the invention contains at least one NAM with the sequence 5'-X-CG-Y-3' where X is zero, one, or two nucleotides and Y is 3, 4, 5, 6, 7, 8, 9, 10, 11, 12, 13, 14, 15 or more than 15 nucleotides in length. In an embodiment, the 5'-X-CG-Y-3' sequence is in one or more 5-prime NAMs of the BIC, e.g., the 5-prime positions of one or more 5-prime NAM. In an embodiment, the BIC contains 2, 3 or more nucleic acid moieties with a sequence having the formula 5'-X-CG-Y-3' sequence. For example, in an embodiment, all of the nucleic acid moieties of the BIC have sequences of the formula 5'-X-CG-Y-3' sequence.

In various embodiments, a BIC of the invention comprises at least 1, at least 2, at least 3, at least 4, or at least 5 free 5'ends. In some embodiments, the number of free 5'-ends is from 1 to 25, from 1 to 10, from 10 to 25, from 2 to 6, from 3 to 5, or from 4 to 5.

E. Structure of the Nucleic Acid Moiety

A nucleic acid moiety of a BIC may contain nucleotides with a structural modifications relative to naturally occurring nucleic acids. Modifications include any known in the art for polynucleotides, but are not limited to, modifications of the 3'OH or 5'OH group, modifications of the nucleotide base, modifications of the sugar component, and modifications of the phosphate group. Various such modifications are described below.

The nucleic acid moiety may be DNA, RNA or mixed DNA/RNA, single stranded, double stranded or partially double stranded, and may contain other modified polynucleotides. A nucleic acid moiety may contain naturally-occurring or modified, non-naturally occurring bases, and may contain modified sugar, phosphate, and/or termini. For example, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. Preferably, nucleic acid moieties of the present invention comprise phosphorothioate backbones. Sugar modifications known in the field, such as 2'-alkoxy-RNA analogs, 2'-amino-RNA analogs and 2'-alkoxy- or amino-RNA/DNA chimeras and others described herein, may also be made and combined with any phosphate modification.

The nucleic acid moiety can also contain phosphate-modified nucleotides. Synthesis of nucleic acids containing modified phosphate linkages or non-phosphate linkages is also know in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group) which can be attached to the sugar or sugar analog moiety in the nucleic acids of the present invention can be a monophosphate, diphosphate, triphosphate, alkylphosphonate, phosphorothioate, phosphorodithioate, phosphoramidate or the like. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841-1848; Chaturvedi et al. (1996) *Nucleic Acids Res.* 24:2318-2323; and Schultz et al. (1996) *Nucleic Acids Res.* 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165-190). Similarly the synthesis of other phosphate analogs, such as phosphotriester (Miller et al. (1971) *JACS* 93:6657-6665), non-bridging phosphoramidates (Jager et al. (1988) *Biochem.* 27:7247-7246), N3' to P5' phosphoramidiates (Nelson et al. (1997) *JOC* 62:7278-7287) and phosphorodithioates (U.S. Pat. No. 5,453,496) has also been described. Other non-phosphorous based modified nucleic acids can also be used (Stirchak et al. (1989) *Nucleic Acids Res.* 17:6129-6141). Nucleic acids with phosphorothioate backbones appear to be more resistant to degradation after injection into the host. Braun et al. (1988) *J. Immunol.* 141:2084-2089; and Latimer et al. (1995) *Mol. Immunol.* 32:1057-1064.

Nucleic acid moieties used in the invention can comprise ribonucleotides (containing ribose as the only or principal sugar component), and/or deoxyribonucleotides (containing deoxyribose as the principal sugar component). Modified sugars or sugar analogs can be incorporated in the nucleic acid moiety. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. The sugar moiety is preferably the furanoside of ribose, deoxyribose, arabinose or 2'-0-alkylribose, and the sugar can be attached to the respective heterocyclic bases either in α or β anomeric configuration. Sugar modifications include, but are not limited to, 2'-alkoxy-RNA analogs, 2'-amino-RNA analogs and 2'-alkoxy- or amino-RNA/DNA chimeras. For example, a sugar modification in the BIC includes, but is not limited to, 2'-amino-2'-deoxyadenosine. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of a BIC.

The heterocyclic bases, or nucleic acid bases, which are incorporated in the nucleic acid moiety can be the naturally-occurring principal purine and pyrimidine bases, (namely uracil, thymine, cytosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the nucleic acid moiety can include one or several heterocyclic bases other than the principal five base components of naturally-occurring nucleic acids. Preferably, however, the heterocyclic base is, without limitation, uracil-5-yl, cytosin-5-yl, adenin-7-yl, adenin-8-yl, guanin-7-yl, guanin-8-yl, 4-aminopyrrolo[2.3-d]pyrimidin-5-yl, 2-amino-4-oxopyrolo[2,3-d]pyrimidin-5-yl, or 2-amino-4-oxopyrrolo[2.3-d]pyrimidin-3-yl groups, where the purines are attached to the sugar moiety of the nucleic acid moiety via the 9-position, the pyrimidines via the 1-position, the pyrrolopyrimidines via the 7-position and the pyrazolopyrimidines via the 1-position.

The nucleic acid moiety may comprise at least one modified base. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs."

Examples of base modifications include, but are not limited to, addition of an electron-withdrawing moiety to C-5 and/or C-6 of a cytosine of the nucleic acid moiety. Preferably, the electron-withdrawing moiety is a halogen. Such modified cytosines can include, but are not limited to, azacytosine, 5-bromocytosine, 5-chlorocytosine, chlorinated cytosine, cyclocytosine, cytosine arabinoside, 5-fluorocytosine, fluoropyrimidine, 5,6-dihydrocytosine, 5-iodocytosine, 5-nitrocytosine, and any other pyrimidine analog or modified pyrimidine. Other examples of base modifications include, but are not limited to, addition of an electron-withdrawing moiety to C-5 and/or C-6 of a uracil of the nucleic acid moiety. Preferably, the electron-withdrawing moiety is a halogen. Such modified uracils can include, but are not limited to, 5-bromouracil, 5-chlorouracil, 5-fluorouracil, 5-iodouracil. See, for example, PCT Application No. WO 99/62923. Also see, Kandimalla et al., 2001, Bioorg. Med. Chem. 9:807-13.

Other examples of base modifications include the addition of one or more thiol groups to the base including, but not limited to, 6-thio-guanine, 4-thio-thymine and 4-thio-uracil.

F. "Isolated Immunomodulatory Activity" and "Inferior Immunomodulatory Activity"

One property of a nucleic acid moiety is the "isolated immunomodulatory activity" associated with the nucleotide sequence of the NAM.

In some embodiments, a nucleic acid moiety of a BIC does not have "isolated immunomodulatory activity," or has "inferior isolated immunomodulatory activity," (i.e., when compared to the BIC), as described below.

The "isolated immunomodulatory activity" of a nucleic acid moiety is determined by measuring the immunomodulatory activity of an isolated polynucleotide having the primary sequence of the nucleic acid moiety, and having the same nucleic acid backbone (e.g., phosphorothioate, phosphodiester, chimeric). For example, a BIC having the structure:

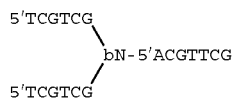

contains three nucleic acid moieties. To determine the independent immunomodulatory activity of, for example, the nucleic acid moiety in the BIC having the sequence 5'-TCGTCG-3, a test polynucleotide having the same sequence (i.e., 5'-TCGTCG-3') and same backbone structure (e.g., phosphorothioate) is synthesized and its immunomodulatory activity (if any) is measured. Immunomodulatory activity can be determined using standard assays which indicate various aspects of the immune response, such as those described in §9, infra. Preferably the human PBMC assay described in §9, infra, is used. As discussed infra, to account for donor variation, typically the assay is carried out using cells obtained from multiple donors. A polynucleotide does not have immunomodulatory activity (and the corresponding nucleic acid moiety does not have "isolated immunomodulatory activity") when the amount of IFN-γ secreted by PBMCs contacted with the polynucleotide is not significantly greater (e.g., less than about 2-fold greater) in the majority of donors than in the absence of the test compound or, (in some embodiments) in the presence of an inactive control compound (e.g., 5'-TGACTGTGAACCTTAGAGATGA-3' (SEQ ID NO:3).)

To compare the immunomodulatory activity of a BIC and an isolated polynucleotide, immunomodulatory activity is measured, preferably using the human PBMC assay described in §9, infra. Usually, the activity of two compounds is compared by assaying them in parallel under the same conditions (e.g., using the same cells), usually at a concentration of about 20 µg/ml. As noted supra, typically, concentration is determined by measuring absorbance at 260 nm and using the conversion 0.5 $OD_{260}$/ml=20 µg/ml. This normalizes the amount of total nucleic acid in the test sample. Alternatively, concentration or weight can be measured by other methods known in the art. If desired, the amount of nucleic acid moiety can be determined by measuring absorbance at 260, and the weight of the BIC calculated using the molecular formula of the BIC. This method is sometimes used when the ratio of weight contributed a spacer moiety(s) to weight contributed by the NAMs in a BIC is high (i.e., greater than 1).

Alternatively, a concentration of 3 µM may be used, particularly when the calculated molecular weights of two samples being compared differ by more than 20%.

A nucleic acid moiety of a BIC is characterized as having "inferior immunomodulatory activity," when the test polynucleotide has less activity than the BIC to which it is compared. Preferably the isolated immunomodulatory activity of the test polynucleotide is no more than about 50% of the activity of the BIC, more preferably no more than about 20%, most preferably no more than about 10% of the activity of the BIC, or in some embodiments, even less.

For BICs with multiple (e.g., multiple different) nucleic acid moieties, it is also possible to determine the immunomodulatory activity (if any) of a mixture of test polynucleotides, corresponding to the multiple nucleic acid moieties. The assay can be carried out using a total amount of test polynucleotide (i.e., in the mixture) which equals the amount of BIC used. Alternatively, an amount of each test polynucleotide, or each different test polynucleotide, in the mixture can be equal to the amount of the BIC in the assay. As noted in §8, to account for donor variation, preferably assays and analysis use PMBCs from multiple donors.

In one embodiment, one or more (e.g., at least about 2, at least about 4, or at least about 25%, at least about 50%, or all, measured individually or, alternatively, in combination) of the nucleic acid moieties in a BIC do not have isolated immunomodulatory activity. In one embodiment, one or more (e.g., at least about 2, at least about 4, or at least about 25%, at least about 50%, or all, measured individually or, alternatively, in combination) has inferior isolated immunomodulatory activity compared to the BIC.

In a related embodiment, a BIC comprises one or more nucleic acid moieties with isolated immunomodulatory activity. For example, in some embodiments, all or almost all (e.g., at least 90%, preferably at least 95%) of the nucleic acid moieties has isolated immunomodulatory activity. Thus, in a particular BIC, the number of nucleic acid moieties that have isolated immunomodulatory activity can be zero (0), one (1), 2 or more, 3 or more, fewer than 3, 4 or more, fewer than 4, 5 or more, fewer than 5, at least 10, or at least about 20, all, or less than all, of the NAMs, prime NAMs, 5-prime NAMS, or 3-prime NAMs of the BIC.

3. Branch-Point Nucleosides

The branch-point nucleosides of BICs are nucleoside monomers that comprise three or more branch points to which NAMs and/or other bNs are covalently coupled. A "branch point" on a nucleoside is a site where either a core nucleic acid moiety or another branch-point nucleoside is linked to the nucleoside. Thus, each branch-point nucleoside is linked to at least three moieties selected from nucleic acid moieties and branch-point nucleosides. Each of the three moieties is linked to a different position on the branch-point nucleoside.

Each branch-point nucleoside comprises a sugar molecule joined to a nitrogenous base. Although the sugar is typically a 5-carbon sugar, the sugar may optionally be a 6-carbon sugar. In one embodiment, the sugar is ribose or 2'-deoxyribose. Modified sugars or sugar analogs can also be incorporated in the nucleic acid moiety. Thus, in addition to ribose and deoxyribose, the sugar moiety can be pentose, deoxypentose, hexose, deoxyhexose, glucose, arabinose, xylose, lyxose, or a sugar "analog" cyclopentyl group. The sugar can be in pyranosyl or in a furanosyl form. The sugar moiety is optionally the furanoside of ribose, deoxyribose, arabinose or 2'-O-alkoxyribose, and the sugar can be attached to the respective heterocyclic bases either in α or β anomeric configurations.

Sugar modifications include, but are not limited to, 2'-alkoxyribose and 2'-aminoribose analogs.

The base that is incorporated in the nucleic acid moiety can be a naturally-occurring purine or pyrimidine base, (namely uracil, thymine, cytosine, adenine and guanine, as mentioned above), as well as naturally-occurring and synthetic modifications of those principal bases.

Those skilled in the art will recognize that a large number of synthetic non-natural nucleosides comprising various heterocyclic bases and various sugar moieties (and sugar analogs) are known in the art, and that as long as other criteria of the present invention are satisfied, a bN may include a heterocyclic base other than the principal five base components of naturally-occurring nucleic acids. In one embodiment, the heterocyclic base is uracil-5-yl, cytosin-5-yl, adenin-7-yl, adenin-8-yl, guanin-7-yl, guanin-8-yl, 4-aminopyrrolo[2.3-d]pyrimidin-5-yl, 2-amino-4-oxopyrolo[2,3-d]pyrimidin-5-yl, or 2-amino-4-oxopyrrolo[2.3-d]pyrimidin-3-yl groups, where the purines are attached to the sugar moiety of the nucleic acid moiety via the 9-position, the pyrimidines via the 1-position, the pyrrolopyrimidines via the 7-position and the pyrazolopyrimidines via the 1-position.

The bN may comprise a modified base. As used herein, the term "modified base" is synonymous with "base analog", for example, "modified cytosine" is synonymous with "cytosine analog." Similarly, "modified" nucleosides are herein defined as being synonymous with nucleoside "analogs." Examples of base modifications include the addition of one or more thiol groups to the base including, but not limited to, 6-thio-guanine, 4-thio-thymine and 4-thio-uracil.

In addition, nucleosides suited for synthesis of branch-point nucleosides may be purchased (Biosearch Technologies, Inc.; Glen Research, Inc.) or synthesized (see, infra). Typically these bN precursors have protecting groups (e.g., levulinyl, 4,4'-dimethoxytrityl [DMT], fluorenylmethyloxycarbonyl [Fmoc], cyanoethyl [CE]) that allow deprotection of reactive sites during BIC synthesis. Frequently, the bN precursors have SM components (e.g., 6-hydroxy-1-amino-hexyl-3(E)-acrylamido linked at the C-5 position of 2'-deoxyuridine; see FIG. 1A) to which a NAM or additional spacer moiety components may be attached (e.g., via an ester linkage or other linkage). (See § III(4), infra).

In a BIC of the invention, moieties that are covalently coupled to a bN may be linked to a variety of positions on the branch-point nucleoside. For instance, nucleic acid moieties and additional branch-point nucleosides may be linked to positions on either the sugar or base of the branch-point nucleosides. Optionally, all of the branch point positions on the branch-point nucleoside of a BIC are on the sugar moiety of the branch-point nucleoside. Alternatively, one or more of the branch point positions may be on the base of the branch-point nucleoside.

In one embodiment, the branch-point nucleoside is a ribonucleoside or a 2'-deoxyribonucleoside. In an alternative embodiment, the sugar of the branch-point nucleoside may be a modified sugar or a sugar analog, as described above. For instance, instead of ribose, the sugar moiety may be 2-methyl-β-D-arabinofuranosyl. The synthesis and use of a protected 1-(2-methyl-β-D-arabinofuranosyl) uracil phosphoramidite to prepare branched oligonucleotides is described in Von Buren, et al., 1995, *Tetrahedron*, 51:8491-8506.

In one embodiment, a branch-point nucleoside of a BIC is a ribonucleoside and NAMs or bNs are linked to the ribonucleoside at the 2'-, 3'- and/or 5'-hydroxyl positions of the ribonucleoside.

The synthesis and use of reagents suitable for making a BIC comprising a ribonucleoside as the branch-point nucleoside with branch points at the 2'-, 3'- or 5'-hydroxyl positions of the ribonucleoside are known to those of ordinary skill in the art. For instance, the synthesis of an adenosine bisphosphoramidite is described in Damha and Oglivie, *J. Org. Chem*, 1988, 53: 3710. The use of the adenosine bisphosphoramidite in synthesizing branched nucleic acid molecules is described in Hudson and Damha, *J. Am. Chem. Soc.*, 1993, 115:2119-2124, Damha and Zabarylo, *Tetrahedron Letters*, 1989, 30: 6295-6298, and Damha et al., *Tetrahedron Letters*, 1992, 20: 6565-6573. The use of 2'-silyl-protected adenosine phosphoramidites to synthesize branched nucleic acid molecules has also been described (see, for instance, Braich and Damha, *Bioconjugate Chem.*, 1997, 8:370-377, and Kierzek, et al., *Nucleic Acids Research*, 1986, 14:4751-4764). Sproat et al., *Chem. Soc. Perkin Trans. I*, 1994, 4:419-431, describes the synthesis and use of 5'-phosphoramidites (adenosine, guanosine, uracil, and cytidine) to create branched oligoribonucleotides. In another example, a combination of 2'-, 3'-, and 5'-linkages may also be achieved with the branch-point nucleoside resulting from use of a 1-(2-methyl-β-D-arabinofuranosyl)uracil phosphoramidite like that disclosed in Von Buren, et al., 1995, *Tetrahedron*, 51:8491-8506. The synthesis and use of a modified uridine phosphoramidite comprising methoxyoxalamido groups attached through the 2'-position is described in Polushin, *Collection Symposium Series*, 1999, 2:145-150.

Accordingly, in one embodiment, a BIC of this invention comprises a ribonucleoside (bN), a first NAM linked to the 2'-hydroxyl of the ribonucleoside, a second NAM linked to the 3'-hydroxyl of the ribonucleoside, and a third NAM linked to the 5'-hydroxyl of the ribonucleoside.

In another embodiment, the BIC comprises a 2'-deoxyribonucleoside (bN) to which a first moiety (bN or NAM) is linked to the 3'-hydroxyl position of the bN, a second moiety is linked to the 5'-hydroxyl position, and a third moiety is linked to the 5'-C, 4'-C, or 3'-C position of the bN. Accordingly, in one embodiment, a BIC of the invention comprises a 2'-deoxyribonucleoside and three core nucleic acid moieties, where one of the nucleic acid moieties is linked to the 3'-hydroxyl position of the 2'-deoxyribonucleoside, one of the core nucleic acid moieties is linked to the 5'-hydroxyl position of the 2'-deoxyribonucleoside, and one of the core nucleic acid moieties is linked to the 5'-C, 4'-C, or 3'-C position of the 2'-deoxyribonucleoside.

In another embodiment, a branch-point nucleoside of the BIC is a ribonucleoside and one of the core nucleic acid moieties or other branch-point nucleosides of the BIC that are linked to the ribonucleoside is linked to the 2'- or 3'-hydroxyl position, one is linked to the 5'-hydroxyl position, and one is linked to the 5'-C, 4'-C, or 3'-C position of the ribonucleoside.

Accordingly, a BIC of the present invention optionally comprises a ribonucleoside and three core nucleic acid moieties, where one of the core nucleic acid moieties is linked to the 2'- or 3'-hydroxyl position of the ribonucleoside, one of the core nucleic acid moieties is linked to the 5'-hydroxyl position of the ribonucleoside, and one of the core nucleic acid moieties is linked to the 5'-C, 4'-C, or 3'-C position of the ribonucleoside.

Methods of synthesizing branch-point nucleoside precursor with branch points at one of the 5'-C, 4'-C, or 3'-C positions in addition to branch-points at the 5'-C and 3'-C or the 5'-C and 2'-C are known in the art. For example, in Pfundheller et al., *Helvetica Chimica Acta*, 2000, 83: 128-151, methods of preparing 4'-C and 3'-C-(aminoalkyl) thymidines suitable for use as branch-point nucleosides in the BICs of the invention are described. Synthesis and use of 4'-C-(hydroxymethyl) thymidine (Thrane et al., *Tetrahedron*, 1995, 51:10389-P-72), 3'-C-(hydroxymethyl) thymidine (Jorgensen et al., 1994, *J. Am. Chem. Soc.*, 116: 2231-32 and Jorgensen et al., *Tetrahedron*, 51: 2155-2164), and 5'-C-(hydroxymethyl) thymidine (Fensholdt et al., 1996, *Acta Chem Scand.* 50:1157-63) has also been described.

As noted above, the base of the branch-point nucleoside may be a purine or a pyrimidine. Optionally, the base of the branch-point nucleoside is adenine (A), guanine (G), uracil (U), cytosine (C), thymine (T), or hypoxanthine (I). Alternatively, the base may modified A, C, G, T, U or I, or an A, C, G, T, U or I analog. The base of the branch-point nucleoside may also optionally be another modified purine or pyrimidine. For instance, 2,6-diaminopurine may be used as a base on the branch-point nucleoside.

In one embodiment, a branch-point nucleoside of the BIC is a 2'-deoxyribonucleoside and with respect to the core nucleic acid moieties or branch-point nucleosides of the BIC that are linked to the 2'-deoxyribonucleoside, one is linked to the 3'-hydroxyl position, one is linked to the 5'-hydroxyl position, and one is linked to a position on the base of the 2'-deoxyribonucleoside.

Accordingly, a BIC of the present invention may comprise a 2'-deoxyribonucleoside and three core nucleic acid moieties, where one of the nucleic acid moieties is linked to the 3'-hydroxyl position of the 2'-deoxyribonucleoside, one of the nucleic acid moieties is linked to the 5'-hydroxyl position of the 2'-deoxyribonucleoside, and one of the nucleic acid moieties is linked to a position on the base of the 2'-deoxyribonucleoside.

In still another embodiment, a branch-point nucleoside of the BIC is a ribonucleoside and one of the core nucleic acid moieties or other branch-point nucleosides of the BIC that are linked to the ribonucleoside is linked to the 2'- or 3'-hydroxyl position, one is linked to the 5'-hydroxyl position, and one is linked to a position on the base of the ribonucleoside.

Accordingly, a BIC of the present invention may optionally comprise a ribonucleoside and three core nucleic acid moieties, where one of the nucleic acid moieties is linked to the 2'- or 3'-hydroxyl position of the ribonucleoside, one of the nucleic acid moieties is linked to the 5'-hydroxyl position of the ribonucleoside, and one of the nucleic acid moieties is linked to a position on the base of the ribonucleoside.

The position on the branch-point nucleoside's base to which a core nucleic acid moiety or another branch-point nucleoside may be linked will vary depending upon the particular nucleoside used. One of ordinary skill in the art will be able to readily discern which positions on a particular branch-point nucleoside are suitable for the linking of moieties to the branch-point nucleoside. This determination is made based on the type of functionality available on the base of a branch-point nucleoside. For instance, one of ordinary skill in the art will readily discern that the amino functionality on the C-4 position of cytidine (N-4) is a reactive group suitable for further modification including linkage of non-nucleic acid spacer moieties.

If the base of the branch-point nucleoside is a purine, then suitable branch points on the base typically include N-2, N-6, C-8, N-1, and O-6. In one embodiment, the base of the branch-point nucleoside is guanine, or a derivative thereof, and the position on the base to which the core nucleic acid moiety or the second branch-point nucleoside is linked is selected from the group consisting of N-2, N-1, O-6, and C-8. In another embodiment, the base of the branch-point nucleoside is adenine, or a derivative thereof, and the position on the base to which the core nucleic acid moiety or second branch-point nucleoside is linked is selected from the group consisting of N-6 and C-8. If the branch-point nucleoside is inosine, on the other hand, then the position on the base to which the core nucleic acid moiety or second branch-point nucleoside is linked is optionally selected from the group consisting of O-6 and C-8. If the branch-point nucleoside is 2,6-diaminopurine, then the position on the base to which the core nucleic acid moiety or second branch-point nucleoside is covalently coupled may be N-2, N-6, or C-8.

If the base of the branch-point nucleoside is a pyrimidine, then suitable branch points on the base typically include N-3, N-4, O-4, C-5, C-6, and O-2. For instance, if the base of the branch-point nucleoside is uracil, thymine, or a derivative of either uracil or thymine, then the position on the base to which the core nucleic acid moiety or second branch-point nucleoside is linked is typically selected from the group consisting of N-3, O-4, O-2, C-5 and C-6. If the base of the branch-point nucleoside is cytosine, or a derivative thereof, then the position on the base to which the core nucleic acid moiety or second branch-point nucleoside is linked is typically selected from the group consisting of N-4, C-5, and C-6. In certain embodiments, the the branch-point nucleoside is other than an N-4-(6-hydroxyhexyl)-5-methyl-2'-deoxycytidine.

Methods of synthesizing and incorporating nucleoside monomers with branch-points on at least one position of the base are known to those of ordinary skill in the art. For example, Lyttle et al., *Bioconjugate Chem.*, 2002, 13, 1146-1154, describes the syntheses and incorporation into oligonucleotides of such phosphoramidites as $N^4$-(2-(ethylene glycol-2-levulinate)ethyl)-5-methyl-5'-(4,4'-dimethoxytrityl)-3'-O-(2-cyanoethyldiisopropylphosphoramidite)-2'-deoxycytidine and 5-(N-(6-O-levulinoyl-1-aminohexyl)-3(E)-acrylamido)-5'-(4,4'-dimethoxytrityl)-3'-(2-cyanoethyldiisopropylphosphoramidite)-2'-deoxyuridine. Urdea et al, U.S. Pat. No. 5,093,232, Urdea et al, U.S. Pat. No. 5,124,246, U.S. Pat. No. 5,703,218, U.S. Pat. No. 5,591,584, Urdea et al., U.S. Pat. No. 5,594,118, Urdea and Horn, U.S. Pat. No. 5,594,118; Horn and Urdea, *Nucleic Acids Res.*, 1989, 17:6959-6967, Horn et al, *Nucleic Acids Res.*, 1997, 25: 4835-4841, Horn et al., *Nucleic Acids Res.*, 1997, 25:4842-4849 and Chang et al., U.S. Pat. No. 5,580,731 describe the synthesis of N-4 modified pyrimidine nucleotides, and incorporation of the monomers, such as N-4-(6-hydroxyhexyl)-5-methyl-2'-deoxycytidine, into oligonucleotides, sometimes including branched oligonucleotides. The synthesis and use of C8-hydroxymethyl-dA and C6-hydroxymethyl-dU monomers as branching monomers is described in Czechtisky and Vasella, *Helvetica Chimica Acta*, 2001, 84:1000-1016.

4. Spacer Moieties (SMs)

As noted supra, NAM and bN moieties in a BIC may be covalently coupled to other NAM and bN moieties in a variety of ways. For example, in some embodiments, the linkage between a bN and an NAM is, or comprises, a phosphodiester, phosphothioate ester, phosphorodithioate ester, phosphoramidite, or alkylphosphonate linkage. A bN and NAM can also be covalently coupled to each other via any of a variety of connecting molecules referred to herein as "spacer moieties (SMs)" which link NAM and bN moieties (e.g., a bN to a NAM, and NAM to another NAM, or a bN to another bN). Examples of SMs include, without limitation, $C_2$-$C_{10}$ alkyl groups, oligo-ethylene glycol groups, combinations of such groups, and polymers of such groups (e.g., ester-linked polymers). In a BIC comprising more than one SMs, the SMs may be the same or different. SMs are described in additional detail hereinbelow.

SMs are generally of molecular weight about 50 to about 5000, sometimes from about 75 to about 500.

Exemplary SMs and SM components include $C_2$-$C_{10}$ alkyl spacers, typically $C_2$-$C_6$ alkyl groups such as propyl, butyl, and hexyl groups). Other exemplary SMs are, or comprise, oligo-ethylene glycol components, such as triethylene glycol, tetraethylene glycol (TEG), and hexaethylene glycol (HEG), or polyethylene glycols having up to about 10, about 20, about 40, or about 50 ethylene glycol units. A SM may comprise one or more sugars, e.g., 1'2'-dideoxyribose, 1'-deoxyribose, 1'-deoxarabinose and polymers thereof, linked via an ester (e.g., phosphodiester) or other linkage.

Other suitable SMs comprise substituted alkyl, substituted polyglycol, optionally substituted polyamine, optionally substituted polyalcohol, optionally substituted polyamide, optionally substituted polyether, optionally substituted polyimine, optionally substituted polyphosphodiester (such as poly(1-phospho-3-propanol), and the like. Optional substituents include alcohol, alkoxy (such as methoxy, ethoxy, and propoxy), straight or branched chain alkyl (such as C1-C10 alkyl), amine, aminoalkyl (such as amino $C_1$-$C_{10}$ alkyl), phosphoramidite, phosphate, thiophosphate, hydrazide, hydrazine, halogen, (such as F, Cl, Br, or I), amide, alkylamide (such as amide $C_1$-$C_{10}$ alkyl), carboxylic acid, carboxylic ester, carboxylic anhydride, carboxylic acid halide, ether, sulfonyl halide, imidate ester, isocyanate, isothiocyanate, haloformate, carbodiimide adduct, aldehydes, ketone, sulfhydryl, haloacetyl, alkyl halide, alkyl sulfonate, $NR_1R_2$ wherein $R_1R_2$ is —C(=O)CH=CHC(=O) (maleimide), thioether, cyano, sugar (such as mannose, galactose, and glucose), $\alpha,\beta$-unsaturated carbonyl, alkyl mercurial, $\alpha,\beta$-unsaturated sulfone.

Other suitable SMs may comprise polycyclic molecules, such as those containing phenyl or cyclohexyl rings. The SM may comprise a polyether such as polyphosphopropanediol, polyethylene glycol, polypropylene glycol, a bifunctional polycyclic molecule such as a bifunctional pentalene, indene, naphthalene, azulene, heptalene, biphenylene, asymindacene, sym-indacene, acenaphthylene, fluorene, phenalene, phenanthrene, anthracene, fluoranthene, acephenathrylene, aceanthrylene, triphenylene, pyrene, chrysene, naphthacene, thianthrene, isobenzofuran, chromene, xanthene, phenoxathiin, which may be substituted or modified, or a combination of the polyethers and the polycyclic molecules. The polycyclic molecule may be substituted or polysubstituted with $C_1$-$C_5$ alkyl, $C_6$ alkyl, alkenyl, hydroxyalkyl, halogen or haloalkyl group. Nitrogen-containing polyheterocyclic molecules (e.g., indolizine) are typically not suitable spacers. The spacer may also be a polyalcohol, such as glycerol or pentaerythritol. SMs may comprise (1-phosphopropane)$_3$-phosphate or (1-phosphopropane)$_4$-phosphate (also called tetraphosphopropanediol and pentaphosphopropanediol) or derivatized 2,2'-ethylenedioxydiethylamine (EDDA).

Other suitable SMs include "linkers" described by Cload and Schepartz, 1991, *J. Am. Chem. Soc.* 113:6324; Richardson and Schepartz, 1991, *J. Am. Chem. Soc.* 113:5109; Ma et al., 1993, *Nucleic Acids Research* 21:2585; Ma et al., 1993, *Biochemistry* 32:1751; McCurdy et al., 1991, *Nucleosides & Nucleotides* 10:287; Jaschke et al., 1993, *Tetrahedron Lett.* 34:301; Ono et al., 1991, *Biochemistry* 30:9914; Arnold et al., International Publication No. WO 89/02439 and EP0313219B1 entitled "Non-nucleic acid Linking Reagents for Nucleotide Probes," Salunkhe et al., 1992, *J. Am. Chem. Soc.* 114:8768; Nelson et al., 1996, *Biochemistry* 35:5339-44; Bartley et al., 1997, *Biochemistry* 36:14502-511; Dagneaux et al. 1996, *Nucleic Acids Research* 24:4506-12; Durand et al., 1990, *Nucleic Acids Research* 18:6353-59; Reynolds et al., 1996, *Nucleic Acids Research*, 24:760-65; Hendry et al. 1994, *Biochemica et Biophysica Acta*, 1219:405-12; Altmann et al., 1995, *Nucleic Acids Research* 23:4827-35, and U.S. Pat. No. 6,117,657 (Usman et al.).

A variety of SMss are described herein, for illustration and not limitation. It will be appreciated by the reader that, for convenience, a SM or SM component is sometimes referred to by the chemical name of the compound (e.g., hexaethylene glycol) from which the spacer moiety or component is derived, with the understanding that the BIC actually comprises the conjugate of the compound(s) to a branch-point nucleoside and nucleic acid moiety (or between two two branch-point nucleosides, or between two nucleic acid moieties). Usually, as is illustrated for HEG in Examples 1-4 and 6-8, infra, a SM can be formed from a spacer moiety precursor(s) that include reactive groups to permit coupling of a the spacer moiety precursor a branch-point nucleoside, a nucleic acid moiety, or other spacer moiety componant, and protecting groups may be included. The reactive groups on the spacer precursor may be the same or different.

It will be clear to the reader that mononucleotides and polynucleotides cannot be SMs (without which exclusion there would be no difference between a NAM and an adjacent SM).

Suitable SMs do not render the BIC of which they are a component insoluble in an aqueous solution (e.g., PBS, pH 7.0). Thus, SMs do not include microcarriers or nanocarriers. In addition, a spacer moiety that has low solubility, such as a dodecyl spacer (solubility <5 mg/ml when measured as dialcohol precursor 1,12-dihydroxydodecane) is not preferred because it can reduce the hydrophilicity and activity of the BIC. Preferably, spacer moieties have solubility much greater than 5 mg/ml (e.g., solubility at least about 20 mg/ml, at least about 50 mg/ml or at least about 100 mg/ml), e.g., when measured as dialcohol precursors. The form of the spacer moiety used for testing its water solubility is generally its most closely related unactivated and unprotected spacer precursor molecule.

A spacer moiety can comprise smaller units (SM components) and can be a homopolymer or heteropolymer of SM components. For example, the SM of BIC B07 [(5'-TC-GACGT-3'-HEG)$_2$-(U)-AHA-HEG-5'-TCGACGT-3'] can be described as having two HEG SMs and one SM comprising a HEG componant in a phosphorothioate linkage to a 6-hydroxy-1-aminohexyl-3(E)-acrylamido componant.

In one embodiment, a SM comprises multiple covalently connected components (or subunits) and may have a homopolymeric or heteropolymeric structure. In some SMs the componants are connected by a linker, phosphodiester linkage, and/or phosphorothioate ester linkage. In one embodiment, for illustration and not limitation, the BIC comprises a SM comprising any two or more (e.g., 3 or more, 4 or more, or 5 or more) subunits selected from the following types, in phosphodiester linkage and/or phosphorothioate ester linkage: oligoethylene glycol SM componant (e.g., triethylene glycol componant; hexaethylene glycol componant); alkyl SM componant (e.g., propyl componant; butyl componant; hexyl componant); branched SM componant (e.g., 2-(hydroxymethyl)ethyl spacer; glycerol spacer; trebler spacer; symmetrical doubler spacer). As an example, a spacer moiety may comprise glycerol conjugated via a phosphodiester linkage to an oligoethylene glycol such as HEG (e.g., X=[5'T•C•G•T•C•G•A$^3$'•HEG]$_2$•glycerol•HEG•[bN]• (nucleic acid moiety)$_2$, where "●" indicates a phosphodiester linkage). Other common linkages between SM componants include phosphorothioate, amide, ether, thioether, disulfide, phosphoramidate, phosphotriester, phosphorodithioate, and methyl phosphonate.

Figure 7:
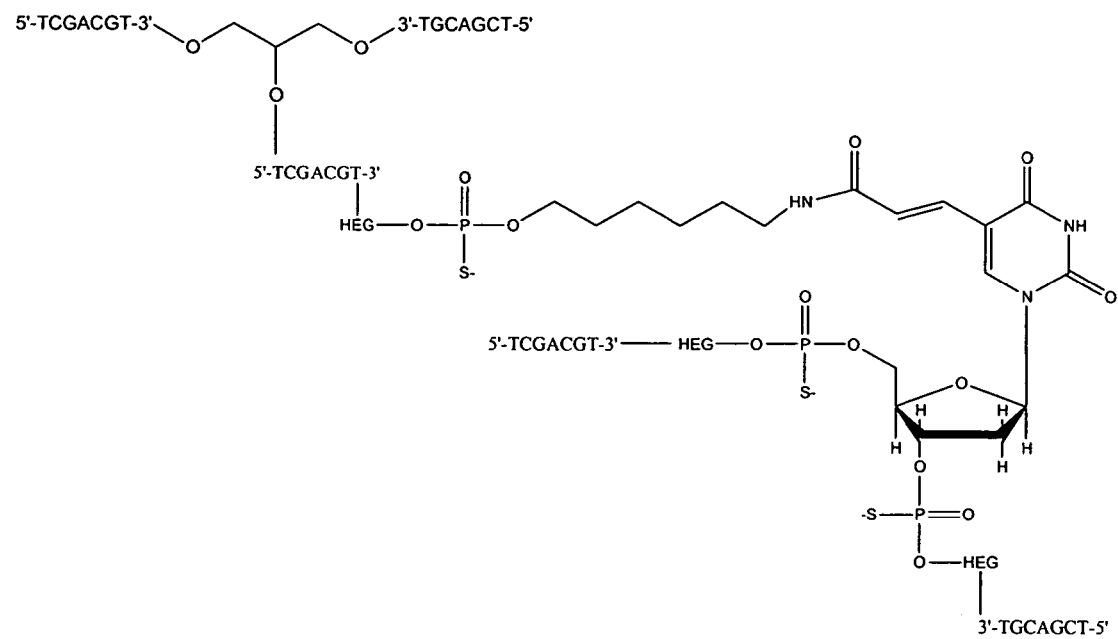
FIG. 7 shows a BIC comprising a multivalent (branched) SM and having the formula (5-TCGACGT-3'-HEG)-(5'-U-3')-HEG-(3'-TGCAGCT-5') b-AHA(HEG-3'-TGCAGCT-5')-glycerol-(3'-TGCAGCT-5')$_2$, where b indicates the moieties attached to the C5 position of the 2'-deoxyuridine base of the branch-point nucleoside via the AHA spacer moiety.

Spacer moieties may also be multivalent (e.g., branched). Examples of suitable multivalent SMs include glycerol or substituted glycerol (e.g., 2-hydroxymethyl glycerol, levulinyl-glycerol); tetraaminobenzene, heptaaminobetacyclodextrin, 1,3,5-trihydroxycyclohexane, pentaerythritol and derivatives of pentaerythritol, tetraaminopentaerythritol, 1,4, 8,11-tetraazacyclo tetradecane (Cyclam), 1,4,7,10-tetraazacyclododecane (Cyclen), polyethyleneimine, 1,3-diamino-2-propanol and substituted derivatives (e.g., "symetrical doubler"), [propyloxymethyl]ethyl compounds (e.g., "trebler"), polyethylene glycol derivatives such as so-called "Star PEGs" and "bPEG" (see, e.g., Gnanou et al., 1988, Makromol. Chem. 189:2885; Rein et al., 1993, Acta Polymer 44:225, Merrill et al., U.S. Pat. No. 5,171,264; Shearwater Polymers Inc., Huntsville Ala.). A multivalent SM can be bound to multiple NAs or other moieties. See FIG. 7.

5. Synthesis of BICs

A. NAMs, SMs and bNs

It will be within the ability of one of skill, guided by this specification and knowledge in the art, to prepare BICs using routine methods. The componants of BICs (e.g., NAMs, bNs, and SMs) can be prepared and combined using a variety of methods. The methods described herein are exemplary and not intended to be limiting.

Techniques for making nucleic acid moieties (e.g., oligonucleotides and modified oligonucleotides) are known. Nucleic acid moieties can be synthesized using techniques including, but not limited to, enzymatic methods and chemical methods and combinations of enzymatic and chemical approaches. For example, DNA or RNA containing phosphodiester linkages can be chemically synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Useful solid supports for DNA synthesis include Controlled Pore Glass (Applied Biosystems, Foster City, Calif.), polystyrene bead matrix (Primer Support, Amersham Pharmacia, Piscataway, N.J.) and TentGel (Rapp Polymere GmbH, Tubingen, Germany). Once the desired oligonucleotide sequence has been synthesized, the oligonucleotide is removed from the support, the phosphate triester groups are deprotected to phosphate diesters and the nucleoside bases are deprotected using aqueous ammonia or other bases.

For instance, DNA or RNA polynucleotides (nucleic acid moieties) containing phosphodiester linkages are generally synthesized by repetitive iterations of the following steps: a) removal of the protecting group from the 5'-hydroxyl group of the 3'-solid support-bound nucleoside or nucleic acid, b) coupling of the activated nucleoside phosphoramidite to the 5'-hydroxyl group, c) oxidation of the phosphite triester to the phosphate triester, and d) capping of unreacted 5'-hydroxyl groups. DNA or RNA containing phosphorothioate linkages is prepared as described above, except that the oxidation step is replaced with a sulfurization step. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in PROTOCOLS FOR OLIGONUCLEOTIDES AND ANALOGS, SYNTHESIS AND PROPERTIES (Agrawal, ed.) Humana Press, Totowa, N.J.; Warner et al. (1984) DNA 3:401; Tang et al. (2000) Org. Process Res. Dev. 4:194-198; Wyrzykiewica et al. (1994) Bioorg. & Med. Chem. Lett. 4:1519-1522; Radhakrishna et al. (1989) J. Org. Chem. 55:4693-4699. and U.S. Pat. No. 4,458,066. Programmable machines that automatically synthesize nucleic acid moieties of specified sequences are widely available. Examples include the Expedite 8909 automated DNA synthesizer (Perseptive Biosystem, Framington Mass.); the ABI 394 (Applied Biosystems, Inc., Foster City, Calif.); and the OligoPilot II (Amersham Pharmacia Biotech, Piscataway, N.J.).

Polynucleotides can be assembled in the 3' to 5' direction, e.g., using base-protected nucleosides (monomers) containing an acid-labile 5'-protecting group and a 3'-phosphoramidite. Examples of such monomers include 5'-O-(4,4'-dimethoxytrityl)-protected nucleoside-3'-O-(N,N-diisopropylamino) 2-cyanoethyl phosphoramidite, where examples of the protected nucleosides include, but are not limited to, N6-benzoyladenosine, N4-benzoylcytidine, N2-isobutryrylguanosine, thymidine, and uridine. In this case, the solid support used contains a 3'-linked protected nucleoside. Alternatively, polynucleotides can be assembled in the 5' to 3' direction using base-protected nucleosides containing an acid-labile 3'-protecting group and a 5'-phosphoramidite. Examples of such monomers include 3'-O-(4,4'-dimethoxytrityl)-protected nucleoside-5'-O—(N,N-diisopropylamino) 2-cyanoethyl phosphoramidite, where examples of the protected nucleosides include, but are not limited to, N6-benzoyladenosine, N4-benzoylcytidine, N2-isobutryrylguanosine, thymidine, and uridine (Glen Research, Sterling, Va.). In this case, the solid support used contains a 5'-linked protected nucleoside. Circular nucleic acid components can be isolated, synthesized through recombinant methods, or chemically synthesized. Chemical synthesis can be performed using any method described in the literature. See, for instance, Gao et al. (1995) Nucleic Acids Res. 23:2025-2029 and Wang et al. (1994) Nucleic Acids Res. 22:2326-2333.

Although use of phosphoramidite chemistry is convenient for the preparation of certain BICs, it will be appreciated that the BICs of the invention are not limited to compounds prepared by any particular method of synthesis or preparation. For example, nucleic acid moieties containing groups not compatible with DNA synthesis and deprotection conditions, such as (but not limited to) hydrazine or maleimide, can be prepared by reacting a nucleic acid moiety containing an amino linker with the appropriate heterobifunctional crosslinking reagent, such as SHNH (succinimidyl hydraziniumnicotinate) or sulfo-SMCC (sulfosuccinimidyl 4-[N-maleimidomethyl]-cyclohexame-1-carboxylate).

Synthesis of branch-point nucleosides is known in the art. For instance, the synthesis of bNs with functionality appropriate for use in conjunction with phosphoroamidite-based DNA synthesis are described in, for example, Chang et al. U.S. Pat. No. 5,580,731, Lyttle et al. (2002) Bioconjugate-Chem. 13:1146-1154, von Büren et al. (1995) Tetrahedron 51:8491-8506, D;amha et al (1992) Nucleic Acids Res. 20:6565-6573, Kierzek et al (1986) Nucleic Acids Res. 14:4751-4763, and Pfundheller et al (2000) Helvetica Chimica Acta 83:128-151. Branch-point nucleosides may be prepared with reactive groups that allow for a variety of types of covalent linkage between the branch-point nucleoside and a NAM or SM, including but not limited to phosphodiester, phosphorothioate, phosphorodithioate, phosphoramidate, methyl phosphonate, phosphotriester, amide, ester, ether, thioether; and disulfide.

A variety of branch-point nucleosides with useful protecting and reacting groups are commercially available, for example:

U-AHA branch-point nucleoside: (5-(N-(6-O-levulinoyl-1-aminohexyl)-3(E)-acrylamido-5'-O-(4,4'-dimethoxytrityl)-3'-O-(N,N-diisopropyl) (2-cyanoethylphosphoramidite)-2'-deoxyuridine (FIG. 1A, Biosearch Technologies, Novato, Calif.)

mdC-DEG branch-point nucleoside: (N4-(6-O-levulinoyl-1-diethylene glycol)-5-methyl-5'-O-(4,4'-dimethoxytrityl)-3'-O-(N,N-diisopropyl) (2-cyanoethylphosphoramidite)-2'-deoxycytidine (FIG. 1E, Biosearch Technologies, Novato, Calif.)

U-MDP branch-point nucleoside: (5-(N-(1-O-fluorenylmethoxycarbonamidyl-methyl)-1,2-disuccinamidyl)-3-propynyl-5'-O-(4,4'-dimethoxytrityl)-3'-O-(N,N-diisopropyl) (2-cyanoethylphosphoramidite)-2'-deoxyuridine (FIG. 1C, Eurogentec, eurogentec.com)

rA branch-point nucleoside: (5'-O-(4,4'-dimethoxytrityl)-3'-O-(N,N-diisopropyl) (2-cyanoethylphosphoramidite)-2'-t-butyldimethylsilyl-adenosine (Glen Research, Sterling, Va.).

Synthesis of spacer moieties is also known in the art. For instance, spacer moieties with functionality appropriate for use in conjunction with phosphoramidite-based DNA synthesis are synthesized from a diol (e.g., hexaethylene glycol, 1,3-propanediol, and the like) by monoprotecting one alcohol using 4,4'-dimethoyxtrityl chloride and monoactivating the other alcohol with 2-cyanoethyl diisopropylchlorophosphoramidite. Spacer moieties may be prepared with reactive groups that allow for a variety of types of covalent linkage between the branch-point nucleoside and the NAM, including but not limited to phosphodiester, phosphorothioate, phosphorodithioate, phosphoramidate, methyl phosphonate, phosphotriester, amide, ester, ether, thioether, and disulfide.

Many spacer moieties with useful protecting and reactive groups are commercially available, including but not limited to:

triethylene glycol spacer or "TEG spacer" 9-O-(4,4'-dimethoxytrityl)triethyleneglycol-1-O-[(2-cyanoethyl) N,N-diisopropylphosphoramidite] (Glen Research, Sterling, Va.);

hexaethylene glycol spacer or "HEG spacer" 18-O-(4,4'-dimethoxytrityl)hexaethyleneglycol-1-O-[(2-cyanoethyl) N,N-diisopropylphosphoramidite] (Glen Research, Sterling, Va.);

propyl spacer 3-(4,4'-dimethoxytrityloxy)propyloxy-1-O-[(2-cyanoethyl) N,N-diisopropylphosphoramidite] (Glen Research, Sterling, Va.);

butyl spacer 4-(4,4'-dimethoxytrityloxy)butyloxy-1-O-[(2-cyanoethyl) N,N-diisopropylphosphoramidite] (Chem Genes Corporation, Ashland Technology Center, Ashland, Mass.);

Hexyl spacer: 6-(4,4'-dimethoxytrityloxy)hexyloxy-1-O-[(2-cyanoethyl) N,N-diisopropylphosphoramidite] (Biosearch Technologies, Novoto, Calif.)

2-(hydroxymethyl)ethyl spacer or "HME spacer" 1-(4,4'-dimethoxytrityloxy)-3-(levulinyloxy)-propyloxy-2-O-[(2-cyanoethyl) N,N-diisopropylphosphoramidite (Chem Genes Corp., Ashland Technoklgy Center, Ashland Mass.)

"abasic nucleotide spacer" or "abasic spacer" 5-O-(4,4'-dimethoxytrityl)-1,2-dideoxyribose-3-O-[(2-cyanoethyl) N,N-diisopropylphosphoramidite] (Glen Research, Sterling, Va.);

"symmetrical branched spacer" or "glycerol spacer" 1,3-O, O-bis(4,4'-dimethoxytrityl)glycerol-2-O-[(2-cyanoethyl) N,N-diisopropylphosphoramidite] (Chem Genes, Ashland, Mass.) (see FIG. 2);

"trebler spacer" (see FIG. 2) 2,2,2-O,O,O-tris[3-O-(4,4'-dimethoxytrityloxy)propyloxymethyl]ethyl-1-O-[(2-cyanoethyl) N,N-diisopropylphosphoramidite] (Glen Research, Sterling, Va.);

"symmetrical doubler spacer" (see FIG. 2) 1,3-O,O-bis[5-O-(4,4'-dimethoxytrityloxy)pentylamido]propyl-2-O-[(2-cyanoethyl) N,N-diisopropylphosphoramidite] (Glen Research, Sterling, Va.).

B. Synthesis of BICs

The synthesis of branched oligonucleotides is known in the art and analogous methods may be used in the synthesis of BICs. For instance, the synthesis of branched oligonucleotides containing a ribonucleotide as the branch-point nucleoside is described in Braich and Damha (1997) Bioconjugate Chem. 8:370-377, Hudson, H. E. and Damha, M. J. (1993) J. Am. Chem. Soc. 115:2119-2124, Damha, M. J. and Zabarylo, S. V. (1989) Tetrahedron Lett. 30:6295-6298 Damha, M. J.; Ganeshan, K.; Hudson, R. H. E.; Zabarylo, S. V. (1992) Nucleic Acids Res. 20:6565-6573, Kierzek, R.; Kopp, D. W.; Edmonds, M.; Caruthers, M. H. (1986) Nucleic Acids Res. 14:4751-4764, Sproat, B. S.; Beijer, B.; Grøtli, M.; Ryder, U.; Morand, K. L.; Lamond, A. I. (1994) J. Chem. Soc. Perkin Trans. I 4:419-431, Polushin, N. N. (1999) Collection Symposium Series 2:145-150, Von Büren, M.; Petersen G. V.; Rasmussen, K.; Brandenburg, G.; Wengel, J. (1995) Tetrahedron 51:8491-8506. Further examples of the synthesis of branched oligonucleotides containing a branch-point attached to the base of the branch-point nucleoside include Chang, C.; Urdea, M. S.; Horn, T. 1996 U.S. Pat. No. 5580731, Horn, T. and Urdea M. S. (1989) Nucleic Acids Res. 17:6959-6967, Horn T.; Chang, C-A.; Urdea M. S. (1997) Nucleic Acids Res. 25:4835-4841, Horn T.; Chang, C-A.; Urdea M. S. (1997) Nucleic Acids Res. 25:4842-4849, and Czechtizky, W.; Vasella, A. (2001) Helv. Chim. Acta 84:1000-1016. Branched oligonucleotides containing 5'-C, 4'-C, or 3'-C branching sites can be synthesized as described in Thrane, H.; Fensholdt, J.; Regner, M.; Wengel, J. (1995) Tetrahedron 51:10389-P-72, Jørgensen, P. N.; Stein, P. C.; Wengel, J. (1994) J. Am Chem. Soc. 116:2231 and Jørgensen, P. N.; Svendsen, M. L.; Scheuer-Larsen, C.; Wengel, J. (1995) Tetrahedron 51:2155.

In one approach, BICs are prepared using branched nucleosides and spacer moieties containing the same reactive and protecting groups as those used in DNA synthesis, for instance a 2-cyanoethyl (N,N-diisopropyl)phosphoramidite reactive group and a 4,4'-dimethoxytrityl protecting group. These types of branch-point nucleosides and spacer moieties are covalently linked to each other and to the NAMs through phosphodiester or phosphorothioate linkages using the same synthesis cycle previously described for the NAM synthesis. The branched nucleoside often has another protecting group that has orthogonal protection compared to the 4,4'-dimethoxytrityl group, such as levulinyl. This group can be selectively removed either before or after the detritylation step in the synthesis cycle. Often due to steric hinderance, increased concentrations of reactive groups and increased reaction times are necessary to maintain high coupling yields to the branched nucleoside. BICs prepared in this manner are deprotected and purified as described for oligonucleotides.

6. Purification

The BICs of the invention are purified using any conventional means, such as high performance liquid chromatography (see Examples), electrophoretic methods, nucleic acid affinity chromatography, size exclusion chromatography, and ion exchange chromatography. In some embodiments, a BIC is substantially pure, e.g., at least about 80% pure by weight, often at least about 90% pure by weight, more often at least about 95% pure, most often at least about 98% pure.

7. Exemplary BIC Structures and Tertiary Confirmation

A. Exemplary BIC Structures

As is noted above, a BIC of the invention may comprise multiple branch-point nucleosides. For instance, a BIC may have at least two, at least three, at least four, at least five, or at least ten branch-point nucleosides within its structure.

In one embodiment, a BIC comprises a single bN and three prime NAMs. Such a BIC can be referred to as having a "Y" structure.

In one embodiment, a BIC comprises a structure of $(bN)_{n+2}(NA)_{n+4}$ wherein n is an integer from n is an integer from 0 to about 25, sometimes 0 to 10, 0 to 5, 0 to 3, or falls into the range defined by a lower limit of 0, 1, 2, 3, 4, 5, 6, 7, or 8 and an independenly selected upper limit of 1, 2, 3, 4, 5, 6, 7, 8, 10, 15, or 25, where the upper limit is greater than the lower limit. For example (and for illustration only) a BIC may comprise the following structure:

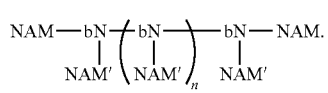

Structure IV where n=0-25, often 0-10, or 3-10; and where NAM and NAM' are independently selected nucleic acid moieties. In various embodiments, all NAM' have a common property, e.g., all have the same sequence and/or all are prime NAMs, all are 5-prime NAMs or all are 3-prime NAMs.

In a related aspect, a BIC comprises at least two branch-point nucleosides and at least four core NAMs. In embodiments, a BIC comprises a branch-point nucleoside covalently coupled to one, two or three other branch-point nucleosides.

Although a BIC may be characterized by structures such as Structures I and II, supra, it will be apparent that an individual BIC may comprise more than one such "core structure." As is discussed supra, BICs of the invention, so long as they comprise one or more of the core structures described herein may, and often do, include additional covalently coupled NAMs and bNs, as well as other covalently bound groups and atoms. For example, in one embodiment, a BIC comprises at least one bN covalently coupled to four (or more) NAMs, where each NAM is linked to a different position of the bN. Further, a bN may be covalently coupled to more than one NAM at a single position, if, for example, a SM (e.g., a glycerol based SM) introduces a branch point). See, for example, the BIC of FIG. 7, in which two NAMs are covalently coupled to the C5 position of the uridine base, and two additional NAMs are covalently coupled to the 5' and 3' positions[6] of the pentose sugar of the nucleoside. It is possible, by use of branching SMs, to design a BIC with from 1 to 10, or from 1 to 25 (or even more than 25) core NAMs.

In another embodiment, the BIC may optionally comprise at least one peripheral NAM, e.g., from 0 to about 25, from 0 to 3, or from 0 to 10 peripheral NAMs.

In an embodiment, the BIC may comprise more than 3 core NAMs, e.g., from 4 to 6, from 4 to 10, from 4 to 25, from 10 to 25, or more than 25 core NAMs.

In an embodiment, all of the core NAMs is a prime NAM (e.g. 5 prime NAM). In an embodiment, all of the prime NAMs (e.g., 5 prime NAMs) is a peripheral NAM.

B. BICs with Defined Tertiary Structure

It will be apparent from the discussion hereinabove that BICs can be characterized based on structural features. This section and the following section (§ 8) describe additional BIC secondary and tertiary structures and BIC multimers.

BICs and BIC multimers described in this section may be targeted to, or efficiently taken up by phagocytic cells or antigen-presenting cells, may present a high density of nucleic acid moiety 5'-ends, may change structure in vivo (e.g., due to nuclease or other degradative activity, acidification in the endosome, and/or dilution of the BIC or multimer in vivo (thereby changing properties after administration to a subject or in a particular biological compartment).

As noted elsewhere herein, BICs may comprise two nucleic acid moieties with sequences entirely or partially complementary to each other. The complementary sequence-NAMs can hybridize to each other to from intra-BIC duplexes. See, e.g., Example 5 (C-621). As is discussed below in § 8, complementary NAMs from different BICs can also form duplexes in the formation of BIC multimers.

In a duplex, the pair of NAMs with complementary sequences can be self-complementary (e.g., palindromic) or the pair can have different sequences. It will be appreciated that exact complementarity is not required so long as the nucleic acid moieties are of sufficient complementarity and length to form a duplex at 37° C. in an aqueous solution at physiological pH (i.e., 7.0-7.4, e.g., 7.2) and ionic strength (e.g., 150 mM NaCl). Formation of intra-BIC duplexes requires that the two NAMs in the duplex can be reach a conformation in which base-pairing can occur. Usually the presence of an intervening NAMs, SMs and/or bN provides sufficient freedom-of-orientation to allow such a BIC to achieve such a conformation.

The presence of a duplex structure can be detected using well-known methods. These include detecting a change in BIC structure based on size exclusion chromatography, and detecting a change in $A_{260}$ or $A_{280}$ upon raising or lowering the temperature of the BIC-containing composition (indicative of melting or formation of the duplex). Absorbance increases as a double-stranded DNA separates into the single-stranded forms.

In addition to the formation of intramolecular duplexes, BICs of other conformations can be designed. Exemplary conformations include the "H" and "comb" structures.

An "H" structure is defined by having
exactly two bNs;
four prime NAMs, which may be core NAMs or peripheral NAMs;
zero or at least one internal NAMs (usually fewer than 20, sometimes fewer than 10, sometimes 5).

Figure 3:
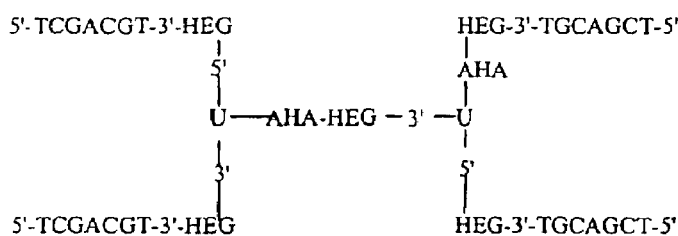
FIG. 3 shows a BIC with an "H" structure.
Figure 4:
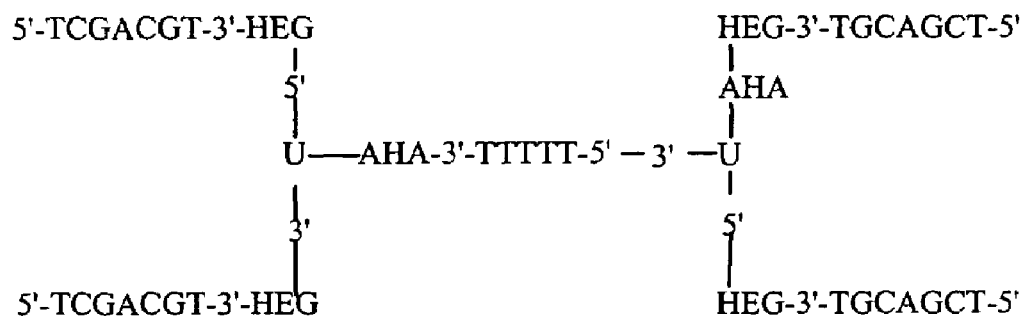
FIG. 4 shows a BIC with an "H" structure.

See FIGS. 3 and 4. In an embodiment, at least 3, or at least 4 of the prime NAMs are 5' NAMs. In one embodiment, the 5-prime NAMs are the same (i.e., have the same sequence and length). In an embodiment, at least 1, at least 2, at least 3, or all 4 of the 5-prime NAMs nucleic acid moieties include the sequence CG, optionally TCG, optionally $5'^F$-TCG.

A BIC may comprise a structure with the conformation of a "comb" structure. A "comb" structure comprises the following structure V:

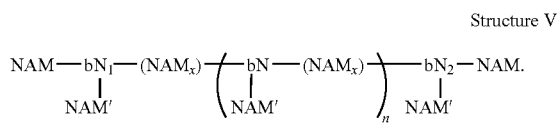

Structure V wherein n can be from 1 to 10, preferably 3 to 6, most preferably 3 or 4, x can be 0-3, usually 0 or 1, "-" indicates that a NAM and bN are covalently coupled (e.g., optionally through an SM), and each NAM and SM is independently selected and may be the same or different. In various embodiments, at least one nucleic acid moiety is a prime moiety, a 5-prime moiety and/or includes the sequence CG, optionally TCG, optionally $5^{tF}$-TCG. In an embodiment, each NAM' is a 5-prime moiety, and/or includes the sequence CG, optionally TCG, optionally $5^{tF}$-TCG. In one embodiment all of the prime moieties (e.g., 5-prime moieties) have the same sequence and/or all of the nucleic acid moieties that are not 5' moieties have the same sequence and/or all the internal moieties have the same sequence. See FIGS. 5 and 6.

Figure 8:
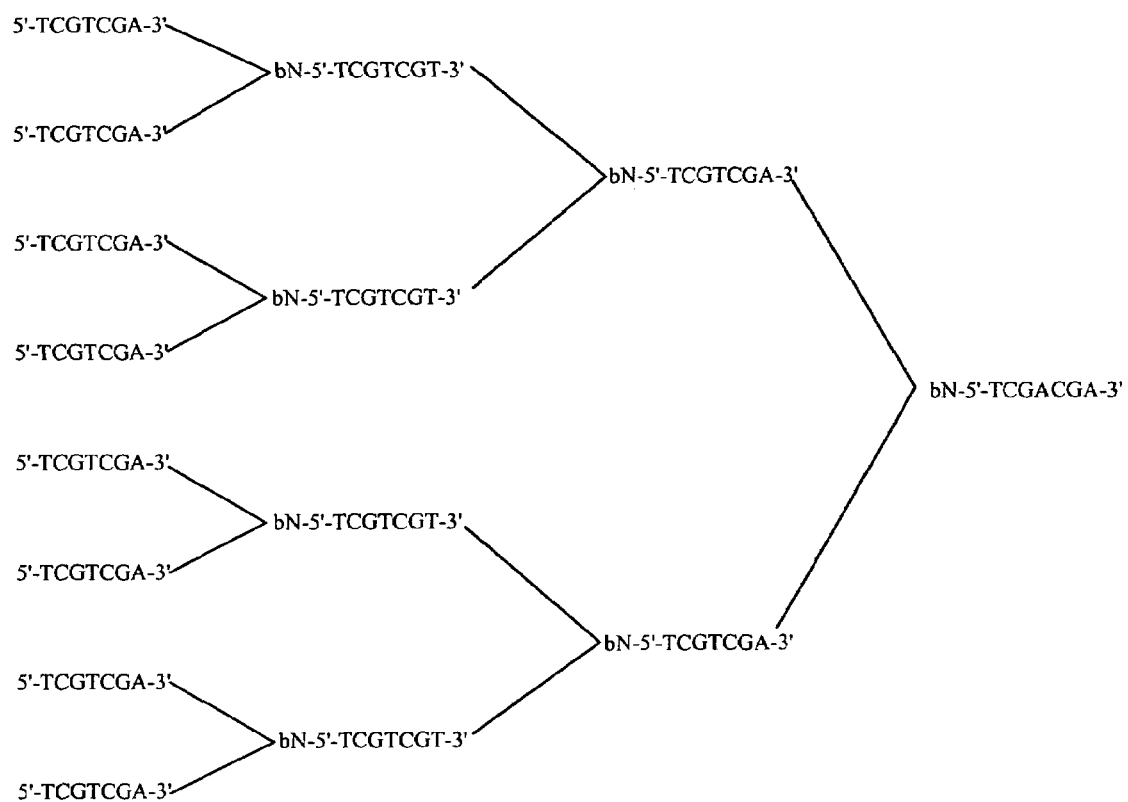
FIG. 8 shows a BIC dendrimer. In the BICs illustrated in FIGS. 8-9, the linkages between the nucleotides in the NAMs and between NAMs and the branch-point nucleoside may be phosphorothioate. The lines indicate covalent coupling of the branch-point nucleosides and NAMs (e.g., via phosphorothioate linkages and/or a spacer moiety (s)).

In one aspect, the BIC can have the structure of a dendrimer ("BIC dendrimer"). A BIC dendrimer is a discrete, highly branched polymer created by covalent linking of multiple (e.g., 3-15) copies of a branched BIC. For example, FIG. 8 shows a third generation BIC dendrimer produced by linking BICs having core structure II.

8. BIC Multimers

Certain BICs of the invention can form "multimers" of 2 or more BICs that stably associate with each other due to Watson-Crick hybridization between pairs of at least partially complementary nucleic acid moieties. BICs can be designed to assemble into a desired multimer. A number of multimeric conformations are possible, of which two examples are discussed below: a "central axis BIC multimer" and a "cage structure" BIC multimer.

As noted, individual BICs in BIC multimers stably associate with each other. As used in this context, "stably associate" means the BICs remain associated at 37° C. in a buffered aqueous salt solution of near physiological ionic strength and pH, e.g., 150 mM NaCl, pH 7.2. It will be recognized, of course, that even "stably associated" multimeric macromolecules may exist in a state of equilibrium such that an individual BICs may be unassociated with the multimer for relatively brief periods of time, or there may be exchange between BICs in the multimeric structure and unassociated monomers in solution. BIC multimers may be self assembling (i.e., the component BICs may spontaneously associate under physiological conditions). Usually, a BIC multimer will form when the component BICs are dissolved at a concentration of approximately 1.0 mg/ml in 50 mM sodium phosphate/150 mM sodium chloride/pH 7.2, heated to 95° C. for 3 min., and allowed to slowly (e.g., over a period of approximately 2 hours) to 37° C. or room temperature. See Example 7, infra.

Figure 9:
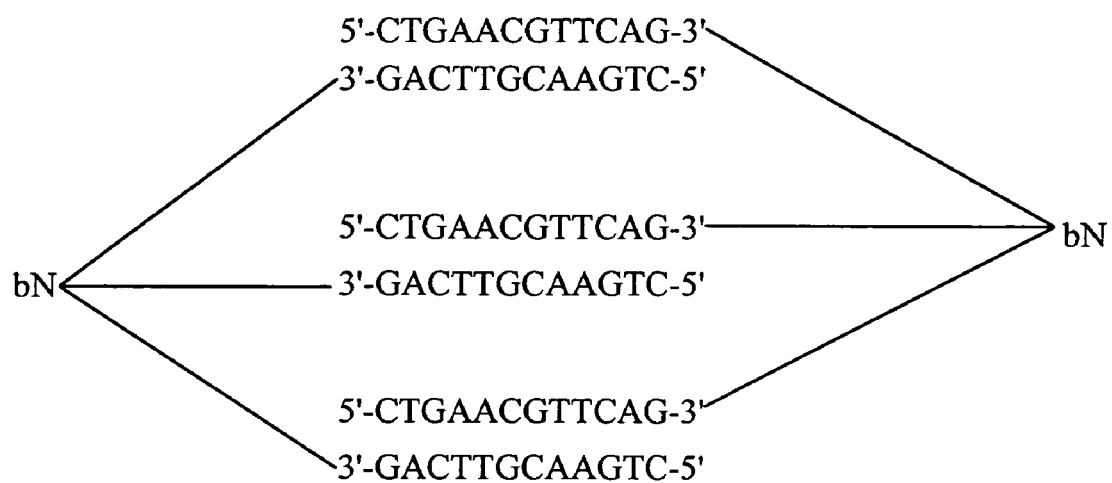
FIG. 9 shows a BIC multimer with a "cage" structure (SEQ ID NO: 2). The linkages between the nucleotides in the NAMs and between NAMs and the branch-point nucleoside may be phosphorothioate. The lines indicate covalent coupling of the branch-point nucleosides and NAMs (e.g., via phosphorothioate linkages and/or a spacer moiety (s)).

Because the association between BICs in a BIC multimer relies, at least in part, on hybrids formed between nucleic acid moieties that are at least partially complementary, and sometimes exactly complementary, the normal parameters for formation of nucleic acid hybrids apply. That is, the hybridizing regions of nucleic acid moieties are of sufficient length and/or sequence composition (e.g., GC content) to form stable BIC multimers. Generally the nucleic acid moieties of one BIC will comprise at least 8, more often at least 10, and usually at least 12 contiguous bases that are exactly complementary to nucleic acid moieties of a second BIC in the multimer. However, where there are a large number of hybridizing nucleic acid moieties, the region of complementarity or contiguity may be shorter. Conditions under which two polynucleotides, or regions of a self-complementary polynucleotide, will form a duplex can be determined empirically or predicted using are well known methods (taking into consideration base sequence, polynucleotide length, ester linkage [e.g., phosphorothioate or phosphodiester linkage], temperature, ionic strength, presence of modified bases or sugars, etc.). The annealing nucleic acid moieties in the associating BICs may each be self-complementary (see, e.g., FIGS. 2 and 9) or alternatively a nucleic acid moiety(s) on one BIC may be complementary to a nucleic acid moiety(s) on a second BIC but not to itself.

Figure 2:
FIG. 2 shows a BIC with a "central axis" structure. In the BICs illustrated in FIGS. 2-6, the linkages between nucleotides in the NAMs, between nucleotides of the NAM and HEG, between HEG and the branch-point nucleoside, between HEG and the AHA component, and between NAMs and the branch-point nucleoside may be phosphorothioate (SEQ ID NO: 1).

An example of a BIC multimer (dimer) is shown in FIG. 2 and described in Example 7, infra. The structure shown in FIG. 2 is an example of a "central axis" structure. A central axis multimer comprises two or more BICs of Structure II (see supra) that are stably associated by hybridization of one of more NAMs in each BIC. In one embodiment, the central axis structure is a dimer in which one NAM of each BIC is duplexed and both duplexed NAMs are core NAMs. Alternatively, a central axis can comprise multiple duplexed NAMs from each BIC, and the NAMs can be core NAMs, peripheral NAMs, or comprise both. In a related embodiment, a central axis multimer can comprise more than two BICs. It will be understood that, for any BIC of the multimer, no two other BICs will form duplexes with NAMs of the first BIC that are covalently coupled to the same position of the bN of the first BIC; each other BIC will form duplexes with NAMs of the first BIC that are covalently coupled to a different position of the bN.

Another example of a structure of a BIC multimer is a "cage" structure. See, e.g., the BIC shown in FIG. 9. In a cage structure, each BIC comprises at least 2, and usually at least 3, prime NAMs (e.g., 5-prime NAMs) that hybridize to at least 2, and usually at least 3, prime NAMs of a second BIC. Typically, as in the example shown in FIG. 9, the two BICs are the same. Sometimes, as in the example shown in FIG. 9, all of the annealing NAMs are core NAMs. A "cage" structure is characterized in that each of the annealing NAMs is annealed to a NAM with the same polarity (e.g., both have free 5' ends or both have free 3' ends).

A "starfish" structure is another type of multimeric BIC. A starfish structure has the same properties as the cage structure, supra, except each of the annealing NAMs is annealed to a NAM with the opposite polarity (e.g., one has a free 5' end and the other a free 3' end).

In each type of BIC multimer, it will be understood that nucleic acid moieties in the multimer may have any of the sequence, structural features or properties described herein for nucleic acid moieties, so long as the feature is consistent with the multimer structure. Thus, one or more nucleic acid moieties may be a 5-prime moiety, may include the sequence CG, TCG, or $5^{tF}$-TCG, or have other sequence, motif or property described herein. Further, it will be understood the multimers described in the figures and examples are provided for illustration and not limitation.

9. Immunomodulatory Activity of BICs

The BICs of the invention have immunomodulatory activity. The terms "immunomodulatory," "immunomodulatory activity," or "modulating an immune response," as used herein, include immunomodulatory as well as immunosuppressive effects. An immune response that is immunomodulated according to the present invention is generally one that is shifted towards a "Th1-type" immune response, as opposed to a "Th2-type" immune response. Th1-type responses are typically considered cellular immune system (e.g., cytotoxic lymphocytes) responses, while Th2-type responses are generally "humoral", or antibody-based. Th1-type immune responses are normally characterized by "delayed-type hypersensitivity" reactions to an antigen. Th1-type responses can be detected at the biochemical level by increased levels of Th1-associated cytokines such as IFN-γ, IFN-α, IL-2, IL-12, and TNF-α, as well as IL-6, although IL-6 may also be associated with Th2-type responses as well. Th2-type immune responses are generally associated with higher levels of antibody production, including IgE production, an absence of or minimal CTL production, as well as expression of Th2-associated cytokines such as IL-4 and IL-5.

Immunomodulation in accordance with the invention may be recognized by measurements (assays) in vitro, in vivo and/or ex vivo. Examples of measurable immune responses indicative of immunomodulatory activity include, but are not limited to, antigen-specific antibody production, secretion of cytokines, activation or expansion of lymphocyte populations such as NK cells, CD4+T lymphocytes, CD8+T lymphocytes, B lymphocytes, and the like. See, e.g., WO 97/28259; WO 98/16247; WO 99/11275; Krieg et al. (1995) *Nature* 374:546-549; Yamamoto et al. (1992) *J. Immunol.* 148:4072-4076; Ballas et al. (1996) *J. Immunol.* 157:1840-1845; Klinman et al. (1997) *J. Immunol.* 158:3635-3639; Sato et al. (1996) *Science* 273:352-354; Pisetsky (1996) *J. Immunol.* 156:421-423; Shimada et al. (1986) *Jpn. J. Cancer Res.* 77:808-816; Cowdery et al. (1996) *J. Immunol.* 156:4570-4575; Roman et al. (1997) *Nat Med.* 3:849-54; Lipford et al. (1997) *Eur. J. Immunol.* 27:2340-2344; WO 98/55495, WO 00/61151, Pichyangkul et al. (2001) *J. Imm. Methods* 247:83-94. See also the Examples, infra. Certain useful assays are described herein below for purposes of illustration and not for limitation.

Assays are generally carried out by administering or contacting a cell, tissue, animal or the like with a test sample (e.g., containing a BIC, polynucleotide, and/or other agent) and measuring a response. The test samples containing BICs or polynucleotides can be in a variety of forms or concentrations, which will be understood by the ordinarily skilled practitioner to be appropriate for the assay type. For example, for purposes of a cell-based assay, BICs or polynucleotides are often used at a concentration of 20 µg/ml or 10 µg/ml or 2 µg/ml. Typically, for the purposes of the assay, concentration is determined by measuring absorbance at 260 nm and using the conversion 0.5 $OD_{260}$/ml=20 µg/ml.

It will be understood that positive and negative controls are useful in assays for immunomodulatory activity. A suitable positive control for immunomodulatory activity is the immunomodulatory phosphorothioate DNA having the sequence 5'-TGACTGTGAACGTTCGAGATGA-3' (SEQ ID NO: 134), although other suitable positive controls with immunomodulatory activity will be apparent to the ordinarily skilled practitioner. One suitable negative control is no test agent (i.e., excipient or media alone, also referred to as "cells alone" for certain in vitro assays). Alternatively, a phosphorothioate DNA having the sequence 5'-TGACTGTGAACCTTA-GAGATGA-3' (SEQ ID NO:3) is used as a negative control in some embodiments. Other negative controls can be designed by the practitioner guided by the disclosure herein and ordinary assay design.

One useful class of assays is "cytokine response assays." An exemplary assay for immunomodulatory activity measures the cytokine response of human peripheral blood mononuclear cells ("PBMCs") (e.g., as described in Bohle et al. [1999], *Eur. J. Immunol.* 29:2344-53; Verthelyi et al. [2001] *J. Immunol.* 166:2372-77). In one embodiment of this assay, peripheral blood is collected from one or more healthy human volunteers and PBMCs are isolated. Typically blood is collected by venipuncture using a heparinized syringe, layered onto a FICOLL® (Amersham Pharmacia Biotech) cushion and centrifuged. PBMCs are then collected from the FICOLL® interface and washed twice with cold phosphate buffered saline (PBS). The cells are resuspended and cultured (e.g., in 48- or 96-well plates) at $2 \times 10^6$ cells/mL in RPMI 1640 with 10% heat-inactivated human AB serum, 50 units/mL; penicillin, 50 µg/mL streptomycin, 300 µg/mL glutamine, 1 mM sodium pyruvate, and 1×MEM non-essential amino acids (NEAA) in the presence and absence of test samples or controls for 24 hours.

Cell-free medium is collected from each well and assayed for IFN-γ and/or IFN-α concentration. Immunomodulatory activity is detected when the amount of IFN-γ secreted by PBMCs contacted with the test compound is significantly greater (e.g., at least about 3-fold greater, usually at least about 5-fold greater) than the amount secreted by the PBMCs in the absence of the test compound or, in some embodiments, in the presence of an inactive control compound (e.g., 5'-TGACTGTGAACCTTAGAGATGA-3' (SEQ ID NO:3)). Conversely, a test compound does not have immunomodulatory activity if the amount of IFN-γ secreted by PBMCs contacted with the test compound is not significantly greater (e.g., less than 2-fold greater) than in the absence of the test compound or, alternatively, in the presence of an inactive control compound (e.g., 5'-TGACTGTGAACCTTA-GAGATGA-3' (SEQ ID NO:3)).

When IFN-α concentration is assayed, the amount of IFN-α secreted by PBMCs contacted with the test compound is often significantly greater (e.g., in the case of IFN-α sometimes at least about 2-fold or at least about 3-fold greater) than the amount secreted by the PBMCs in the absence of the test compound or, in some embodiments, in the presence of an inactive control compound (e.g., 5'-TGACTGTGAACCT-TAGAGATGA-3' (SEQ ID NO:3)). In some embodiments, the significantly increased IFN-α secretion level is at least about 5-fold, at least about 10-fold, or even at least about 20-fold greater than controls. Conversely, a test compound does not have immunomodulatory activity if the amount of IFN-α secreted by PBMCs contacted with the test compound is not significantly greater (e.g., less than 2-fold greater) than in the absence of the test compound or, alternatively, in the presence of an inactive control compound (e.g., 5'-TGACT-GTGAACCTTAGAGATGA-3' (SEQ ID NO:3)).

Another useful class of assays are cell proliferation assays, e.g., B cell proliferation assays. The effect of an agent (e.g. a BIC) on B cell proliferation can be determined using any of a variety of assays known in the art. An exemplary B cell proliferation assay is provided in Example 13.

To account for donor variation, e.g., in cell-based assays, such as cytokine and proliferation assays, preferably assays are carried out using cells (e.g., PBMCs) from multiple different donors. The number of donors is usually at least 2 (e.g. 2), preferably at least 4 (e.g. 4), sometimes at least 10 (e.g. 10). Immunomodulatory activity is detected when the amount of IFN-γ secreted in the presence of the test compound (e.g. in at least half of the healthy donors tested, preferably in at least 75%, most preferably in at least 85%) is at least about 3-fold greater or at least about 5-fold greater than secreted in the absence of the test compound, or in some embodiments, than in the presence of an inactive control compound such as described supra.

Immunomodulatory activity may also be detected by measuring interferon-induced changes in expression of cytokines, chemokines and other genes in mammalian cells (e.g., PBMCs, bronchial alveolar lavage (BAL) cells, and other cells responsive to interferon). For example, expression of the chemokines interferon-induced-protein 10 kDa (IP-10), monokine induced by IFN-γ (MIG) and monocyte chemotactic protein 1 (MCP-1) are increased in the presence of IFN-α and IFN-γ. Expression of these proteins, or their corresponding mRNA, may be used as markers of immunostimulatory activity in cultured cells or tissues or blood of animals to which a BIC has been administered. Expression of such markers can be monitored any of a variety of methods of assessing gene expression, including measurement of mRNAs (e.g., by quantitative PCR), immunoassay (e.g., ELISA), and the like.

Biological activity of BICs can also be measured by measuring the induction of gene products known to have antiviral activities, including 2'-5' Oligoadenylate synthetase (2'-5'OAS), Interferon-stimulated gene—54 kD (ISG-54kD), Guanylate binding protein-1 (GBP-1), MxA and MxB. Expression of these proteins, or their corresponding mRNA, may be used as markers of immunostimulatory activity in cultured cells or tissues or blood of animals to which a BIC has been administered. Expression of such markers can be monitored any of a variety of methods of assessing gene expression, including measurement of mRNAs (e.g., by quantitative PCR), immunoassay (e.g., ELISA), and the like.

In vitro assays can also be carried out using mouse cells, for example, as described in Example 12, infra, as well as in other mammalian cells. Exemplary in vivo assays are described in Examples 14 (mice) and 15 (non-human primates).

10. Compositions

In various embodiments, compositions of the invention comprise one or more BICs, (i.e. a single BIC or a combination of two or more BICs) optionally in conjunction with another immunomodulatory agent, such as a peptide, an antigen (described below) and/or an additional adjuvant. Compositions of the invention may comprise a BIC and pharmaceutically acceptable excipient. By "pharmaceutically acceptable" it is meant the carrier, diluent or excipient must be compatible with the other ingredients of the formulation and not deleterious to the recipient thereof. Pharmaceutically acceptable excipients are well known in the art and include sterile water, isotonic solutions such as saline and phosphate buffered saline, and other excipients known in the art. See, e.g., *Remington: The Science and Practice of Pharmacy* (19th edition, 1995, Gennavo, ed.). Adjuvants (an example of which is alum) are known in the art. BIC formulations may be prepared with other immunotherapeutic agents, such as cytokines and antibodies. In some embodiments the composition is isotonic and/or sterile, e.g., suitable for administration to a human patient, e.g., manufactured or formulated under GMP standards. In an embodiment, the BIC is combined with a microcarrier and/or antigen, as described herein. It is also contemplated that, in some embodiments, a BIC composition or formulation of the invention will be free from one or more of (i) a collidal dispersion system, (ii) liposomes, (iii) microcarriers, (iv) polypeptides, (v) antigens, and (vi) endotoxin.

A. BIC/MC Complexes

BICs may be administered in the form of BIC/microcarrier (BIC/MC) complexes. Accordingly, the invention provides compositions comprising BIC/MC complexes.

BIC/MC complexes comprise a BIC bound to the surface of a microcarrier (i.e., the BIC is not encapsulated in the MC), and preferably comprise multiple molecules of BIC bound to each microcarrier. In certain embodiments, a mixture of different BICs may be complexed with a microcarrier, such that the microcarrier is bound to more than one BIC species. The bond between the BIC and MC may be covalent or non-covalent (e.g. mediated by ionic and/or hydrophobic interactions). As will be understood by one of skill in the art, the BIC may be modified or derivatized and the composition of the microcarrier may be selected and/or modified to accommodate the desired type of binding desired for BIC/MC complex formation.

Covalently bonded BIC/MC complexes may be linked using any covalent crosslinking technology known in the art. Typically, the BIC portion will be modified, either to incorporate an additional moiety (e.g., a free amine, carboxyl or sulfhydryl group) or incorporate modified (e.g., phosphorothioate) nucleotide bases to provide a site at which the BIC portion may be linked to the microcarrier. The link between the BIC and MC portions of the complex can be made at the 3' or 5' end of the BIC, or at a suitably modified base at an internal position in the BIC. The microcarrier is generally also modified to incorporate moieties through which a covalent link may be formed, although functional groups normally present on the microcarrier may also be utilized. The BIC/MC is formed by incubating the BIC with a microcarrier under conditions which permit the formation of a covalent complex (e.g., in the presence of a crosslinking agent or by use of an activated microcarrier comprising an activated moiety which will form a covalent bond with the BIC).

A wide variety of crosslinking technologies are known in the art, and include crosslinkers reactive with amino, carboxyl and sulfhydryl groups. As will be apparent to one of skill in the art, the selection of a crosslinking agent and crosslinking protocol will depend on the configuration of the BIC and the microcarrier as well as the desired final configuration of the BIC/MC complex. The crosslinker may be either homobifunctional or heterobifunctional. When a homobifunctional crosslinker is used, the crosslinker exploits the same moiety on the BIC and MC (e.g., an aldehyde crosslinker may be used to covalently link a BIC and MC where both the BIC and MC comprise one or more free amines). Heterobifunctional crosslinkers utilize different moieties on the BIC and MC, (e.g., a maleimido-N-hydroxysuccinimide ester may be used to covalently link a free sulfhydryl on the BIC and a free amine on the MC), and are preferred to minimize formation of inter-microcarrier bonds. In most cases, it is preferable to crosslink through a first crosslinking moiety on the microcarrier and a second crosslinking moiety on the BIC, where the second crosslinking moiety is not present on the microcarrier. One preferred method of producing the BIC/MC complex is by 'activating' the microcarrier by incubating with a heterobifunctional crosslinking agent, then forming the BIC/MC complex by incubating the BIC and activated MC under conditions appropriate for reaction. The crosslinker may incorporate a "spacer" arm between the reactive moieties, or the two reactive moieties in the crosslinker may be directly linked.

In one preferred embodiment, the BIC portion comprises at least one free sulfhydryl (e.g., provided by a 5'-thiol modified base or linker) for crosslinking to the microcarrier, while the microcarrier comprises free amine groups. A heterobifunctional crosslinker reactive with these two groups (e.g., a crosslinker comprising a maleimide group and a NHS-ester), such as succinimidyl 4-(N-maleimidomethyl)cyclohexane-1-carboxylate is used to activate the MC, then covalently crosslink the BIC to form the BIC/MC complex.

Non-covalent BIC/MC complexes may be linked by any non-covalent binding or interaction, including ionic (electrostatic) bonds, hydrophobic interactions, hydrogen bonds, van der Waals attractions, or a combination of two or more different interactions, as is normally the case when a binding pair is to link the BIC and MC.

Preferred non-covalent BIC/MC complexes are typically complexed by hydrophobic or electrostatic (ionic) interactions, or a combination thereof, (e.g., through base pairing between a BIC and a polynucleotide bound to an MC). Due to the hydrophilic nature of the backbone of polynucleotides, BIC/MC complexes which rely on hydrophobic interactions to form the complex generally require modification of the BIC portion of the complex to incorporate a highly hydrophobic moiety. Preferably, the hydrophobic moiety is biocompatible, nonimmunogenic, and is naturally occurring in the individual for whom the composition is intended (e.g., is found in mammals, particularly humans). Examples of preferred hydrophobic moieties include lipids, steroids, sterols such as cholesterol, and terpenes. The method of linking the hydrophobic moiety to the BIC will, of course, depend on the configuration of the BIC and the identity of the hydrophobic moiety. The hydrophobic moiety may be added at any convenient site in the BIC, preferably at either the 5' or 3' end; in the case of addition of a cholesterol moiety to a BIC, the cholesterol moiety is preferably added to the 5' end of the BIC, using conventional chemical reactions (see, for example, Godard et al. (1995) *Eur. J. Biochem.* 232:404-410). Preferably, microcarriers for use in BIC/MC complexes linked by hydrophobic bonding are made from hydrophobic materials, such as oil droplets or hydrophobic polymers, although hydrophilic materials modified to incorporate hydrophobic moieties may be utilized as well. When the microcarrier is a liposome or other liquid phase microcarrier comprising a lumen, the BIC/MC complex is formed by mixing the BIC and the MC after preparation of the MC, in order to avoid encapsulation of the BIC during the MC preparation process.

Non-covalent BIC/MC complexes bound by electrostatic binding typically exploit the highly negative charge of the polynucleotide backbone. Accordingly, microcarriers for use in non-covalently bound BIC/MC complexes are generally positively charged at physiological pH (e.g., about pH 6.8-7.4). The microcarrier may intrinsically possess a positive charge, but microcarriers made from compounds not normally possessing a positive charge may be derivatized or otherwise modified to become positively charged. For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles).

Non-covalent BIC/MC complexes linked by nucleotide base pairing may be produced using conventional methodologies. Generally, base-paired BIC/MC complexes are produced using a microcarrier comprising a bound, preferably a covalently bound, polynucleotide (the "capture polynucleotide") that is at least partially complementary to the BIC. The segment of complementarity between the BIC and the capture nucleotide is preferably at least 6, 8, 10 or 15 contiguous base pairs, more preferably at least 20 contiguous base pairs. The capture nucleotide may be bound to the MC by any method known in the art, and is preferably covalently bound to the BIC at the 5' or 3' end.

In other embodiments, a binding pair may be used to link the BIC and MC in a BIC/MC complex. The binding pair may be a receptor and ligand, an antibody and antigen (or epitope), or any other binding pair which binds at high affinity (e.g., $K_d$ less than about $10^{-8}$). One type of preferred binding pair is biotin and streptavidin or biotin and avidin, which form very tight complexes. When using a binding pair to mediate BIC/MC complex binding, the BIC is derivatized, typically by a covalent linkage, with one member of the binding pair, and the MC is derivatized with the other member of the binding pair. Mixture of the two derivatized compounds results in BIC/MC complex formation.

Many BIC/MC complex embodiments do not include an antigen, and certain embodiments exclude antigen(s) associated with the disease or disorder which is the object of the BIC/MC complex therapy. In further embodiments, the BIC is also bound to one or more antigen molecules. Antigen may be coupled with the BIC portion of a BIC/MC complex in a variety of ways, including covalent and/or non-covalent interactions. Alternately, the antigen may be linked to the microcarrier. The link between the antigen and the BIC in BIC/MC complexes comprising an antigen bound to the BIC can be made by techniques described herein and known in the art.

B. Co-Administered Antigen

In some embodiments, the BIC is coadministered with an antigen. Any antigen may be co-administered with a BIC and/or used for preparation of compositions comprising a BIC and antigen.

In some embodiments, the antigen is an allergen. Examples of recombinant allergens are provided in Table 1. Preparation of many allergens is well-known in the art, including, but not limited to, preparation of ragweed pollen allergen Antigen E (Amb aI) (Rafnar et al. (1991) *J. Biol. Chem.* 266:1229-1236), grass allergen Lol p 1 (Tamborini et al. (1997) *Eur. J. Biochem.* 249:886-894), major dust mite allergens Der pI and Der PII (Chua et al. (1988) *J. Exp. Med.* 167:175-182; Chua et al. (1990) *Int. Arch. Allergy Appl. Immunol.* 91:124-129), domestic cat allergen Fel d I (Rogers et al. (1993) *Mol. Immunol.* 30:559-568), white birch pollen Bet vl (Breiteneder et al. (1989) *EMBO J.* 8:1935-1938), Japanese cedar allergens Cry j 1 and Cry j 2 (Kingetsu et al. (2000) *Immunology* 99:625-629), and protein antigens from other tree pollen (Elsayed et al. (1991) *Scand. J. Clin. Lab. Invest. Suppl.* 204:17-3 1). Preparation of protein antigens from grass pollen for in vivo administration has been reported.

In some embodiments, the allergen is a food allergen, including, but not limited to, peanut allergen, for example Ara h I (Stanley et al. (1996) *Adv. Exp. Med. Biol.* 409:213-216); walnut allergen, for example, Jug r I (Tueber et al. (1998) *J. Allergy Clin. Immunol.* 101:807-814); brazil nut allergen, for example, albumin (Pastorello et al. (1998) *J. Allergy Clin. Immunol.* 102:1021-1027; shrimp allergen, for example, Pen a I (Reese et al. (1997) *Int. Arch. Allergy Immunol.* 113:240-242); egg allergen, for example, ovomucoid (Crooke et al. (1997) *J. Immunol.* 159:2026-2032); milk allergen, for example, bovine β-lactoglobin (Selot al. (1999) *Clin. Exp. Allergy* 29:1055-1063); fish allergen, for example, parvalbumins (Van Do et al. (1999) *Scand. J. Immunol.* 50:619-625; Galland et al. (1998) *J. Chromatogr. B. Biomed. Sci. Appl.* 706:63-71). In some embodiments, the allergen is a latex allergen, including but not limited to, Hev b 7 (Sowka et al. (1998) *Eur. J. Biochem.* 255:213-219). Table 1 shows a list of allergens that may be used.

TABLE 1

RECOMBINANT ALLERGENS

| Group | Allergen | Reference |
|---|---|---|
| ANIMALS: CRUSTACEA | | |
| Shrimp/lobster | tropomyosin | Leung et al. (1996) J. Allergy Clin. Immunol. 98: 954-961 |
| | Pan s I | Leung et al. (1998) Mol. Mar. Biol. Biotechnol. 7: 12-20 |
| INSECTS | | |
| Ant | Sol i 2 (venom) | Schmidt et al. J Allergy Clin Immunol., 1996, 98: 82-8 |
| Bee | Phospholipase A2 (PLA) | Muller et al. J Allergy Clin Immunol, 1995, 96: 395-402 |
| | | Forster et al. J Allergy Clin Immunol, 1995, 95: 1229-35 |
| | | Muller et al. Clin Exp Allergy, 1997, 27: 915-20 |
| | Hyaluronidase (Hya) | Soldatova et al. J Allergy Clin Immunol, 1998, 101: 691-8 |
| Cockroach | Bla g Bd9OK | Helm et al. J Allergy Clin Immunol, 1996, 98: 172-180 |
| | Bla g 4 (a calycin) | Vailes et al. J Allergy Clin Immunol, 1998, 101: 274-280 |
| | Glutathione S-transferase | Arruda et al. J Biol Chem, 1997, 272: 20907-12 |
| | Per a 3 | Wu et al. Mol Immunol, 1997, 34: 1-8 |
| Dust mite | Der p 2 (major allergen) | Lynch et al. J Allergy Clin Immunol, 1998, 101: 562-4 |
| | | Hakkaart et al. Clin Exp Allergy, 1998, 28: 169-74 |
| | | Hakkaart et al. Clin Exp Allergy, 1998, 28: 45-52 |
| | | Hakkaart et al. Int Arch Allergy Immunol, 1998, 115 (2): 150-6 |
| | | Mueller et al. J Biol Chem, 1997, 272: 26893-8 |
| | Der p2 variant | Smith et al. J Allergy Clin Immunol, 1998, 101: 423-5 |
| | Der f2 | Yasue et al. Clin Exp Immunol, 1998, 113: 1-9 |
| | | Yasue et al. Cell Immunol, 1997, 181: 30-7 |
| | Der p10 | Asturias et al. Biochim Biophys Acta, 1998, 1397: 27-30 |
| | Tyr p 2 | Eriksson et al. Eur J Biochem, 1998 |
| Hornet | Antigen 5 aka Dol m V (venom) | Tomalski et al. Arch Insect Biochem Physiol, 1993, 22: 303-13 |
| Mosquito | Aed a I (salivary apyrase) | Xu et al. Int Arch Allergy Immunol, 1998, 115: 245-51 |
| Yellow jacket | antigen 5, hyaluronidase and phospholipase (venom) | King et al. J Allergy Clin Immunol, 1996, 98: 588-600 |
| MAMMALS | | |
| Cat | Fel d I | Slunt et al. J Allergy Clin Immunol, 1995, 95: 1221-8 |
| | | Hoffmann et al. (1997) J Allergy Clin Immunol 99: 227-32 |
| | | Hedlin Curr Opin Pediatr, 1995, 7: 676-82 |
| Cow | Bos d 2 (dander; a lipocalin) | Zeiler et al. J Allergy Clin Immunol, 1997, 100: 721-7 |
| | | Rautiainen et al. Biochem Bioph. Res Comm., 1998, 247: 746-50 |
| | β-lactoglobulin (BLG, major cow milk allergen) | Chatel et al. Mol Immunol, 1996, 33: 1113-8 |
| | | Lehrer et al. Crit Rev Food Sci Nutr, 1996, 36: 553-64 |
| Dog | Can f I and Can f 2, salivary lipocalins | Konieczny et al. Immunology, 1997, 92: 577-86 |
| | | Spitzauer et al. J Allergy Clin Immunol, 1994, 93: 614-27 |
| | | Vrtala et al. J Immunol, 1998, 160: 6137-44 |
| Horse | Equ c1 (major allergen, a lipocalin) | Gregoire et al. J Biol Chem, 1996, 271: 32951-9 |
| Mouse | mouse urinary protein (MUP) | Konieczny et al. Immunology, 1997, 92: 577-86 |
| OTHER MAMMALIAN ALLERGENS | | |
| Insulin | | Ganz et al. J Allergy Clin Immunol, 1990, 86: 45-51 |
| | | Grammer et al. J Lab Clin Med, 1987,109: 141-6 |
| | | Gonzalo et al. Allergy, 1998, 53: 106-7 |
| Interferons | interferon alpha 2c | Detmar et al. Contact Dermatis, 1989, 20: 149-50 |
| MOLLUSCS | topomyosin | Leung et al. J Allergy Clin Immunol, 1996, 98: 954-61 |
| PLANT ALLERGENS: | | |
| Barley | Hor v 9 | Astwood et al. Adv Exp Med Biol, 1996, 409: 269-77 |
| Birch | pollen allergen, Bet v 4 rBet v 1 Bet v 2: (profilin) | Twardosz et al. Biochem Bioph. Res Comm., 1997, 239: 197 |
| | | Pauli et al. J Allergy Clin Immunol, 1996, 97: 1100-9 |
| | | van Neerven et al. Clin Exp Allergy, 1998, 28: 423-33 |
| | | Jahn-Schmid et al. Immunotechnology, 1996, 2: 103-13 |
| | | Breitwieser et al. Biotechniques, 1996, 21: 918-25 |
| | | Fuchs et al. J Allergy Clin Immunol, 1997, 100: 3 56-64 |
| Brazil nut | globulin | Bartolome et al. Allergol Immunopathol, 1997,25: 135-44 |
| Cherry | Pru a I (major allergen) | Scheurer et al. Mol Immunol, 1997, 34: 619-29 |
| Corn | Zml3 (pollen) | Heiss et al. FEBS Lett, 1996, 381: 217-21 |
| | | Lehrer et al. Int Arch Allergy Immunol, 1997, 113: 122-4 |

TABLE 1-continued

RECOMBINANT ALLERGENS

| Group | Allergen | Reference |
|---|---|---|
| Grass | Phl p 1, Phl p 2, Phl p 5 (timothy grass pollen) | Bufe et al. Am J Respir Crit Care Med, 1998, 157: 1269-76<br>Vrtala et al. J Immunol Jun 15, 1998, 160: 6137-44<br>Niederberger et al. J Allergy Clin Immun., 1998, 101: 258-64 |
| | Hol 1 5 velvet grass pollen | Schramm et al. Eur J Biochem, 1998, 252: 200-6 |
| | Bluegrass allergen | Zhang et al. J Immunol, 1993, 151: 791-9 |
| | Cyn d 7 Bermuda grass | Smith et al. Int Arch Allergy Immunol, 1997, 114: 265-71 |
| | Cyn d 12 (a profilin) | Asturias et al. Clin Exp Allergy, 1997, 27: 1307-13<br>Fuchs et al. J Allergy Clin Immunol, 1997, 100: 356-64 |
| Japanese Cedar | Jun a 2 (Juniperus ashei) | Yokoyama et al. Biochem. Biophys. Res. Commun., 2000, 275: 195-202 |
| | Cry j 1, Cry j 2 (Cryptomeria japonica) | Kingetsu et al. Immunology, 2000, 99: 625-629 |
| Juniper | Jun o 2 (pollen) | Tinghino et al. J Allergy Clin Immunol, 1998, 101: 772-7 |
| Latex | Hev b 7 | Sowka et al. Eur J Biochem, 1998, 255: 213-9<br>Fuchs et al. J Allergy Clin Immunol, 1997, 100: 3 56-64 |
| Mercurialis | Mer a I (profilin) | Vallverdu et al. J Allergy Clin Immunol, 1998, 101: 3 63-70 |
| Mustard (Yellow) | Sin a I (seed) | Gonzalez de la Pena et al. Biochem Bioph. Res Comm., 1993, 190: 648-53 |
| Oilseed rape | Bra r I pollen allergen | Smith et al. Int Arch Allergy Immunol, 1997, 114: 265-71 |
| Peanut | Ara h I | Stanley et al. Adv Exp Med Biol, 1996, 409: 213-6<br>Burks et al. J Clin Invest, 1995, 96: 1715-21<br>Burks et al. Int Arch Allergy Immunol, 1995, 107: 248-50 |
| Poa pratensis | Poa p9 | Parronchi et al. Eur J Immunol, 1996, 26: 697-703<br>Astwood et al. Adv Exp Med Biol, 1996, 409: 269-77 |
| Ragweed | Amb a I | Sun et al. Biotechnology Aug, 1995, 13: 779-86<br>Hirschwehr et al. J Allergy Clin Immunol, 1998, 101: 196-206<br>Casale et al. J Allergy Clin Immunol, 1997, 100: 110-21 |
| Rye | Lol p I | Tamborini et al. Eur J Biochem, 1997, 249: 886-94 |
| Walnut | Jug r I | Teuber et al. J Allergy Clin Immun., 1998, 101: 807-14 |
| Wheat | allergen | Fuchs et al. J Allergy Clin Immunol, 1997, 100: 356-64<br>Donovan et al. Electrophoresis, 1993, 14: 917-22 |
| FUNGI: | | |
| *Aspergillus* | Asp f 1, Asp f 2, Asp f3, Asp f 4, rAsp f 6 | Crameri et al. Mycoses, 1998, 41 Suppl 1: 56-60<br>Hemmann et al. Eur J Immunol, 1998, 28: 1155-60<br>Banerjee et al. J Allergy Clin Immunol, 1997, 99: 821-7<br>Crameri Int Arch Allergy Immunol, 1998, 115: 99-114<br>Crameri et al. Adv Exp Med Biol, 1996, 409: 111-6<br>Moser et al. J Allergy Clin Immunol, 1994, 93: 1-11 |
| | Manganese superoxide dismutase (MNSOD) | Mayer et al. Int Arch Allergy Immunol, 1997, 113: 213-5 |
| *Blomia* | allergen | Caraballo et al. Adv Exp Med Biol, 1996, 409: 81-3 |
| *Pencillinium* | allergen | Shen et al. Clin Exp Allergy, 1997, 27: 682-90 |
| *Psilocybe* | Psi c 2 | Horner et al. Int Arch Allergy Immunol, 1995, 107: 298-300 |

In some embodiments, the antigen is from an infectious agent, including protozoan, bacterial, fungal (including unicellular and multicellular), and viral infectious agents. Examples of suitable viral antigens are described herein and are known in the art. Bacteria include Hemophilus influenza, *Mycobacterium tuberculosis* and *Bordetella pertussis*. Protozoan infectious agents include malarial plasmodia, *Leishmania* species, *Trypanosoma* species and *Schistosoma* species. Fungi include *Candida albicans*.

In some embodiments, the antigen is a viral antigen. Viral polypeptide antigens include, but are not limited to, HIV proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like. References discussing influenza vaccination include Scherle and Gerhard (1988) *Proc. Natl. Acad. Sci. USA* 85:4446-4450; Scherle and Gerhard (1986) *J. Exp. Med.* 164:1114-1128; Granoff al. (1993) *Vaccine* 11:S46-51; Kodihalli et al. (1997) *J. Virol.* 71:3391-3396; Ahmeida et al. (1993) *Vaccine* 11:1302-1309; Chen et al. (1999) *Vaccine* 17:653-659; Govorkova and Smirnov (1997) *Acta Virol.* (1997) 41:251-257; Koide et al. (1995) *Vaccine* 13:3-5; Mbawuike et al. (1994) *Vaccine* 12:1340-1348; Tamura et al. (1994) *Vaccine* 12:310-316; Tamura et al. (1992) *Eur. J Immunol.* 22:477-481; Hirabayashi et al. (1990) *Vaccine* 8:595-599. Other examples of antigen polypeptides are group- or sub-group specific antigens, which are known for a number of infectious agents, including, but not limited to, adenovirus, herpes simplex virus, papilloma virus, respiratory syncytial virus and poxviruses.

Many antigenic peptides and proteins are known, and available in the art; others can be identified using conventional techniques. For immunization against tumor formation or treatment of existing tumors, immunomodulatory peptides can include tumor cells (live or irradiated), tumor cell extracts, or protein subunits of tumor antigens such as Her-2/neu, Mart1, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including sperm proteins administered with BICs. Lea et al. (1996) *Biochim. Biophys. Acta* 1307:263.

Attenuated and inactivated viruses are suitable for use herein as the antigen. Preparation of these viruses is well-known in the art and many are commercially available (see, e.g., Physicians' Desk Reference (1998) 52nd edition, Medical Economics Company, Inc.). For example, polio virus is available as IPOL® (Pasteur Merieux Connaught) and ORIMUNE® (Lederle Laboratories), hepatitis A virus as VAQTA® (Merck), measles virus as ATTENUVAX® (Merck), mumps virus as MUMPSVAX® (Merck) and rubella virus as MERUVAX®II (Merck). Additionally, attenuated and inactivated viruses such as HIV-1, HIV-2, herpes simplex virus, hepatitis B virus, rotavirus, human and non-human papillomavirus and slow brain viruses can provide peptide antigens.

In some embodiments, the antigen comprises a viral vector, such as vaccinia, adenovirus, and canary pox.

Antigens may be isolated from their source using purification techniques known in the art or, more conveniently, may be produced using recombinant methods.

Antigenic peptides can include purified native peptides, synthetic peptides, recombinant proteins, crude protein extracts, attenuated or inactivated viruses, cells, micro-organisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) *Hoppe Seylers Z. Physiol. Chem.* 362:833-839. Proteolytic enzymes can also be utilized to couple amino acids to produce peptides. Kullmann (1987) *Enzymatic Peptide Synthesis*, CRC Press, Inc. Alternatively, the peptide can be obtained by using the biochemical machinery of a cell, or by isolation from a biological source. Recombinant DNA techniques can be employed for the production of peptides. Hames et al. (1987) *Transcription and Translation: A Practical Approach*, IRL Press. Peptides can also be isolated using standard techniques such as affinity chromatography.

Preferably the antigens are peptides, lipids (e.g., sterols excluding cholesterol, fatty acids, and phospholipids), polysaccharides such as those used in H. influenza vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

Examples of viral antigens that may be used in the subject compositions and methods using the compositions include, but are not limited to, HIV antigens. Such antigens include, but are not limited to, those antigens derived from HIV envelope glycoproteins including, but not limited to, gp160, gp120 and gp41. Numerous sequences for HIV genes and antigens are known. For example, the Los Alamos National Laboratory HIV Sequence Database collects, curates and annotates HIV nucleotide and amino acid sequences. This database is accessible via the internet, at http://hiv-web.lanl.gov/, and in a yearly publication, see Human Retroviruses and AIDS Compendium (for example, 2000 edition).

Antigens derived from infectious agents may be obtained using methods known in the art, for example, from native viral or bacterial extracts, from cells infected with the infectious agent, from purified polypeptides, from recombinantly produced polypeptides and/or as synthetic peptides.

BICs can be administered in combination with antigen in a variety of ways. In some embodiments, a BIC and antigen are administered spatially proximate with respect to each other. As described below, spatial proximation can be accomplished in a number of ways, including conjugation, encapsidation, via affixation to a platform or adsorption onto a surface. In one embodiment, a BIC and antigen are administered as an admixture (e.g., in solution). It is specifically contemplated that, in certain embodiments, the BIC is not conjugated to an immunogen or antigen.

In some embodiments, the BIC is linked to a polypeptide, e.g., an antigen. The BIC portion can be linked with the antigen portion of a conjugate in a variety of ways, including covalent and/or non-covalent interactions, via the nucleic acid moiety or non-nucleic acid spacer moiety. In some embodiments, linkage is via a reactive group such as, without limitation, thio, amine, carboxylate, aldehyde, hydrizine, hydrizone, disulfide and the like.

The link between the portions can be made at the 3' or 5' end of a nucleic acid moiety, or at a suitably modified base at an internal position in the a nucleic acid moiety. For example, if the antigen is a peptide and contains a suitable reactive group (e.g., an N-hydroxysuccinimide ester) it can be reacted directly with the $N^4$ amino group of cytosine residues. Depending on the number and location of cytosine residues in the BIC, specific coupling at one or more residues can be achieved.

Alternatively, modified oligonucleosides, such as are known in the art, can be incorporated at either terminus, or at internal positions in the BIC. These can contain blocked functional groups which, when deblocked, are reactive with a variety of functional groups which can be present on, or attached to, the antigen of interest.

Where the antigen is a peptide, this portion of the conjugate can be attached to the nucleic acid moiety or spacer moiety through solid support chemistry. For example, a nucleic acid portion of a BIC can be added to a polypeptide portion that has been pre-synthesized on a support. Haralambidis et al. (1990) *Nucleic Acids Res.* 18:493-499; and Haralambidis et al. (1990) *Nucleic Acids Res.* 18:501-505.

Alternatively, the BIC can be synthesized such that it is connected to a solid support through a cleavable linker extending from the 3'-end of a nucleic acid moiety. Upon chemical cleavage of the BIC from the support, a terminal thiol group or a terminal amino group is left at the 3'-end of the nucleic acid moiety (Zuckermann et al., 1987, *Nucleic Acids Res.* 15:5305-5321; Corey et al., 1987, *Science* 238:1401-1403; Nelson et al., 1989, *Nucleic Acids Res.* 17:1781-1794). Conjugation of the amino-modified BIC to amino groups of the peptide can be performed as described in Benoit et al. (1987) *Neuromethods* 6:43-72. Conjugation of the thiol-modified BIC to carboxyl groups of the peptide can be performed as described in Sinah et al. (1991) *Oligonucleotide Analogues: A Practical Approach*, IRL Press. Coupling of a nucleic acid moiety or spacer carrying an appended maleimide to the thiol side chain of a cysteine residue of a peptide has also been described. Tung et al. (1991) *Bioconjug. Chem.* 2:464-465.

The peptide portion of the conjugate can be attached to a free 5'-end of a nucleic acid moiety through an amine, thiol, or carboxyl group that has been incorporated into nucleic acid moiety or spacer (e.g., via a free 5'-end, a 3'-end, via a modified base, and the like).

Conveniently, a linking group comprising a protected amine, thiol, or carboxyl at one end, and a phosphoramidite can be covalently attached to a hydroxyl group of a BIC. Agrawal et al. (1986) *Nucleic Acids Res.* 14:6227-6245; Connolly (1985) *Nucleic Acids Res.* 13:4485-4502; Kremsky et al. (1987) *Nucleic Acids Res.* 15:2891-2909; Connolly (1987) *Nucleic Acids Res.* 15:3131-3139; Bischoff et al. (1987) *Anal. Biochem.* 164:336-344; Blanks et al. (1988) *Nucleic Acids Res.* 16:10283-10299; and U.S. Pat. Nos. 4,849,513, 5,015,733, 5,118,800, and 5,118,802. Subsequent to deprotection, the amine, thiol, and carboxyl functionalities can be used to covalently attach the BIC to a peptide. Benoit et al. (1987); and Sinah et al. (1991).

A BIC-antigen conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of a BIC. Roget et al. (1989) *Nucleic Acids Res.* 17:7643-7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving a BIC and residues within the antigen, such as charged amino acids, or through the use of a linker portion comprising charged residues that can interact with both the oligonucleotide and the antigen. For example, non-covalent conjugation can occur between a generally negatively-charged BIC and positively-charged amino acid residues of a peptide, e.g., polylysine, polyarginine and polyhistidine residues.

Non-covalent conjugation between BIC and antigens can occur through DNA binding motifs of molecules that interact with DNA as their natural ligands. For example, such DNA binding motifs can be found in transcription factors and anti-DNA antibodies.

The linkage of the BIC to a lipid can be formed using standard methods. These methods include, but are not limited to, the synthesis of oligonucleotide-phospholipid conjugates (Yanagawa et al. (1988) *Nucleic Acids Symp. Ser.* 19:189-192), oligonucleotide-fatty acid conjugates (Grabarek et al. (1990) *Anal. Biochem.* 185:131-135; and Staros et al. (1986) *Anal. Biochem.* 156:220-222), and oligonucleotide-sterol conjugates. Boujrad et al. (1993) *Proc. Natl. Acad. Sci. USA* 90:5728-5731.

The linkage of the oligonucleotide to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J. Applied Biochem.* 7:347-355.

Additional methods for the attachment of peptides and other molecules to oligonucleotides can be found in U.S. Pat. No. 5,391,723; Kessler (1992) "Nonradioactive labeling methods for nucleic acids" in Kricka (ed.) *Nonisotopic DNA Probe Techniques*, Academic Press; and Geoghegan et al. (1992) *Bioconjug. Chem.* 3:138-146.

A BIC may be proximately associated with an antigen(s) in other ways. In some embodiments, a BIC and antigen are proximately associated by encapsulation. In other embodiments, a BIC and antigen are proximately associated by linkage to a platform molecule. A "platform molecule" (also termed "platform") is a molecule containing sites which allow for attachment of the a BIC and antigen(s). In other embodiments, a BIC and antigen are proximately associated by adsorption onto a surface, preferably a carrier particle.

In some embodiments, the methods of the invention employ an encapsulating agent that can maintain the proximate association of the a BIC and first antigen until the complex is available to the target (or compositions comprising such encapsulating agents). Preferably, the composition comprising a BIC, antigen and encapsulating agent is in the form of adjuvant oil-in-water emulsions, microparticles and/or liposomes. More preferably, adjuvant oil-in-water emulsions, microparticles and/or liposomes encapsulating a BIC are in the form of particles from about 0.04 µm to about 100 µm in size, preferably any of the following ranges: from about 0.1 µm to about 20 µm; from about 0.15 µm to about 10 µm; from about 0.05 µm to about 1.00 µm; from about 0.05 µm to about 0.5 µm.

Colloidal dispersion systems, such as microspheres, beads, macromolecular complexes, nanocapsules and lipid-based systems, such as oil-in-water emulsions, micelles, mixed micelles and liposomes can provide effective encapsulation of BIC-containing compositions.

The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Polypeptides suitable for encapsulation components include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect a BIC-containing composition to preserve the immunomodulatory activity thereof. Examples of binding proteins include, but are not limited to, albumins such as bovine serum albumin (BSA) and pea albumin.

Other suitable polymers can be any known in the art of pharmaceuticals and include, but are not limited to, naturally-occurring polymers such as dextrans, hydroxyethyl starch, and polysaccharides, and synthetic polymers. Examples of naturally occurring polymers include proteins, glycopeptides, polysaccharides, dextran and lipids. The additional polymer can be a synthetic polymer. Examples of synthetic polymers which are suitable for use in the present invention include, but are not limited to, polyalkyl glycols (PAG) such as PEG, polyoxyethylated polyols (POP), such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

The PEGs for use in encapsulation compositions of the present invention are either purchased from chemical suppliers or synthesized using techniques known to those of skill in the art.

The term "LMS", as used herein, means lamellar lipid particles wherein polar head groups of a polar lipid are arranged to face an aqueous phase of an interface to form membrane structures. Examples of the LMSs include liposomes, micelles, cochleates (i.e., generally cylindrical liposomes), microemulsions, unilamellar vesicles, multilamellar vesicles, and the like.

One colloidal dispersion system that may be used in the administration of BICs is a liposome. In mice immunized with a liposome-encapsulated antigen, liposomes appeared to enhance a Th1-type immune response to the antigen. Aramaki et al. (1995) *Vaccine* 13:1809-1814. As used herein, a "liposome" or "lipid vesicle" is a small vesicle bounded by at least one and possibly more than one bilayer lipid membrane. Liposomes are made artificially from phospholipids, glycolipids, lipids, steroids such as cholesterol, related molecules, or a combination thereof by any technique known in the art, including but not limited to sonication, extrusion, or removal of detergent from lipid-detergent complexes. One type of liposome for use in delivering BICs to cells is cationic liposomes. A liposome can also optionally comprise additional components, such as a tissue targeting component. It is understood that a "lipid membrane" or "lipid bilayer" need not consist exclusively of lipids, but can additionally contain any suitable other components, including, but not limited to, cholesterol and other steroids, lipid-soluble chemicals, proteins of any length, and other amphipathic molecules, providing the general structure of the membrane is a sheet of two hydrophilic surfaces sandwiching a hydrophobic core. For a general discussion of membrane structure, see *The Encyclopedia of Molecular Biology* by J. Kendrew (1994). For suitable lipids see e.g., Lasic (1993) "Liposomes: from Physics to Applications" Elsevier, Amsterdam.

Processes for preparing liposomes containing BIC-containing compositions are known in the art. The lipid vesicles can be prepared by any suitable technique known in the art. Methods include, but are not limited to, microencapsulation, microfluidization, LLC method, ethanol injection, freon injection, the "bubble" method, detergent dialysis, hydration, sonication, and reverse-phase evaporation. Reviewed in Watwe et al. (1995) *Curr. Sci.* 68:715-724. Techniques may be combined in order to provide vesicles with the most desirable attributes.

The invention encompasses use of LMSs containing tissue or cellular targeting components. Such targeting components are components of a LMS that enhance its accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art.

The LMSs can be targeted to any cell type toward which a therapeutic treatment is to be directed, e.g., a cell type which can modulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

The LMS compositions of the present invention can additionally comprise surfactants. Surfactants can be cationic, anionic, amphiphilic, or nonionic. A preferred class of surfactants are nonionic surfactants; particularly preferred are those that are water soluble.

In some embodiments a BIC and antigen are proximately associated by linkage to a platform molecule, such as a proteinaceous or non-proteinaceous (e.g., synthetic) valency platform. Examples of suitable platforms are described supra, in the discussion of valency platforms used as a spacer moiety in a BIC. Attachment of antigens to valency platforms can be carried out using routine methods. As an example, polypeptides contain amino acid side chain moieties with functional groups such as amino, carboxyl or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s) (or if the antigen is a carbohydrate), functional amino, sulfhydryl and/or aldehyde groups may be incorporated therein by conventional chemistry. For instance, primary amino groups may be incorporated by reaction of the oxidized sugar with ethylenediamine in the presence of sodium cyanoborohydride, sulfhydryls may be introduced by reaction of cysteamine dihydrochloride followed by reduction with a standard disulfide reducing agent, while aldehyde groups may be generated following periodate oxidation. In a similar fashion, the platform molecule may also be derivatized to contain functional groups if it does not already possess appropriate functional groups.

In another embodiment, a BIC and antigen are coadministered by adsorbing both to a surface, such as a nanoparticle or microcarrier. Adsorption of a BIC and/or antigen to a surface may occur through non-covalent interactions, including ionic and/or hydrophobic interactions. Adsorption of polynucleotides and polypeptides to a surface for the purpose of delivery of the adsorbed molecules to cells is well known in the art. See, for example, Douglas et al. (1987) *Crit. Rev. Ther. Drug. Carrier Syst.* 3:233-261; Hagiwara et al. (1987) In Vivo 1:241-252; Bousquet et al. (1999) *Pharm. Res.* 16:141-147; and Kossovsky et al., U.S. Pat. No. 5,460,831. Preferably, the material comprising the adsorbent surface is biodegradable.

In general, characteristics of nanoparticles, such as surface charge, particle size and molecular weight, depend upon polymerization conditions, monomer concentration and the presence of stabilizers during the polymerization process (Douglas et al., 1987, supra). The surface of carrier particles may be modified, for example, with a surface coating, to allow or enhance adsorption of the BIC and/or antigen. Carrier particles with adsorbed BIC and/or antigen may be further coated with other substances. The addition of such other substances may, for example, prolong the half-life of the particles once administered to the subject and/or may target the particles to a specific cell type or tissue, as described herein.

Nanocrystalline surfaces to which a BIC and antigen may be adsorbed have been described (see, for example, U.S. Pat. No. 5,460,831). Nanocrystalline core particles (with diameters of 1 μm or less) are coated with a surface energy modifying layer that promotes adsorption of polypeptides, polynucleotides and/or other pharmaceutical agents. As described in U.S. Pat. No. 5,460,831, for example, a core particle is coated with a surface that promotes adsorption of an oligonucleotide and is subsequently coated with an antigen preparation, for example, in the form of a lipid-antigen mixture. Such nanoparticles are self-assembling complexes of nanometer sized particles, typically on the order of 0.1 μm, that carry an inner layer of BIC and an outer layer of antigen.

Another adsorbent surface are nanoparticles made by the polymerization of alkylcyanoacrylates. Alkylcyanoacrylates can be polymerized in acidified aqueous media by a process of anionic polymerization. Depending on the polymerization conditions, the small particles tend to have sizes in the range of 20 to 3000 nm, and it is possible to make nanoparticles specific surface characteristics and with specific surface charges (Douglas et al., 1987, supra). For example, oligonucleotides may be adsorbed to polyisobutyl- and polyisohexlcyanoacrylate nanoparticles in the presence of hydrophobic cations such as tetraphenylphosphonium chloride or quaternary ammonium salts, such as cetyltrimethyl ammonium bromide. Oligonucleotide adsorption on these nanoparticles appears to be mediated by the formation of ion pairs between negatively charged phosphate groups of the nucleic acid chain and the hydrophobic cations. See, for example, Lambert et al. (1998) *Biochimie* 80:969-976, Chavany et al. (1994) *Pharm. Res.* 11:1370-1378; Chavany et al. (1992) *Pharm. Res.* 9:441-449. Polypeptides may also be adsorbed to polyalkylcyanoacrylate nanoparticles. See, for example, Douglas et al., 1987; Schroeder et al. (1998) *Peptides* 19:777-780.

Another adsorbent surface are nanoparticles made by the polymerization of methylidene malonate. For example, as described in Bousquet et al., 1999, polypeptides adsorbed to poly(methylidene malonate 2.1.2) nanoparticles appear to do so initially through electrostatic forces followed by stabilization through hydrophobic forces.

C. Additional Adjuvants

A BIC may also be administered in conjunction with an adjuvant. Administration of an antigen with a BIC and an adjuvant leads to a potentiation of a immune response to the antigen and thus, can result in an enhanced immune response compared to that which results from a composition comprising the BIC and antigen alone. Adjuvants are known in the art and include, but are not limited to, oil-in-water emulsions, water-in oil emulsions, alum (aluminum salts), liposomes and microparticles, including but not limited to, polystyrene, starch, polyphosphazene and polylactide/polyglycosides. Other suitable adjuvants also include, but are not limited to, MF59, DETOX™ (Ribi), squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873-875, as well as, lipid-based adjuvants and others described herein. For veterinary use and for production of antibodies in animals, mitogenic components of Freund's adjuvant (both complete and incomplete) can be used.

IV. Methods of the Invention

The invention provides methods of modulating an immune response of an animal or population of cells, e.g., mammalian, optionally human, blood cells (e.g., PBMCs, lymphocytes, dendritic cells), bronchial alveolar lavage cells, or other cells or cell populations containing cells responsive to immunostimulatory agents, by contacting the cells with a BIC or BIC-containing composition described herein (e.g., a composition containing a BIC, BIC and an antigen, a BIC-antigen conjugate, a BIC/microcarrier complex, etc.) The modulation can be accomplished by any form of contacting, including without limitation, co-incubation of cells and BIC in vitro, application of the BIC to skin of a mammal (e.g., of an experimental animal), and parenteral administration.

An immune response in animals or cell populations can be detected in any number of ways, including a increased expression of one or more of IFN-γ, IFN-α, IL-2, IL-12, TNF-α, IL-6, IL-4, IL-5, IP-10, ISG-54K, MCP-1, or a change in gene expression profile characteristic of immune stimulation (see, e.g., Example 43) as well as responses such as B cell proliferation and dendritic cell maturation, The ability to stimulate an immune response in a cell population has a number of uses, e.g., in an assay system for immunosuppressive agents.

Thus, the invention provides methods of modulating an immune response in an individual, preferably a mammal, more preferably a human, comprising administering to the individual a BIC as described herein. Immunomodulation may include stimulating a Th1-type immune response and/or inhibiting or reducing a Th2-type immune response. The BIC is administered in an amount sufficient to modulate an immune response. As described herein, modulation of an immune response may be humoral and/or cellular, and is measured using standard techniques in the art and as described herein.

In certain embodiments, the individual suffers from a disorder associated with a Th2-type immune response, such as (without limitation) allergies, allergy-induced asthma, atopic dermatitis, eosinophillic gastrointestinal inflammation, eosinophillic esophagitis, and allergic bronchopulmonary aspergillosis. Administration of a BIC results in immunomodulation, increasing levels of one or more Th1-type response associated cytokines, which may result in a reduction of the Th2-type response features associated with the individual's response to the allergen. Immunomodulation of individuals with Th2-type response associated disorders results in a reduction or improvement in one or more of the symptoms of the disorder. Where the disorder is allergy or allergy-induced asthma, improvement in one or more of the symptoms includes a reduction one or more of the following: rhinitis, allergic conjunctivitis, circulating levels of IgE, circulating levels of histamine and/or requirement for 'rescue' inhaler therapy (e.g., inhaled albuterol administered by metered dose inhaler or nebulizer).

In further embodiments, the individual subject to the immunomodulatory therapy of the invention is an individual receiving a vaccine. The vaccine may be a prophylactic vaccine or a therapeutic vaccine. A prophylactic vaccine comprises one or more epitopes associated with a disorder for which the individual may be at risk (e.g., *M. tuberculosis* antigens as a vaccine for prevention of tuberculosis). Therapeutic vaccines comprise one or more epitopes associated with a particular disorder affecting the individual, such as *M. tuberculosis* or *M. bovis* surface antigens in tuberculosis patients, antigens to which the individual is allergic (i.e., allergy desensitization therapy) in individuals subject to allergies, tumor cells from an individual with cancer (e.g., as described in U.S. Pat. No. 5,484,596), or tumor associated antigens in cancer patients. The BIC may be given in conjunction with the vaccine (e.g., in the same injection or a contemporaneous, but separate, injection) or the BIC may be administered separately (e.g., at least 12 hours before or after administration of the vaccine). In certain embodiments, the antigen(s) of the vaccine is part of the BIC, by either covalent or non-covalent linkage to the BIC. Administration of BIC therapy to an individual receiving a vaccine results in an immune response to the vaccine that is shifted towards a Th1-type response as compared to individuals which receive vaccine not containing a BIC. Shifting towards a Th1-type response may be recognized by a delayed-type hypersensitivity (DTH) response to the antigen(s) in the vaccine, increased IFN-γ and other Th1-type response associated cytokines, production of CTLs specific for the antigen(s) of the vaccine, low or reduced levels of IgE specific for the antigen(s) of the vaccine, a reduction in Th2-associated antibodies specific for the antigen(s) of the vaccine, and/or an increase in Th1-associated antibodies specific for the antigen(s) of the vaccine. In the case of therapeutic vaccines, administration of BIC and vaccine also results in amelioration of one or more symptoms of the disorder which the vaccine is intended to treat. As will be apparent to one of skill in the art, the exact symptoms and manner of their improvement will depend on the disorder sought to be treated. For example, where the therapeutic vaccine is for tuberculosis, BIC treatment with vaccine results in reduced coughing, pleural or chest wall pain, fever, and/or other symptoms known in the art. Where the vaccine is an allergen used in allergy desensitization therapy, the treatment results in a reduction in the symptoms of allergy (e.g., reduction in rhinitis, allergic conjunctivitis, circulating levels of IgE, and/or circulating levels of histamine).

The compositions of the invention may also be used prophylactically to increase resistance to infection by a wide range of bacterial or viral pathogens, including natural of genetically modified organisms employed as agents of biological warfare or terrorism.

Other embodiments of the invention relate to immunomodulatory therapy of individuals having a pre-existing disease or disorder, such as cancer or an infectious disease. Cancer is an attractive target for immunomodulation because most cancers express tumor-associated and/or tumor specific antigens which are not found on other cells in the body. Stimulation of a Th1-type response against tumor cells results in direct and/or bystander killing of tumor cells by the immune system, leading to a reduction in cancer cells and a reduction in symptoms. Administration of a BIC to an individual having cancer results in stimulation of a Th1-type immune response against the tumor cells. Such an immune response can kill tumor cells, either by direct action of cellular immune system cells (e.g., CTLs) or components of the humoral immune system, or by bystander effects on cells proximal to cells targeted by the immune system including macrophages and natural killer (NK) cells. See, for example, Cho et al. (2000) *Nat. Biotechnol.* 18:509-514. In treatment of a pre-existing disease or disorder, the BIC can be administered in conjunction with other immunotherapeutic agents such as cytokines, adjuvants and antibodies. For example, a BIC can be administered as part of a therapeutic regimen that includes administration of a binding agent that binds an antigen displayed by tumor cells. Exemplary binding agents include polyclonal and monoclonal antibodies. Examples of target antigens include CD20, CD22, HER2 and others known in the art or to be discovered in the future. Without intending to be bound by theory, it is believed that the BIC enhances killing of tumor cells to which the binding agent is associated (e.g., by enhancing antibody dependent cellular cytotoxicity and/or effector function). The binding agent can optionally be labeled, e.g., with a radioisotope or toxin that damages a cell to which the binding agent is bound. The BIC may be given in conjunction with the agent (e.g., at the same time) or before or after (e.g., less than 24 hours before or after administration of the agent). For example, in the case of cancer, the BIC can be administered in conjunction with a chemotherapeutic agent known or suspected of being effective for the treatment of cancer. As another example, the BIC can be administered in conjunction with radiation therapy, gene therapy, or the like. The BIC may be any of those described herein.

Immunomodulatory therapy in accordance with the invention can also be used in individuals with infectious diseases, particularly infectious diseases which are resistant to humoral immune responses (e.g., diseases caused by mycobacterial infections and intracellular pathogens). Immunomodulatory therapy may be used for the treatment of infectious diseases caused by cellular pathogens (e.g., bacteria or protozoans) or by subcellular pathogens (e.g., viruses). BIC therapy may be administered to individuals suffering from mycobacterial diseases such as tuberculosis (e.g., *M. tuberculosis* and/or *M. bovis* infections), leprosy (i.e., *M. leprae* infections), or *M. marinum* or *M. ulcerans* infections. BIC therapy can also be used for the treatment of viral infections, including infections by influenza virus, respiratory syncytial virus (RSV), hepatitis virus B, hepatitis virus C, herpes viruses, particularly herpes simplex viruses, and papilloma viruses. Diseases caused by intracellular parasites such as malaria (e.g., infection by *Plasmodium vivax, P. ovale, P. falciparum* and/or *P. malariae*), leishmaniasis (e.g., infection by *Leishmania donovani, L. tropica, L. mexicana, L. braziliensis, L. peruviana, L. infantum, L. chagasi*, and/or L. aethiopica), and toxoplasmosis (i.e., infection by *Toxoplasmosis gondii*) also benefit from BIC therapy. BIC therapy can also be used for treatment of parasitic diseases such as schistosomiasis (i.e., infection by blood flukes of the genus *Schistosoma* such as *S. haematobium, S. mansoni, S. japonicum*, and *S. mekongi*) and clonorchiasis (i.e., infection by *Clonorchis sinensis*). Administration of a BIC to an individual suffering from an infectious disease results in an anelioration of symptoms of the infectious disease. In some embodiments, the infectious disease is not a viral disease.

The invention further provides methods of increasing or stimulating at least one Th1-associated cytokine in an individual, including IL-2, IL-12, TNF-α, IFN-γ and IFN-α. In certain embodiments, the invention provides methods of increasing or stimulating IFN-γ in an individual, particularly in an individual in need of increased IFN-γ levels, by administering an effective amount of a BIC to the individual. Individuals in need of increased IFN-γ are those having disorders which respond to the administration of IFN-γ. Such disorders include a number of inflammatory disorders including, but not limited to, ulcerative colitis. Such disorders also include a number of fibrotic disorders, including, but not limited to, idiopathic pulmonary fibrosis (IPF), scleroderma, cutaneous radiation-induced fibrosis, hepatic fibrosis including schistosomiasis-induced hepatic fibrosis, renal fibrosis as well as other conditions which may be improved by administration of IFN-γ. An increase in IFN-γ levels may result in amelioration of one or more symptoms, stabilization of one or more symptoms, or prevention of progression (e.g., reduction or elimination of additional lesions or symptoms) of the disorder which responds to IFN-γ. The methods of the invention may be practiced in combination with other therapies which make up the standard of care for the disorder, such as administration of anti-inflammatory agents such as systemic corticosteroid therapy (e.g., cortisone) in IPF.

In certain embodiments, the invention provides methods of increasing IFN-α in an individual, particularly in an individual in need of increased IFN-α levels, by administering an effective amount of a BIC to the individual such that IFN-α levels are increased. Individuals in need of increased IFN-α are those having disorders which respond to the administration of IFN-α, including recombinant IFN-α, including, but not limited to, viral infections and cancer.

Administration of a BIC in accordance with certain embodiments of the invention results in an increase in IFN-α levels, and results in amelioration of one or more symptoms, stabilization of one or more symptoms, or prevention of progression (e.g., reduction or elimination of additional lesions or symptoms) of the disorder which responds to IFN-α. The methods of the invention may be practiced in combination with other therapies which make up the standard of care for the disorder, such as administration of anti-viral agents for viral infections.

Also provided are methods of reducing levels, particularly serum levels, of IgE in an individual having an IgE-related disorder by administering an effective amount of a BIC to the individual. In such methods, the BIC may be administered alone (e.g., without antigen) or administered with antigen, such as an allergen. An IgE-related disorder is a condition, disorder, or set of symptoms ameliorated by a reduction in IgE levels. Reduction in IgE results in an amelioration of symptoms of the IgE-related disorder. Such symptoms include allergy symptoms such as rhinitis, conjunctivitis, in decreased sensitivity to allergens, a reduction in the symptoms of allergy in an individual with allergies, or a reduction in severity of an allergic response.

Methods of the invention includes embodiments in which BICs are administered in the form of a BIC/microcarrier complex(s).

In some embodiments, the invention provides methods of stimulating CTL production in an individual, comprising administering an effective amount of a BIC to the individual such that CTL production is increased.

As will be apparent to one of skill in the art, the methods of the invention may be practiced in combination with other therapies for the particular indication for which the BIC is administered. For example, BIC therapy may be administered in conjunction with anti-malarial drugs such as chloroquine for malaria patients, in conjunction with leishmanicidal drugs such as pentamidine and/or allopurinol for leishmaniasis patients, in conjunction with anti-mycobacterial drugs such as isoniazid, rifampin and/or ethambutol in tuberculosis patients, or in conjunction with allergen desensitization therapy for atopic (allergy) patients.

1. Administration and Assessment of the Immune Response

The BIC can be administered in combination with pharmaceutical and/or immunogenic and/or other immunomodulatory agents, as described herein, and can be combined with a physiologically acceptable carrier thereof.

For example, a BIC or composition of the invention can be administered in conjunction with other immunotherapeutic agents such as cytokines, adjuvants and antibodies. The BIC may be given in conjunction with the agent (e.g., at the same time, or before or after (e.g., less than 24 hours before or after administration of the agent). The BIC may be any of those described herein.

As with all immunomodulatory compositions, the immunologically effective amounts and method of administration of the particular BIC formulation can vary based on the individual, what condition is to be treated and other factors evident to one skilled in the art. Factors to be considered include the presence of a coadministered antigen, whether or not the BIC will be administered with or covalently attached to an adjuvant or delivery molecule, route of administration and the number of immunizing doses to be administered. Such factors are known in the art and it is well within the skill of those in the art to make such determinations without undue experimentation. A suitable dosage range is one that provides the desired modulation of immune response to the antigen. Generally, dosage is determined by the amount of BIC administered to the patient, rather than the overall quantity of BIC. Exemplary dosage ranges of the BIC, given in amounts of BIC delivered, may be, for example, from about any of the following: 1 to 500 µg/kg, 100 to 400 µg/kg, 200 to 300 µg/kg, 1 to 100 µg/kg, 100 to 200 µg/kg, 300 to 400 µg/kg, 400 to 500 µg/kg. The absolute amount given to each patient depends on pharmacological properties such as bioavailability, clearance rate and route of administration.

The effective amount and method of administration of the particular BIC formulation can vary based on the individual patient and the stage of the disease and other factors evident to one skilled in the art. The route(s) of administration suited for a particular application will be known to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient BIC-containing composition to attain a tissue concentration of about 1-10 µM as measured by blood levels. The absolute amount given to each patient depends on pharmacological properties such as bioavailability, clearance rate and route of administration.

As described herein, APCs and tissues with high concentration of APCs are preferred targets for the BIC. Thus, administration of BIC to mammalian skin and/or mucosa, where APCs are present in relatively high concentration, is preferred.

The present invention provides BIC formulations suitable for topical application including, but not limited to, physiologically acceptable implants, ointments, creams, rinses and gels. Topical administration is, for instance, by a dressing or bandage having dispersed therein a delivery system, by direct administration of a delivery system into incisions or open wounds, or by transdermal administration device directed at a site of interest. Creams, rinses, gels or ointments having dispersed therein a BIC are suitable for use as topical ointments or wound filling agents.

Preferred routes of dermal administration are those which are least invasive. Preferred among these means are transdermal transmission, epidermal administration and subcutaneous injection. Of these means, epidermal administration is preferred for the greater concentrations of APCs expected to be in intradermal tissue.

Transdermal administration is accomplished by application of a cream, rinse, gel, etc. capable of allowing the BIC to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference.

For transdermal transmission, iontophoresis is a suitable method. Iontophoretic transmission can be accomplished using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or periodically. Preparation and use of the patch should be performed according to the manufacturer's printed instructions which accompany the LECTRO PATCH product; those instructions are incorporated herein by this reference. Other occlusive patch systems are also suitable.

For transdermal transmission, low-frequency ultrasonic delivery is also a suitable method. Mitragotri et al. (1995)

*Science* 269:850-853. Application of low-frequency ultrasonic frequencies (about 1 MHz) allows the general controlled delivery of therapeutic compositions, including those of high molecular weight.

Epidermal administration essentially involves mechanically or chemically irritating the outermost layer of the epidermis sufficiently to provoke an immune response to the irritant. Specifically, the irritation should be sufficient to attract APCs to the site of irritation.

An exemplary mechanical irritant means employs a multiplicity of very narrow diameter, short tines which can be used to irritate the skin and attract APCs to the site of irritation, to take up BIC transferred from the end of the tines. For example, the MONO-VACC old tuberculin test manufactured by Pasteur Merieux of Lyon, France contains a device suitable for introduction of BIC-containing compositions.

The device (which is distributed in the U.S. by Connaught Laboratories, Inc. of Swiftwater, Pa.) consists of a plastic container having a syringe plunger at one end and a tine disk at the other. The tine disk supports a multiplicity of narrow diameter tines of a length which will just scratch the outermost layer of epidermal cells. Each of the tines in the MONO-VACC kit is coated with old tuberculin; in the present invention, each needle is coated with a pharmaceutical composition of a BIC formulation. Use of the device is preferably according to the manufacturer's written instructions included with the device product. Similar devices which can also be used in this embodiment are those which are currently used to perform allergy tests.

Another suitable approach to epidermal administration of BIC is by use of a chemical which irritates the outermost cells of the epidermis, thus provoking a sufficient immune response to attract APCs to the area. An example is a keratinolytic agent, such as the salicylic acid used in the commercially available topical depilatory creme sold by Noxema Corporation under the trademark NAIR. This approach can also be used to achieve epithelial administration in the mucosa. The chemical irritant can also be applied in conjunction with the mechanical irritant (as, for example, would occur if the MONO-VACC type tine were also coated with the chemical irritant). The BIC can be suspended in a carrier which also contains the chemical irritant or coadministered therewith.

Parenteral routes of administration include but are not limited to electrical (iontophoresis) or direct injection such as direct injection into a central venous line, intravenous, intramuscular, intraperitoneal, intradermal, or subcutaneous injection. Formulations of BIC suitable for parenteral administration are generally formulated in USP water or water for injection and may further comprise pH buffers, salts bulking agents, preservatives, and other pharmaceutically acceptable excipients. BICs for parenteral injection may be formulated in pharmaceutically acceptable sterile isotonic solutions such as saline and phosphate buffered saline for injection.

Gastrointestinal routes of administration include, but are not limited to, ingestion and rectal. The invention includes formulations BIC suitable for gastrointestinal administration including, but not limited to, pharmaceutically acceptable powders, pills or liquids for ingestion and suppositories for rectal administration. As will be apparent to one of skill in the art, pills or suppositories will further comprise pharmaceutically acceptable solids, such as starch, to provide bulk for the composition.

Naso-pharyngeal and pulmonary administration include are accomplished by inhalation, and include delivery routes such as intranasal, transbronchial and transalveolar routes. The invention includes formulations of BIC suitable for administration by inhalation including, but not limited to, liquid suspensions for forming aerosols as well as powder forms for dry powder inhalation delivery systems. Devices suitable for administration by inhalation of BIC formulations include, but are not limited to, atomizers, vaporizers, nebulizers, and dry powder inhalation delivery devices.

The choice of delivery routes can be used to modulate the immune response elicited. For example, IgG titers and CTL activities were identical when an influenza virus vector was administered via intramuscular or epidermal (gene gun) routes; however, the muscular inoculation yielded primarily IgG2a, while the epidermal route yielded mostly IgG1. Pertmer et al. (1996) *J. Virol.* 70:6119-6125. Thus, one skilled in the art can take advantage of slight differences in immunogenicity elicited by different routes of administering the immunomodulatory oligonucleotides of the present invention.

The above-mentioned compositions and methods of administration are meant to describe but not limit the methods of administering the formulations of BIC of the invention. The methods of producing the various compositions and devices are within the ability of one skilled in the art and are not described in detail here.

Analysis (both qualitative and quantitative) of the immune response to BIC can be by any method known in the art, including, but not limited to, measuring antigen-specific antibody production (including measuring specific antibody +subclasses), activation of specific populations of lymphocytes such as CD4+T cells, NK cells or CTLs, production of cytokines such as IFN-γ, IFN-α, IL-2, IL-4, IL-5, IL-10 or IL-12 and/or release of histamine. Methods for measuring specific antibody responses include enzyme-linked immunosorbent assay (ELISA) and are well known in the art. Measurement of numbers of specific types of lymphocytes such as CD4+T cells can be achieved, for example, with fluorescence-activated cell sorting (FACS). Cytotoxicity and CTL assays can be performed for instance as described in Raz et al. (1994) *Proc. Natl. Acad. Sci. USA* 91:9519-9523 and Cho et al. (2000). Cytokine concentrations can be measured, for example, by ELISA. These and other assays to evaluate the immune response to an immunogen are well known in the art. See, for example, SELECTED METHODS IN CELLULAR IMMUNOLOGY (1980) Mishell and Shiigi, eds., W. H. Freeman and Co.

Preferably, a Th1-type response is stimulated, i.e., elicited and/or enhanced. With reference to the invention, stimulating a Th1-type immune response can be determined in vitro or ex vivo by measuring cytokine production from cells treated with a BIC as compared to control cells not treated with BIC. Methods to determine the cytokine production of cells include those methods described herein and any known in the art. The type of cytokines produced in response to BIC treatment indicate a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, IFN-γ and IFN-α. In contrast, "Th2-type biased cytokines" refers to those associated with a Th2-type immune response, and include, but are not limited to, IL-4, IL-5, and IL-13. Cells useful for the determination of BIC activity include cells of the immune system, primary cells isolated from a host and/or cell lines, preferably APCs and lymphocytes, even more preferably macrophages and T cells.

Stimulating a Th1-type immune response can also be measured in a host treated with a BIC can be determined by any method known in the art including, but not limited to: (1) a reduction in levels of IL-4 or IL-5 measured before and after antigen-challenge; or detection of lower (or even absent) levels of IL-4 or IL-5 in a BIC treated host as compared to an antigen-primed, or primed and challenged, control treated without BIC; (2) an increase in levels of IL-12, IL-18 and/or IFN (α, β or γ) before and after antigen challenge; or detection of higher levels of IL-12, IL-18 and/or IFN (α, β or γ) in a BIC treated host as compared to an antigen-primed or, primed and challenged, control treated without BIC; (3) "Th1-type biased" antibody production in a BIC treated host as compared to a control treated without BIC; and/or (4) a reduction in levels of antigen-specific IgE as measured before and after antigen challenge; or detection of lower (or even absent) levels of antigen-specific IgE in a BIC treated host as compared to an antigen-primed, or primed and challenged, control treated without BIC. A variety of these determinations can be made by measuring cytokines made by APCs and/or lymphocytes, preferably macrophages and/or T cells, in vitro or ex vivo using methods described herein or any known in the art. Some of these determinations can be made by measuring the class and/or subclass of antigen-specific antibodies using methods described herein or any known in the art.

The class and/or subclass of antigen-specific antibodies produced in response to BIC treatment indicate a Th1-type or a Th2-type biased immune response by the cells. As used herein, the term "Th1-type biased" antibody production refers to the measurable increased production of antibodies associated with a Th1-type immune response (i.e., Th1-associated antibodies). One or more Th1 associated antibodies may be measured. Examples of such Th1-type biased antibodies include, but are not limited to, human IgGI and/or IgG3 (see, e.g., Widhe et al. (1998) *Scand. J. Immunol.* 47:575-581 and de Martino et al. (1999) *Ann. Allergy Asthma Immunol.* 83:160-164) and murine IgG2a. In contrast, "Th2-type biased antibodies" refers to those associated with a Th2-type immune response, and include, but are not limited to, human IgG2, IgG4 and/or IgE (see, e.g., Widhe et al. (1998) and de Martino et al. (1999)) and murine IgGI and/or IgE.

The Th1-type biased cytokine induction which occurs as a result of administration of BIC produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

In some embodiments, a Th2 response is suppressed. Suppression of a Th2 response may be determined by, for example, reduction in levels of Th2-associated cytokines, such as IL-4 and IL-5, as well as IgE reduction and reduction in histamine release in response to allergen.

V. KITS OF THE INVENTION

The invention provides kits. In certain embodiments, the kits of the invention comprise one or more containers comprising a BIC. The kits may further comprise a suitable set of instructions, generally written instructions, relating to the use of the BIC for the intended treatment (e.g., immunomodulation, ameliorating symptoms of an.infectious disease, increasing IFN-γ levels, increasing IFN-α levels, or ameliorating an IgE-related disorder).

The kits may comprise BIC packaged in any convenient, appropriate packaging. For example, if the BIC is a dry formulation (e.g., freeze dried or a dry powder), a vial with a resilient stopper is normally used, so that the BIC may be easily resuspended by injecting fluid through the resilient stopper. Ampoules with non-resilient, removable closures (e.g., sealed glass) or resilient stoppers are most conveniently used for liquid formulations of BIC. Also contemplated are packages for use in combination with a specific device, such as an inhaler, nasal administration device (e.g., an atomizer) or an infusion device such as a minipump.

The instructions relating to the use of BIC generally include information as to dosage, dosing schedule, and route of administration for the intended treatment. The containers of BIC may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

In some embodiments, the kits further comprise an antigen (or one or more antigens), which may or may not be packaged in the same container (formulation) as the BIC(s). Antigen have been described herein.

In certain embodiments, the kits of the invention comprise a BIC in the form of a BIC/microcarrier complex (BIC/MC) and may further comprise a set of instructions, generally written instructions, relating to the use of the BIC/MC complex for the intended treatment (e.g., immunomodulation, ameliorating symptoms of an infectious disease, increasing IFN-γ levels, increasing IFN-α levels, or ameliorating an IgE-related disorder).

In some embodiments, kits of the invention comprise materials for production of BIC/MC complex generally include separate containers of BIC and MC, although in certain embodiments materials for producing the MC are supplied rather than preformed MC. The BIC and MC are preferably supplied in a form which allows formation of BIC/MC complex upon mixing of the supplied BIC and MC. This configuration is preferred when the BIC/MC complex is linked by non-covalent bonding. This configuration is also preferred when the BIC and MC are to be crosslinked via a heterobifunctional crosslinker; either BIC or the MC is supplied in an "activated" form (e.g., linked to the heterobifunctional crosslinker such that a moiety reactive with the BIC is available).

Kits for BIC/MC complexes comprising a liquid phase MC preferably comprise one or more containers including materials for producing liquid phase MC. For example, a BIC/MC kit for oil-in-water emulsion MC may comprise one or more containers containing an oil phase and an aqueous phase. The contents of the container are emulsified to produce the MC, which may be then mixed with the BIC, preferably a BIC which has been modified to incorporate a hydrophobic moiety. Such materials include oil and water, for production of oil-in-water emulsions, or containers of lyophilized liposome components (e.g., a mixture of phospholipid, cholesterol and a surfactant) plus one or more containers of an aqueous phase (e.g., a pharmaceutically-acceptable aqueous buffer).

VI. EXAMPLES

The following Examples are provided to illustrate, but not limit, the invention.

Example 1

Synthesis of a BIC Containing a 2'-Deoxyuridine-Based Branch-Point Nucleoside and Hexaethylene Glycol Spacer Moieties A branched immunomodulatory compound, B07, having the structure shown below, was synthesized. The nucleic acid moieties of B07 are DNA and the bN is 2'-deoxyuridine which contains a 6-hydroxy-1-aminohexyl-3(E)-acrylamido (AHA)-SM component linked to the 5 position of the 2'-deoxyuridine (U-AHA; Biosearch Technologies). See FIG. 1A. The NAMs and bN were joined, as shown in the structure below, via hexaethylene glycol (HEG) and the AHA-SM component. The linkages between the HEG componants and the NAM, between the HEG components and bN, and the AHA and HEG components were phosphorothioate diesters. Synthesis of the nucleic acid moieties was in the 3' to 5' direction using 5'-O-(4,4'-dimethyoxytrityl)-3'-(N,N'-diisopropyl) 2-cyanoethylphosphoramidite protected nucleoside monomers.

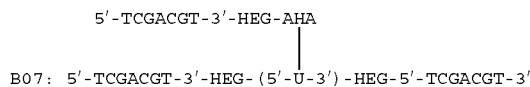

The attachment points to the branch-point nucleoside are as follows:
5'=attachment through the 5'-OH
3'=attachment through the 3'-OH
b=attachment through the base, in this case attachment is through the AHA group covalently linked to the 5-position of the 2'-dU branch-point nucleoside B07 was synthesized using a Perseptive Biosystems Expedite 8909 automated DNA synthesizer using the manufacturer's protocols for 15 μmol phosphorothioate DNA with the specified modifications. The phosphoramidite forms of the nucleoside monomers, the hexaethylene glycol spacer (4,4'-O-dimethoxytrityl-hexaethylene glycol-O-(N,N-diisopropyl) 2-cyanoethylphosphoramidite, abbreviated as DMT-HEG-CEP, ChemGenes, Ashland, Mass.), and the T-C6 branch-point nucleoside monomer (5-(N-(6-O-levulinoyl-1-aminohexyl)-3(E)-acrylamido-5'-O-(4,4'-dimethoxytrityl)-3'-O-(N,N-diisopropyl) (2-cyanoethylphosphoramidite)-2'-deoxyuridine, abbreviated as 5'-DMT-T C6-O-Lev 3'-CEP, Biosearch Technologies, Novato, Calif.) were dissolved at a concentration of 0.1 M in acetonitrile. A 0.02 M solution of xanthane hydride in 9:1 acetonitrile:pyridine was used for sulfurization of the phosphite triester groups to phosphorothioate linkages.

The DNA synthesizer was programmed to add the nucleic acid moieties, spacer moieties, and branch point nucleoside in the following order.
1. Use a 3'-support bound "T" solid support
2. Synthesis of 5'-TCGACG-3'
3. Addition of HEG spacer phosphoramidite
4. Addition of U-AHA branch-point nucleoside
5. Removal of the levulinyl group with hydrazine hydrate, as described below
6. Addition of HEG spacer phosphoramidite
7. Synthesis of 5'-TCGACGT-3'

The standard synthesis cycle consisted of a detritylation step, a coupling step (phosphoramidite monomer plus 1H-tetrazole), a capping step, a sulfurization step, and a final capping step. After the synthesis cycle that added the U-AHA branch point nucleoside was complete, the column was removed from the synthesizer and treated with 0.5 M hydrazine hydrate in 3:2 pyridine:acetic acid/pH 5.1 (10 mL) for 5 min to remove the levulinyl group. The solid support was washed well with acetonitrile (2×20 mL) and placed back on the DNA synthesizer for the completion of the synthesis. For steps 6 and 7, each reagent delivery in the synthesis cycle was doubled because two chains were built simultaneously. At the completion of assembly, the "trityl-on" compound was cleaved from the controlled-pore glass solid support and the bases were deprotected with concentrated aqueous ammonia at 58° C. for 16 hours.

The BIC was purified by RP-HPLC on a PLRP-S column (100 A, 8 u, 75×300 mm, Polymer Labs, Amherst, Mass.) using an increasing gradient of acetonitrile in 0.1 M triethylammonium acetate/pH 7.0. The fractions containing the product were dried in vacuo, detritylated with 80% aqueous acetic acid for 15 min, and precipitated from 0.6 M sodium acetate/pH 5.1 with 2.5 volumes of cold 95% ethanol. The precipitation was repeated one time and the BIC was quantitated by dissolution in sterile water, followed by reading the absorbance at 260 nm of a diluted sample. The compound was lyophilized to a powder.

The BIC was characterized by capillary gel electrophoresis, electrospray mass spectrometry, and RP-HPLC to confirm composition and purity. An endotoxin content assay (LAL assay, Bio Whittaker) was also conducted, showing endotoxin levels were <5 EU/mg of compound (i.e., essentially endotoxin-free).

Example 2

Synthesis of a BIC Containing a 2'-Deoxycytidine-Based Branch-Point Nucleoside and Hexaethylene Glycol Spacers The branched immunomodulatory compound B08 has the structure shown below. The nucleic acid moieties of B08 are DNA and the bN is 5-methyl-2'-deoxycytidine which contains a diethylene glycol (DEG)-SM component linked to the N4 position of the 5-methyl-2'-deoxycytidine (mdC-DEG; Biosearch Technologies). See FIG. 1E. The NAMs and bN are joined, as shown in the structure below, via hexaethylene glycol (HEG) and the DEG-SM component. The linkages between the HEG componants and the NAM, between the HEG components and bN, and the DEG and HEG components are phosphorothioate diesters. Synthesis of the nucleic acid moieties is in the 3' to 5' direction using 5'-O-(4,4'-dimethyoxytrityl)-3'-(N,N'-diisopropyl) 2-cyanoethylphosphoramidite protected nucleoside monomers.

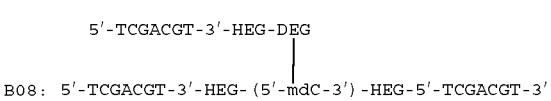

The attachment points to the branch-point nucleoside are as follows:

5'=attachment through the 5'-OH
b=attachment through the base, in this case, attachment is through the diethylene glycol (DEG) linked to the N4-position of the C branch-point nucleoside
3'=attachment through the 3'-OH B08 is synthesized as described in Example 1, except the U-AHA branch-point nucleoside is replaced with a mdC-DEG branch-point nucleoside (N4-(6-O-levulinoyl-1-diethylene glycol)-5-methyl-5'-O-(4,4'-dimethoxytrityl)-3'-O-(N,N-diisopropyl)(2-cyanoethylphosphoramidite)-2'-deoxycytidine, abbreviated as 5'-DMT-mdC(TEG-O-Lev)3'-CEP, Biosearch Technologies).

Purification and analysis are performed as described in Example 1.

Example 3

Synthesis of a BIC with All Nucleic Acid Moieties Attached via the 3'-end and Containing a 2'-Deoxyuridine-Based Branch-Point Nucleoside and Hexaethylene Glycol Spacers The branched immunomodulatory compound B01 has the structure shown below. The nucleic acid moieties of B01 are DNA and the bN is 2'-deoxyuridine which contains a 6-hydroxy-1-aminohexyl-3(E)-acrylamido (AHA)-SM component linked to the 5 position of the 2'-deoxyuridine (U-AHA; Biosearch Technologies). See FIG. 1A. The NAMs and bN are joined, as shown in the structure below, via hexaethylene glycol (HEG) and the AHA-SM component. The linkages between the HEG componants and the NAM, between the HEG components and bN, and the AHA and HEG components are phosphorothioate diesters.

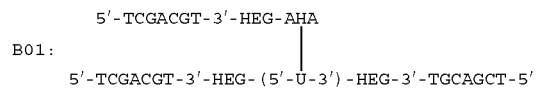

The attachment points to the branch-point nucleoside are as follows:
5'=attachment through the 5'-OH
b=attachment through the base, in this case attachment is through the AHA group covalently linked to the 5-position of the 2'-dU branch-point nucleoside
3'=attachment through the 3'-OH B01 is synthesized as described in Example 1 with the following changes. The instrument is programmed to add the nucleic acid moieties, spacer moieties, and branch point nucleoside in the following order.
1. Use a 5'-support bound "T" solid support
2. Synthesis of 3'-TGCAGC-5' using 3'-O-(4,4'-dimethyoxytrityl)-5'-(N,N'-diisopropyl) 2-cyanoethylphosphoramidite protected nucleoside monomers (synthesis in 5' to 3' direction)
3. Addition of HEG spacer phosphoramidite
4. Addition of U-AHA branch-point nucleoside
5. Removal of the levulinyl group with hydrazine hydrate, as described below
6. Addition of HEG spacer phosphoramidite
7. Synthesis of 5'-TCGACGT-3' using 5'-O-(4,4'-dimethyoxytrityl)-3'-(N,N'-diisopropyl) 2-cyanoethylphosphoramidite protected nucleoside monomers (synthesis in 3' to 5' direction)

For Step 2, the synthesis proceeds in the 5' to 3' direction using 3'-O-(4,4'-dimethyoxytrityl)-5'-(N,N'-diisopropyl) 2-cyanoethylphosphoramidite protected nucleoside monomers (Glen Research, Sterling, Va.). For Step 7, the synthesis proceeds in the 3' to 5' direction using 5'-O-(4,4'-dimethyoxytrityl)-3'-(N,N'-diisopropyl) 2-cyanoethylphosphoramidite protected nucleoside monomers. For steps 6 and 7, each reagent delivery in the synthesis cycle was doubled because two chains were built simultaneously.

Purification and analysis are performed as described in Example 1.

Example 4

Synthesis of a BIC Containing an Adenosine Branch-Point Nucleoside and Hexaethylene Glycol Spacers The branched nucleic acid molecule, B09, having the structure shown below, was synthesized using a method essentially as described in Braich and Damha, Bioconjugate Chem., 1997, 8: 370-377. The nucleic acid moieties are DNA, the spacer moieties are hexaethylene glycol (HEG), and the branch-point nucleoside is adenosine (rA). The linkages between the nucleosides, spacers, and branch-point nucleoside are all phosphorothioate esters. Synthesis of the nucleic acid moieties was in the 3' to 5' direction using 5'-O-(4,4'-dimethyoxytrityl)-3'-(N,N'-diisopropyl) 2-cyanoethylphosphoramidite protected nucleoside monomers.

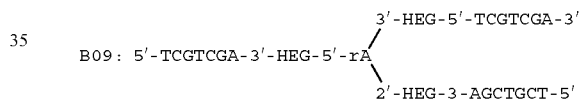

The attachment points to the branch-point nucleoside are as follows:
5'=attachment through the 5'-OH
3'=attachment through the 3'-OH
2'=attachment through the 2'-OH B09 was synthesized using a Perseptive Biosystems Expedite 8909 automated DNA synthesizer using the manufacturer's protocols for 15 μmol phosphorothioate DNA with the specified modifications. The phosphoramidite forms of the nucleoside monomers, the hexaethylene glycol spacer (DMT-HEG-CEP, ChemGenes, Ashland, Mass.), and the rA branch-point nucleoside monomer (5'-O-(4,4'-dimethoxytrityl)-3'-O-(N,N-diisopropyl) (2-cyanoethylphosphoramidite)-2'-t-butyldimethylsilyl-adenosine, abbreviated as 5'-DMT-A-2'-TBDMS-3'-CEP, Glen Research, Sterling, Va.) were dissolved at a concentration of 0.1 M in acetonitrile. A 0.3 M solution of the DMT-HEG-CEP was also prepared for the coupling to the 2'-OH group. A 0.02 M solution of xanthane hydride in 9:1 acetonitrile:pyridine was used for sulfurization of the phosphite triester groups to phosphorothioate linkages.

The DNA synthesizer was programmed to add the nucleic acid moieties, spacer moieties, and branch-point nucleoside in the following order.
1. Use a 3'-support bound "A" solid support
2. Synthesis of 5'-TCGTCG-3'
3. Addition of HEG spacer phosphoramidite 4. Addition of rA branch-point nucleoside (3' attachment)
5. Removal of the cyanoethyl protecting groups with 4:6 triethylamine in acetonitrile, as described below
6. Removal of the 2'-silyl protecting group with 1 M TBAF in THF, as described below
7. Addition of HEG spacer phosphoramidite to the 2'-OH using the 0.3 M solution in acetonitrile and a 30 min coupling time, as described below (2' and 5' attachment)
8. Synthesis of 5'-TCGTCGA-3'

After the synthesis cycle that added the rA branch point nucleoside was complete, the column was removed from the synthesizer and treated with 4:6 triethylamine in acetonitrile (v/v) for 90 min to remove the cyanoethyl phosphate protecting groups. The solid support was washed with acetonitrile (2×20 mL) and then the 2'-silyl protecting group was removed by a 10 min treatment with 1 M tetrabutylammonium fluoride (TBAF) in tetrahydrofuran (THF) (10 mL). The solid support was washed with THF (2×20 mL) and acetonitrile (2×20 mL). The column was reinstalled on the synthesizer for steps 6 and 7, for which each reagent delivery in the synthesis cycle was doubled because two chains were built simultaneously. Also, for step 6 the concentration of the HEG phosphoramidite was increased to 0.3 M and the coupling time was 30 min because of the steric hinderance at the 2'-site. Couplings in Step 7 used the usual 0.1 M phosphoramidite monomers and coupling time (2 min).

Deprotection, purification, and analysis were performed as described in Example 1.

Example 5

Synthesis of a BIC Containing an Adenosine Branch-point Nucleoside and with Three Different Nucleic Acid Moieties Directly Attached to the Branch-Point Nucleoside The branched immunomodulatory compound B10, having the structure shown below, was designed so that the nucleic acid moiety attached to the 3'-OH of the adenosine branch-point nucleoside is complementary to the nucleic acid moiety attached to the 2'-OH of the adenosine branch-point nucleoside, with the first few bases being part of a loop structure. Therefore, in the presence of salt buffers, the two nucleic acid moieties attached to the 2'- and 3'-positions of adenosine are expected to hybridize via Watson-Crick base-pairing.

B10 (SEQ ID NOS: 135, 136, and 137) was synthesized using the method essentially as described in *Bioconjugate Chem.*, 1997, 8: 370-377 and as described in Example 4, with the exceptions noted below. The nucleic acid moieties are DNA and the branch-point nucleoside is adenosine (rA). The linkages between the nucleosides and the branch-point nucleoside are all phosphorothioate esters. Synthesis of the nucleic acid moieties was in the 3' to 5' direction using 5'-O-(4,4'-dimethoxytrityl)-3'-(N,N'-diisopropyl) 2-cyanoethylphosphoramidite protected nucleoside monomers.

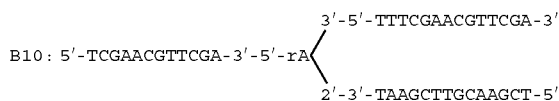

The DNA synthesizer was programmed to add the nucleic acid moieties and branch-point nucleoside in the following order.
1. Use a 3'-support bound "A" solid support
2. Synthesis of 5'-TCGAACGTTCGA-rA-TTTC-GAACGTTCG-3' (SEQ ID NO:138)
3. Detritylation and capping of the 5'-end
4. Removal of the cyanoethyl protecting groups with 4:6 triethylamine in acetonitrile, as described below
5. Removal of the 2'-silyl protecting group with 1 M TBAF in THF, as described below
6. Addition of the T phosphoramidite to the 2'-OH using the 0.3 M solution in acetonitrile and a 30 min coupling time, as described below
7. Synthesis of 5'-TCGAACGTTCGAA-3' (SEQ ID NO: 139)

After Step 2 was complete, the 4,4'-dimethoxytrityl group was removed from the 5'-end of the nucleic acid moiety and the free 5'-OH is capped with a mixture of acetic anhydride and N-methylimidazole in pyridine/THF. Then the column was removed from the synthesizer and treated with 4:6 triethylamine in acetonitrile (v/v) for 90 min to remove the cyanoethyl phosphate protecting groups. The solid support was washed with acetonitrile (2×20 mL) and then the 2'-silyl protecting group was removed by a 10 min treatment with 1 M tetrabutylammonium fluoride (TBAF) in tetrahydrofuran (THF) (10 mL). The solid support was washed with THF (2×20 mL) and acetonitrile (2×20 mL). The column was reinstalled on the synthesizer for Steps 6 and 7. For step 6, the concentration of the T phosphoramidite was increased to 0.3 M and the coupling time was 30 min because the 2'-site of the rA is sterically hindered. Couplings in Step 7 use the usual concentration of phosphoramidite monomers (0.1 M) and coupling time (2 min).

Deprotection, purification, and analysis were performed as described in Example 1.

Example 6

Preparation of a Branched BIC with a Comb Structure

Figure 5:
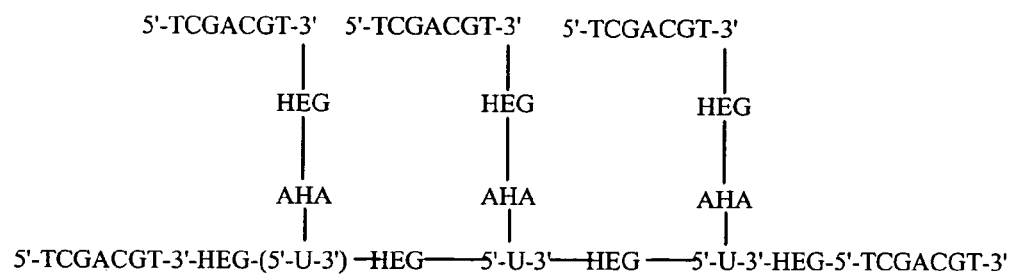
FIG. 5 shows a BIC with a "comb" structure.

The structures of the branched immunomodulatory compounds B02 and B03 are shown below and in FIGS. 5 and 6. The nucleic acid moieties of B02 and B03 are DNA and the bN is 2'-deoxyuridine which contains a 6-hydroxy-1-amino-hexyl-3(E)-acrylamido (AHA)-SM component linked to the 5 position of the 2'-deoxyuridine (U-AHA; Biosearch Technologies). See FIG. 1A. The NAMs and bN are joined, as shown in the structure below, via hexaethylene glycol (HEG) and the AHA-SM component. The linkages between the HEG components and the NAM, between the HEG components and bN, and the AHA and HEG components are phosphorothioate diesters. Synthesis of the nucleic acid moieties is in the 3' to 5' direction using 5'-O-(4,4'-dimethyoxytrityl)-3'-(N, N'-diisopropyl) 2-cyanoethylphosphoramidite protected nucleoside monomers. B02 is synthesized as described in Example 1, with the following changes.

B02  5'-TCGACGT-3'-HEG-((U-AHA)(HEG-3'-TG-CAGCT-5')-HEG)$_3$-5'-TCGACGT-3'

The DNA synthesizer is programmed to add the nucleic acid moieties and spacer moieties in the following order.
1. Use a 3'-support bound "T" solid support 2. Synthesis of 5'-TCGACG-3'
3. Addition of HEG spacer phosphoramidite
4. Addition of U-AHA branch-point nucleoside
5. Repeat steps 3 and 4 two more times
6. Removal of the levulinyl protecting groups using a 90 min treatment with 0.5 M hydrazine hydrate in pyridine: acetic acid (1:1, v/v)
7. Addition of HEG spacer phosphoramidite
8. Synthesis of 5'-TCGACGT-3'

After removal of the 3 levulinyl protecting groups, as described in Step 6, the reagents are added in amounts 3-4× the usual amounts because four nucleic acid moieties are being synthesized at one time. The BIC is purified by ion exchange chromatography using Source Q 30 (Amersham Pharmacia, Piscataway, N.J.) as described in *Organic Process Research & Development* 2000, 4: 205-213.

Figure 6:
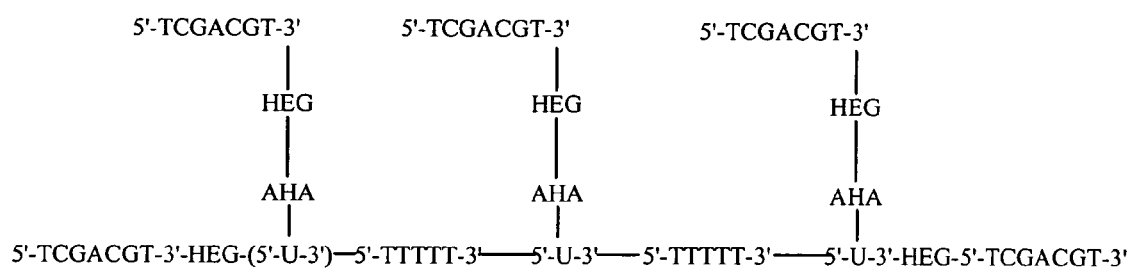
FIG. 6 shows a BIC with a "comb" structure.

B03, shown in FIG. 6, is prepared in a manner analogous to B02, except that Step 3' is inserted between Steps 3 and 4, where Step 3' is the synthesis of 5'-TTTTT-3' and Step 5 is the repetition of Steps 3' and 4 two more times. Again, all nucleotide linkages and linkages between nucleic acid moieties, nucleic acid spacer moieties and branch-point nucleosides are phosphorothioate esters.

Example 7

Preparation of a Self-Assembling BIC Containing a Self-Complimentary Nucleic Acid Sequence that Can Form a Double-Stranded Structure The structure of the branched immunomodulatory compound B04 is shown in FIG. 2 and below. The nucleic acid moieties of B04 are DNA and the bN is 2'-deoxyuridine which contains a 6-hydroxy-1-aminohexyl-3(E)-acrylamido (AHA)-SM component linked to the 5 position of the 2'-deoxyuridine (U-AHA; Biosearch Technologies). See FIG. 1A. The NAMs and bN are joined, as shown in the structure below, via hexaethylene glycol (HEG) and the AHA-SM component. The linkages between the HEG componants and the NAM, between the HEG components and bN, and the AHA and HEG components are phosphorothioate diesters. Synthesis of the nucleic acid moieties is in the 3' to 5' direction using 5'-O-(4,4'-dimethyoxytrityl)-3'-(N,N'-diisopropyl) 2-cyanoethylphosphoramidite protected nucleoside monomers. B04 is synthesized as described in Example 1.

B04 (5'-TCGACGT-3'-HEG)$_2$-(U-AHA)-HEG-5'-TTGGC-CAAGCTTGGCCAA-3' (SEQ ID NO:140)

The self-complimentary 18-mer nucleic acid moiety in the BIC is hybridized to a second molecule of the BIC, as shown in FIG. 2, by preparing a solution of B04 at a concentration of approximately 1.0 mg/ml in 50 mM sodium phosphate/150 mM sodium chloride/pH 7.2, heating the solution to 95° C. for 3 min, and then allowing the solution to slowly cool in the heat block over a period of approximately 2 hours. The formation of the double-stranded BIC is confirmed by size exclusion chromatography.

Example 8

Preparation of a BIC with an H-Structure using Phosphoramidite Chemistry

The structures of B05 and B06 are shown in FIGS. 3 and 4. The nucleic acid moieties of B05 and B06 are DNA and the bN is 2'-deoxyuridine which contains a 6-hydroxy-1-aminohexyl-3(E)-acrylamido (AHA)-SM component linked to the 5 position of the 2'-deoxyuridine (U-AHA; Biosearch Technologies). See FIG. 1A. The NAMs and bN are joined, as shown in the structure below, via hexaethylene glycol (HEG) and the AHA-SM component. The linkages between the HEG components and the NAM, between the HEG components and bN, and the AHA and HEG components are phosphorothioate diesters.

The DNA synthesizer is programmed to add the nucleic acid moieties and spacer moieties in the following order.

1. Use a 5'-support bound "T" solid support
2. Synthesis of 3'-TGCAGC-5' in the 5' to 3' direction (see Example 3)
3. Addition of HEG spacer phosphoramidite
4. Addition of U-AHA branch-point nucleoside
5. Addition of HEG spacer phosphoramidite
6. Synthesis of 5'-TCGACGT-3' in the 3' to 5' direction
7. Detritylation and capping of the 5'-TCGACGT-3' moiety
8. Removal of the levulinyl protecting group with 0.5 M hydrazine hydrate in pyridine:acetic acid (3:2, v/v), 5 min
9. Addition of HEG spacer phosphoramidite
10. Addition of U-AHA branch-point nucleoside
11. Addition of HEG spacer phosphoramidite
12. Synthesis of 5'-TCGACGT-3' in the 3' to 5' direction
13. Detritylation and capping of the 5'-TCGACGT-3' moiety
14. Removal of the levulinyl protecting group with 0.5 M hydrazine hydrate in pyridine:acetic acid (3:2, v/v), 5 min
15. Addition of HEG spacer phosphoramidite
16. Synthesis of 5'-TCGACGT-3' in the 3' to 5' direction This method results in a BIC with an H-structure. Using this method, the DNA sequences can be independently selected.

Purification is performed as described in Example 6 and analysis is performed as described in Example 1.

The branched immunomodulatory compound B06, shown in FIG. 6, is prepared in a manner analogous to B05, except that Step 9 is the synthesis of 5'-TTTTT-3' instead of addition of the HEG spacer phosphoramidite. All nucleotide linkages and linkages between nucleic acid moieties, nucleic acid spacer moieties and branch-point nucleosides in B05 are phosphorothioate esters.

Example 9

Immunomodulation of Human Cells by BICs

Tests were conducted to assess the immunomodulatory activity of a BIC and to compare that activity to polynucleotides and chimeric molecules containing spacer moieties that do not contain branch-point nucleosides.

BIC B07 was synthesized as described supra.

Peripheral blood was collected from volunteers by venipuncture using heparinized syringes. Blood was layered onto a FICOLL® (Amersham Pharmacia Biotech) cushion and centrifuged. PBMCs, located at the FICOLL® interface, were collected, then washed twice with cold phosphate buffered saline (PBS). The cells were resuspended and cultured in 48 well plates or 96-well plates at $2 \times 10^6$ cells/mL at 37° C. in RPMI 1640 with 10% heat-inactivated human AB serum plus 50 units/mL penicillin, 50 µg/mL streptomycin, 300 µg/mL glutamine, 1 mM sodium pyruvate, and 1×MEM non-essential amino acids (NEAA).

The cells were cultured in the absence of test samples, in the presence of test samples at 20 μg/ml (0.5 OD/ml), or in the presence of test samples at 20 μg/ml premixed with 100 μg/ml cationic poly(lactic acid, glycolic acid) microcarriers (cPLGA; see infra) (when used) for 24 hours. Cell-free medium was then collected from each well and assayed for IFN-γ and IFN-α concentrations. SAC (Pansorbin CalBiochem, 1/5000 dilution) was used as a positive control. SAC is Staph. aureus (cowan) cell material.

Cationic poly(lactic acid, glycolic acid) microcarriers (cPLGA) were prepared as follows. 0.875 g of poly (D,L-lactide-co-glycolide) 50:50 polymer (Boehringer Mannheim, Indianapolis, Ind.) with an intrinsic viscosity of 0.41 dl/g (0.1%, chloroform, 25° C.) was dissolved in 7.875 g of methylene chloride at 10% w/w concentration, along with 0.3 g of DOTAP. The clear organic phase was then emulsified into 500 ml of PVA aqueous solution (0.35% w/v) by homogenization at 4000 rpm for 30 minutes at room temperature using a laboratory mixer (Silverson L4R, Silverson Instruments). System temperature was then raised to 40° C. by circulating hot water through the jacket of the mixing vessel. Simultaneously, the stirring rate was reduced to 1500 rpm, and these conditions were maintained for 2 hours to extract and evaporate methylene chloride. The microsphere suspension was allowed to cool down to room temperature with the help of circulating cold water.

IFN-γ and IFN-α were assayed using CYTOSCREEN™ ELISA kits from BioSource International, Inc., according to the manufacturer's instructions.

Examples from results of the assay are shown in Example 10, below.

Example 10

Immunomodulatory Activity of BIC B07

Compound B07 (see Example 1, above) was tested for immunomodulatory activity in human PBMC cells as outlined in Example 9, above. For comparison purposes, the immunomodulatory activities of a variety of polynucleotides and chimeric molecules containing spacer moieties were also assayed. The compounds assayed for immunomodulatory activity and their structures are shown in Table 2, below. The syntheses and features of immunomodulatory chimeric molecules like compounds C-101, C-124, and C-125 are described in U.S. patent application Ser. No. 10/176,883 entitled, "Chimeric Immunomodulatory Compounds and Methods of Using the Same," filed on Jun. 21, 2002, herein incorporated by reference. All nucleotide linkages and linkages between NAMs, spacer moieties and branch-point nucleosides in the listed compounds are phosphorothioate esters. HEG=hexaethylene glycol; symmetrical doubler=1,3-diamino-2-propanol; trebler=modified pentaerythritol; T-C6=2'-deoxyuridine; AHA=aminohexyl-3(E)-acrylamido linked at the C-5 position of 2'-deoxyuridine (see FIG. 1A). The compounds were each tested both alone and formulated with cPLGA (see Example 9, supra).

TABLE 2

TEST COMPOUNDS

| Compound Designation Number | Structure |
|---|---|
| P-6 | 5'-TGA CTG TGA ACG TTC GAG ATG A-3' (SEQ ID NO:141) |
| P-7 | 5'-TGA CTG TGA ACC TTA GAG ATG A-3' (SEQ ID NO:142) |
| C-101 | (5'-TCGACGT-3'-HEG)$_2$-glycerol-HEG-5'-TCGACGT-3' |
| M-100 | (5'-TAGTCAT-3'-HEG)$_2$-glycerol-HEG-5'-AACCTTC-3' |
| C-124 | (5'-TCGACGT-3'-HEG)$_2$-symmetrical doubler-HEG-5'-TCGACGT-3' |
| M-101 | (5'-TAGTCAT-3'-HEG)$_2$-symmetrical doubler-HEG-5'-TAGTCAT-3' |
| C-125 | (5'-TCGACGT-3'-HEG)$_3$-trebler-HEG-5'-TCGACGT-3' |
| M-102 | (5'-TAGTCAT-HEG)$_3$-trebler-HEG-5'-TAGTCAT-3' |
| B07 | (5-TCGACGT-3'-HEG)$_2$-(T-C6)-AHA-HEG-5'-TCGACGT-3'[7] |

In the human PBMC assay, background levels of IFN-γ can vary, even significantly, with the donor. Levels of IFN-α generally exhibit low background levels under unstimulated conditions.

The results of the immunomodulatory assay in PBMCs are shown in Table 3, below. The numbers "17—" represent individual donors. The mean results of the immunomodulatory assays for the various compounds are also summarized in Table 4, below.

TABLE 3

| stim | IFN-γ (pg/ml) | | | | | IFN-α (pg/ml) | | | | |
|---|---|---|---|---|---|---|---|---|---|---|
| | 17240 | 17241 | 17242 | 17243 | mean | 17240 | 17241 | 17242 | 17243 | mean |
| medium | 10 | 73 | 15 | 39 | 34 | 34 | 30 | 30 | 30 | 31 |
| P-6 | 172 | 158 | 47 | 77 | 113 | 86 | 30 | 57 | 30 | 51 |
| P-7 | 35 | 127 | 10 | 58 | 58 | 30 | 30 | 30 | 30 | 30 |
| C-101 | 237 | 147 | 73 | 142 | 150 | 2189 | 520 | 1071 | 293 | P-6 |
| M-100 | 27 | 71 | 10 | 41 | 37 | 30 | 30 | 30 | 30 | 30 |
| C-124 | 303 | 155 | 65 | 142 | 166 | 1048 | 239 | 1186 | 249 | 680 |
| M-101 | 24 | 10 | 10 | 22 | 16 | 39 | 30 | 30 | 30 | 32 |
| C-125 | 253 | 136 | 85 | 184 | 165 | 1519 | 67 | 1284 | 309 | 795 |
| M-102 | 34 | 24 | 10 | 45 | 28 | 30 | 30 | 30 | 30 | 30 |
| B07 | 205 | 108 | 30 | 140 | 121 | 1080 | 122 | 1039 | 201 | 610 |
| B07 (#2) | 207 | 129 | 48 | 158 | 135 | 1046 | 253 | 1365 | 520 | 796 |
| PLGA | 10 | 10 | 10 | 10 | 10 | 30 | 30 | 30 | 30 | 30 |
| P-6 + PLGA | 1127 | 230 | 480 | 435 | 568 | 587 | 54 | 261 | 280 | 295 |
| P-7 + PLGA | 39 | 54 | 10 | 32 | 34 | 30 | 30 | 30 | 30 | 30 |
| C-101 + PLGA | 2841 | 738 | 1046 | 665 | 1323 | 7104 | 4078 | 5640 | 5612 | 5609 |
| M-100 + PLGA | 434 | 52 | 20 | 36 | 136 | 30 | 37 | 30 | 181 | 69 |
| C-124 + PLGA | 3517 | 1979 | 2831 | 2319 | 2661 | 7975 | 5743 | 6810 | 7538 | 7017 |
| M-101 + PLGA | 236 | 43 | 24 | 64 | 92 | 46 | 37 | 38 | 152 | 68 |
| C-125 + PLGA | 1469 | 492 | 805 | 790 | 889 | 7676 | 5048 | 6483 | 6187 | 6348 |
| M-102 + PLGA | 71 | 99 | 14 | 59 | 61 | 69 | 206 | 40 | 24 | 85 |
| B07 + PLGA | 1693 | 611 | 603 | 625 | 883 | 8247 | 6635 | 7062 | 7249 | 7298 |
| B07 #2 + PLGA | 2025 | 524 | 853 | 664 | 1016 | 12598 | 6825 | 9354 | 7216 | 8998 |
| SAC | 4559 | 4510 | 2997 | 3409 | 3869 | 712 | 2082 | 744 | 1638 | 1294 |

TABLE 4

| stim | IFN-γ | | IFN-α | | |
|---|---|---|---|---|---|
| | −PLGA | +PLGA | −PLGA | +PLGA | |
| medium | 34 | 10 | 31 | 30 | |
| P-6 | 113 | 568 | 51 | 295 | 5'-TGA CTG TGA ACG TTC GAG ATG A-3' (SEQ ID NO:143) |
| P-7 | 58 | 34 | 30 | 30 | 5'-TGA CTG TGA ACC TTA GAG ATG A-3' (SEQ ID NO:144) |
| C-101 | 150 | 1323 | P-6 | 5609 | (5'-TCGACGT-3'-HEG)$_2$-glycerol-HEG-5'-TCGACGT-3' |
| M-100 | 37 | 136 | 30 | 69 | (5'-TAGTCAT-3'-HEG)$_2$-glycerol-HEG-5'-AACCTTC-3' |
| C-124 | 166 | 2661 | 680 | 7017 | (5'-TCGACGT-3'-HEG)$_2$-symmetrical doubler-HEG-5'-TCGACGT-3' |
| M-101 | 16 | 92 | 32 | 68 | (5'-TAGTCAT-3'-HEG)$_2$-symmetrical doubler-HEG-5'-TAGTCAT-3' |
| C-125 | 165 | 889 | 795 | 6348 | (5'-TCGACGT-3'-HEG)$_3$-trebler-HEG-5'-TCGACGT-3' |
| M-102 | 28 | 61 | 30 | 85 | (5'-TAGTCAT-HEG)$_3$-trebler-HEG-5'-TAGTCAT-3' |
| B07 | 121 | 883 | 610 | 7298 | (5'-TCGACGT-3'-HEG)$_2$-(T-C6 brancher)-HEG-5'-TCGACGT-3' |
| B07 #2 | 135 | 1016 | 796 | 8998 | (5'-TCGACGT3'-HEG)$_2$-(T-C6 brancher)-HEG-5'-TCGACGT-3' |

In these PBMC assays, BIC B07 was shown to have activity similar to the immunomodulatory chimeric compounds C-101, C-124, and C-125 with respect to the induction of IFN-γ and IFN-α. BIC B07 was also shown to have far superior immunomodulatory activity than the linear polynucleotide P-6 which contained a 5'-TCG-3' sequence.

Example 11

Preparation of Cationic Biodegradable Microcarriers

Cationic poly(lactic acid, glycolic acid) microcarriers (cPLGA) were prepared as follows. 0.875 g of poly (D,L-lactide-co-glycolide) 50:50 polymer (Boehringer Mannheim, Indianapolis, Ind.) with an intrinsic viscosity of 0.41 dl/g (0.1%, chloroform, 25° C.) was dissolved in 7.875 g of methylene chloride at 10% w/w concentration, along with 0.3 g of DOTAP. The clear organic phase was then emulsified into 500 ml of PVA aqueous solution (0.35% w/v) by homogenization at 4000 rpm for 30 minutes at room temperature using a laboratory mixer (Silverson L4R, Silverson Instruments). System temperature was then raised to 40° C. by circulating hot water through the jacket of the mixing vessel. Simultaneously, the stirring rate was reduced to 1500 rpm, and these conditions were maintained for 2 hours to extract and evaporate methylene chloride. The microsphere suspension was allowed to cool down to room temperature with the help of circulating cold water.

Microcarriers were separated by centrifugation at 8000 rpm for 10 minutes at room temperature (Beckman Instruments) and resuspended in deionized water by gentle bath sonication. The centrifugal wash was repeated two additional times to remove excess PVA from the particle surface. Final centrifugal pellets of particles were suspended in approximately 10 ml of water, and lyophilized overnight. The dried cationic microcarrier powder was characterized for size and surface charge: mean size (number weighted, $\mu$)=1.4; zeta potential (mV)=32.4.

Example 12

Immunomodulation of Mouse Cells by BIC

BICs are synthesized as described in Examples 1-8 and tested for immunomodulatory activity on mouse splenocytes. Immunostimulation is assessed by measurement of cytokine secretion into the culture media. Cytokine levels in the culture supernatant are determined by enzyme-linked immunosorbent assay (ELISA) tests.

Cells are isolated and prepared using standard techniques. Spleens of 8 to 20 week-old BALB/c mice are harvested and the splenocytes isolated using standard teasing and treatment with ACK lysing buffer from BioWhittaker, Inc. Four spleens are pooled in this experiment. Isolated cells are washed in RPMI 1640 media supplemented with 2% heat-inactivated fetal calf serum (FCS), 50 µM 2-mercaptoethanol, 1% penicillin-streptomycin, and 2 mM L-glutamine and resuspended at approximately $7 \times 10^5$ cells/ml in 10% FCS/RPMI (RPMI 1640 media with 10% heat-inactivated FCS, 50 µM 2-mercaptoethanol, 1% penicillin-streptomycin, and 2 mM L-glutamine).

Cell cultures are set up in triplicate with approximately $7 \times 10^5$ cells/well in a 96-well flat microtiter plate in 100 µl 10%FCS/RPMI with the cells allowed to rest for at lest 1 hour after plating. The indicated test compounds are incubated 0.1, 1.0 and 5.0 µg/ml for 24 hours at 37° C. Cytokine production by the cells is determined by ELISAs.

Example 13

Effects of BICs in B-Cell Proliferation Assay

Human PBMCs are isolated from heparanized blood from two normal subjects. Some PBMCs are held in reserve while the remainder is incubated with CD19+MACS beads (Miltenyi Biotec). These cells are then passed through a magnet, separating the CD19+B cells through positive selection. This population is >98% CD19+ as determined by FACS analysis. B cells are then cultured at $1 \times 10^5$/200 µl/well in 96-well round-bottomed plates. Cells are stimulated in triplicate with 2 µg/ml BIC or control compounds. The culture period is 48 hours at 37° C. At the end of the culture period, the plates are pulsed with $^3$H-thymidine, 1 µCi/well, and incubated for an additional 8 hours. Then the plates are harvested using standard liquid scintillation techniques and data is collected in counts per minutes (cpm).

Example 14

In Vivo Activity of BICs

An in vivo study is performed by injecting mice (10 mice/group) subcutaneously in the scruff of the neck with 20 ug (200 ul volume) of P-6 (positive control), P-7 (negative control), C-9, C-23, P-1 or P-11. Blood is collected 2 hours later. For the LPS positive control group, mice are injected intraperitoneally with a 200 ul volume, and blood is collected 1.5 hours later (i.e., at the peak of LPS induced TNF-α activity). The blood is clotted and the serum is prepared and stored at −80° C. until assayed. Serum cytokines are assayed using Biosource cytoscreen kits for TNF-α and Pharmingen antibody pairs for mIL-6 and mIL-12. All samples are assayed in duplicate.

Example 15

Primate Immune Response to Antigen and BICs

Immune responses to administration of hepatitis B surface antigen (HBsAg) in the presence of BICs are examined in baboons.

HBsAg is recombinant HBsAg produced in yeast. Groups of baboons (eight animals per group) included male and female baboons with weights ranging from 8-31 kg (group mean weights at 13-16 kg) at the start of the study.

The baboons are immunized two times, at a two-month interval (0 and 2 months), by intramuscular injection (IM) with 20 µg HBsAg in a 1 ml volume. As outlined below, some of the groups also received BICs (C-8 or C-9) or a positive control (P-6) with the HBsAg.

Bleeds on all animals are collected prior to immunization and at 2 weeks post-immunization. Anti-HBsAg IgG titers are measured as follows. Baboon serum samples are analyzed by AUSAB EIA commercial kit (Abbott Labs Cat. # 9006-24 and 1459-05) using human plasma derived HBsAg coated beads. Samples are tested along with a panel of human plasma derived HBsAg positive and negative standards ranging from 0-150 mIU/ml. Biotin conjugated HBsAg and rabbit anti-biotin-HRP conjugated antibody is used as the secondary antibody complex used for detection. The assay is developed with ortho-phenylenediamine (OPD) and the absorbance values are determined at 492 nm with background subtraction at 600 nm (Quantum II spectrophotometer, Abbott Labs). Using the specimen absorbance value the corresponding concentration of anti-HBsAg is expressed in milli-international units per ml (mIU/ml) as determined from the standard curve according to parameters established by the manufacturer. For diluted specimens, quantitation is based on the specimen absorbance that resulted in a value between 0-150 mIU/ml, multiplying by the dilution factor to arrive at the final concentration.

Statistical analysis is done with log-transformed data by analysis of variance (NCSS97 Statistical Software program, Kaysville, Utah) using One-Way ANOVA Planned Comparison ($\alpha$=0.05). $p \leq 0.05$ is considered significant.

The animal groups tested are immunized as follows:
Group 1-20 µg HBsAg;
Group 2-20 µg HBsAg+BIC.

Example 16

In Vivo Responses Generated by a BIC-Antigen Conjugate

This example shows the induction of an antibody-mediated immune response in mice by administration of a BIC-antigen conjugate.

As described below, 10 mice/group are immunized twice intradermally (in the tail) at two week intervals with C-11/Amb a 1 conjugate synthesized as described below (1 ug or 10 ug), P-6/Amb a 1 (1 ug) or Amb a 1 (1 ug). Anti-Amb a 1-specific IgG1 and IgG2a titers are determined from sera taken 2 weeks post each injection. In vitro re-stimulations are done on spleen cells at 6 weeks post $2^{nd}$ immunization to determine Amb a 1-specific IFNγ and IL-5 responses.

General Procedure

The animal study is performed using 8-12 week old female BALB/c mice from Charles River Laboratories (Hollister, Calif.). 10 mice/group are injected twice intradermally in the tail (ID) at two-week intervals with one of the following materials: C-11/Amb a 1 conjugate (1 ug), C-11/Amb a 1 conjugate (10 ug), P-6/Amb a 1 conjugate (1 ug) or Amb a 1 antigen (1 ug). Bleeds are collected via the retro-orbital route two weeks after each of the injections and serum prepared for antibody determination. Six weeks after the $2^{nd}$ injection spleens are harvested for in vitro re-stimulation assays to determine cytokine response of IFNγ and IL-5. Spleens are assayed individually. Amb a 1 is used at 25 and 5 ug/ml for re-stimulation with $5 \times 10^5$ cells/well and supernatants harvested on Day 4 and stored at −80° C. until assayed. Controls for the in vitro assay included SAC at 0.01% and PMA/IO at 10 ng/ml and 1 uM, respectively.

Mouse anti-Amb a 1 IgG1 and IgG2a Assays

Mouse serum samples are analyzed by ELISA in 96-well round-bottom plates that are coated with 50 μl/well Amb a 1 antigen at 1 μg/ml. Goat anti-mouse IgG1 (or IgG2a) biotin conjugated antibody is used as the secondary antibody. Streptavidin-horseradish peroxidase conjugate is used for detection. The assay is developed with TMB and the absorbance values are determined at 450 nm with background subtraction at 650 nm (Emax precision microplate reader, Molecular Devices, Sunnyvale, Calif.). The titer is defined as the reciprocal of the serum dilution that gave an ELISA absorbance of 0.5 OD using 4-parameter analysis (Softmax Pro97, Molecular Devices, Sunnyvale, Calif.). All samples are tested in duplicate wells on separate plates, and the titers are reported as the mean of the two values.

Mouse IL-5 and IFN-gamma Assays

Supernatants are tested for IL-5 and IFNγ levels by capture ELISA on anti-cytokine monoclonal antibody coated plates. Biotinylated anti-cytokine MAbs are used as secondary antibodies. Streptavidin-horseradish peroxidase conjugate is used for detection and the assay is developed with TMB. Concentration is calculated from a standard curve assayed on each plate. The absorbance values are determined at 450 nm with background subtraction at 650 nm (Emax precision microplate reader, Molecular Devices, Sunnyvale, Calif.). All samples are tested in duplicate wells on separate plates, and the concentrations are reported as the mean of the two values.

Statistics are done on log transformed data with the NCSS97 program (NCSS Statistical Software, Kaysville, Utah) using One-Way ANOVA with Planned Comparisons, $\alpha=0.05$. For this study, $p<0.05$ is considered statistically significant.

Although the foregoing invention has been described in some detail by way of illustration and example for purposes of clarity and understanding, it will be apparent to those skilled in the art that certain changes and modifications may be practiced. Therefore, descriptions and examples should not be construed as limiting the scope of the invention, which is delineated by the appended claims.

All patents, patent applications, and publications cited herein are hereby incorporated by reference in their entirety for all purposes to the same extent as if each individual publication, patent or patent application were specifically and individually indicated to be so incorporated by reference.

The invention claimed is:

1. A branched immunomodulatory compound (BIC) comprising the structure

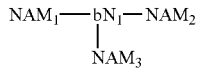

wherein $bN_1$ is a branch point nucleoside comprising a sugar molecule covalently linked to a nitrogenous base, wherein $NAM_1$, $NAM_2$, and $NAM_3$ are independently selected nucleic acid moieties, each covalently linked to a position on said sugar or said nitrogenous base either directly or through a non-nucleic acid spacer moiety, wherein the BIC has immunomodulatory activity, and wherein each of said three nucleic acid moieties comprises the sequence 5'-TCGACGT-3'.

2. A branched immunomodulatory compound (BIC) comprising the structure

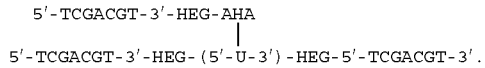

* * * * *

UNITED STATES PATENT AND TRADEMARK OFFICE
CERTIFICATE OF CORRECTION

| | | |
|---|---|---|
| PATENT NO. | : 7,625,872 B2 | Page 1 of 1 |
| APPLICATION NO. | : 10/739518 | |
| DATED | : December 1, 2009 | |
| INVENTOR(S) | : Karen L. Fearon | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 675 days.

Signed and Sealed this

Second Day of November, 2010

David J. Kappos
*Director of the United States Patent and Trademark Office*